US010580516B2

(12) United States Patent
Elashoff et al.

(10) Patent No.: US 10,580,516 B2
(45) Date of Patent: *Mar. 3, 2020

(54) SYSTEMS AND METHODS FOR DETERMINING THE PROBABILITY OF A PREGNANCY AT A SELECTED POINT IN TIME

(71) Applicant: Celmatix Inc., New York, NY (US)

(72) Inventors: Michael Elashoff, Redwood City, CA (US); Hrishikesh Karvir, Hamilton, NJ (US); Piraye Yurttas Beim, New York, NY (US)

(73) Assignee: CELMATIX, INC., New York, NY (US)

( * ) Notice: Subject to any disclaimer, the term of this patent is extended or adjusted under 35 U.S.C. 154(b) by 511 days.

This patent is subject to a terminal disclaimer.

(21) Appl. No.: 14/858,540

(22) Filed: Sep. 18, 2015

(65) Prior Publication Data

US 2016/0078172 A1    Mar. 17, 2016

Related U.S. Application Data

(63) Continuation of application No. 13/654,082, filed on Oct. 17, 2012, now Pat. No. 9,177,098.

(51) Int. Cl.
*G06F 19/00* (2018.01)
*G16B 40/00* (2019.01)
*G16B 20/00* (2019.01)

(52) U.S. Cl.
CPC ............. *G16B 40/00* (2019.02); *G16B 20/00* (2019.02)

(58) Field of Classification Search
CPC ..................................................... G06F 19/18
USPC ......................................................... 702/19
See application file for complete search history.

(56) References Cited

U.S. PATENT DOCUMENTS

| | | |
|---|---|---|
| 4,683,195 A | 7/1987 | Mullis et al. |
| 5,510,270 A | 4/1996 | Fodor et al. |
| 5,539,083 A | 7/1996 | Cook et al. |
| 5,556,752 A | 9/1996 | Lockhart et al. |
| 5,578,832 A | 11/1996 | Trulson et al. |
| 6,028,189 A | 2/2000 | Blanchard |
| 6,214,558 B1 | 4/2001 | Shuber et al. |
| 6,300,077 B1 | 10/2001 | Shuber et al. |
| 6,566,101 B1 | 5/2003 | Shuber et al. |
| 6,818,395 B1 | 11/2004 | Quake et al. |
| 6,890,763 B2 | 5/2005 | Jackowski et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,282,337 B1 | 10/2007 | Harris |
| 7,323,305 B2 | 1/2008 | Leamon et al. |
| 7,335,762 B2 | 2/2008 | Rothberg et al. |
| 7,531,635 B2 | 5/2009 | Nelson et al. |
| 7,666,593 B2 | 2/2010 | Lapidus |
| 8,024,128 B2 | 9/2011 | Rabinowitz et al. |
| 9,177,098 B2 | 11/2015 | Elashoff et al. |
| 10,162,800 B2 | 12/2018 | Elashoff et al. |
| 2002/0164629 A1 | 11/2002 | Quake et al. |
| 2003/0027208 A1 | 2/2003 | Horwitz et al. |
| 2004/0023584 A1 | 2/2004 | Michaud |
| 2005/0042702 A1 | 2/2005 | Connor et al. |
| 2005/0214836 A1 | 9/2005 | Nakamura et al. |
| 2006/0172322 A1 | 8/2006 | Nakabayashi et al. |
| 2006/0195269 A1 | 8/2006 | Yeatman et al. |
| 2009/0026082 A1 | 1/2009 | Rothberg et al. |
| 2009/0127589 A1 | 5/2009 | Rothberg et al. |
| 2009/0137478 A1 | 5/2009 | Bernstein et al. |
| 2009/0156412 A1 | 6/2009 | Boyce, IV et al. |
| 2009/0191565 A1 | 7/2009 | Lapidus et al. |
| 2010/0035252 A1 | 2/2010 | Rothberg et al. |
| 2010/0036192 A1 | 2/2010 | Yao et al. |
| 2010/0081135 A1 | 4/2010 | Dorak et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |

(Continued)

FOREIGN PATENT DOCUMENTS

| | | |
|---|---|---|
| EA | WO-0105935 A2 | 1/2001 |
| EP | 1484399 A1 | 12/2004 |

(Continued)

OTHER PUBLICATIONS

Ratnam, 2002, "Dynamics of Dnmt1 methyltransferase expression and intracellular localization during oogenesis and preimplantation development," Dev Biol 245(2):304-14.

Rosenthal & Brown, 2007, "The mouse ascending: perspectives for human-disease models," Nature Cell Biology 9:993-99.

Roth, 1998, "Finding DNA regulatory motifs within unaligned noncoding sequences clustered by whole-genome mRNA quantitation," Nat Biotechnol 16:939-45.

Rucker, 2000, "Bcl-x and Bax regulate mouse primordial germ cell survival and apoptosis during embryogenesis," Mol Endocrinol 14(7):1038-52.

(Continued)

*Primary Examiner* — Jerry Lin
(74) *Attorney, Agent, or Firm* — Wilson Sonsini Goodrich & Rosati

(57) ABSTRACT

The present invention generally relates to systems and methods for determining the probability of a pregnancy at a selected point in time. Systems and methods of the invention employ an algorithm that has been trained on a reference set of data from a plurality of women for whom at least one of fertility-associated phenotypic traits, fertility-associated medical interventions, or pregnancy outcomes are known, in which the algorithm accounts for any woman who ceases pregnancy attempts prior to reaching a live birth outcome.

15 Claims, 16 Drawing Sheets

(56) References Cited

U.S. PATENT DOCUMENTS

| | | |
|---|---|---|
| 2010/0301398 A1 | 12/2010 | Rothberg et al. |
| 2010/0304982 A1 | 12/2010 | Hinz et al. |
| 2011/0071033 A1 | 3/2011 | Yurttas et al. |
| 2011/0166029 A1 | 7/2011 | Margulies et al. |
| 2012/0094845 A1 | 4/2012 | Yurttas et al. |
| 2012/0107825 A1 | 5/2012 | Winger et al. |
| 2013/0109583 A1 | 5/2013 | Beim |
| 2014/0107934 A1 | 4/2014 | Elashoff et al. |
| 2014/0171337 A1 | 6/2014 | Beim |
| 2014/0186839 A1 | 7/2014 | Margulies et al. |
| 2014/0200916 A1 | 7/2014 | Chaudhri et al. |
| 2014/0322715 A1 | 10/2014 | Kok et al. |
| 2014/0337052 A1 | 11/2014 | Pellini et al. |
| 2015/0142331 A1 | 5/2015 | Beim et al. |
| 2015/0167081 A1 | 6/2015 | Keefe |
| 2015/0211068 A1 | 7/2015 | Beim et al. |
| 2016/0017426 A1 | 1/2016 | Beim et al. |
| 2016/0019299 A1 | 1/2016 | Boloor et al. |
| 2016/0078172 A1 | 3/2016 | Elashoff et al. |
| 2017/0351806 A1 | 12/2017 | Beim |
| 2018/0108431 A1 | 4/2018 | Beim et al. |
| 2019/0103175 A1 | 4/2019 | Yurttas et al. |
| 2019/0252043 A1 | 8/2019 | Elashoff et al. |
| 2019/0277856 A1 | 9/2019 | Beim et al. |

FOREIGN PATENT DOCUMENTS

| | | |
|---|---|---|
| EP | 1484399 A1 | 12/2004 |
| EP | 1947195 A1 | 7/2008 |
| EP | 1947195 B1 | 11/2010 |
| JP | 2004-533229 A | 11/2004 |
| JP | 2004533229 A | 11/2004 |
| JP | 2005502640 A | 1/2005 |
| WO | 2001/05935 A2 | 1/2001 |
| WO | 2001/005935 A2 | 1/2001 |
| WO | 2002/081492 A1 | 10/2002 |
| WO | WO-02081492 A1 | 10/2002 |
| WO | 03/011326 A1 | 2/2003 |
| WO | WO-03011326 A1 | 2/2003 |
| WO | WO-2005007687 A1 | 1/2005 |
| WO | 2006/055761 A1 | 5/2006 |
| WO | WO-2006055761 A1 | 5/2006 |
| WO | 2008/109147 A2 | 9/2008 |
| WO | WO-2008109147 A2 | 9/2008 |
| WO | 2009/109043 A1 | 9/2009 |
| WO | WO-2009109043 A1 | 9/2009 |
| WO | 2010/147714 A1 | 12/2010 |
| WO | WO-2010147714 A1 | 12/2010 |
| WO | 2011031786 A2 | 3/2011 |
| WO | WO-2011031786 A2 | 3/2011 |
| WO | 2011/133175 A1 | 10/2011 |
| WO | WO-2011133175 A1 | 10/2011 |
| WO | WO-2012009483 A1 | 1/2012 |
| WO | 2013/052505 A2 | 4/2013 |
| WO | WO-2013052505 A2 | 4/2013 |
| WO | 2014/062393 A1 | 4/2014 |
| WO | WO-2014062393 A1 | 4/2014 |
| WO | 2015/112972 A1 | 7/2015 |
| WO | WO-2015112972 A1 | 7/2015 |
| WO | 2016011377 A1 | 1/2016 |
| WO | WO-2016011377 A1 | 1/2016 |
| WO | WO-2016094583 A2 | 6/2016 |
| WO | WO-2017070258 A1 | 4/2017 |
| WO | WO-2017210327 A1 | 12/2017 |
| WO | WO-2018071896 A1 | 4/2018 |
| WO | WO-2018152001 A1 | 8/2018 |
| WO | WO-2019168971 A1 | 9/2019 |

OTHER PUBLICATIONS

Ruczinski, 2003, Journal of Computational and Graphical Statistcs 12:475-512.

Sahoo, 2011, Microdeletion of Xq28 involving the AFF2 (FMR2) gene in two unrelated males with developmental delay, Am. J. Med. Genet A 155A:3110-15.

Salih, 2008, Regulation of catechol O-methyltransferase expression in granulosa cells: a potential role for follicular arrest in polycystic ovary syndrome, Fertility and Sterility 89(5) Supplement:1414-21.

Santini, 2003, "Evolutionary conservation of regulatory elements in vertebrate Hox gene clusters," Genome Research 13.6a:1111-22.

Santos, 2002, Dynamic Reprogramming of DNA Methylation in the Early Mouse Embryo, Dev Biol 241(1):172-82.

Saskova, 2008, "Aurora kinase A controls meiosis I progression in mouse oocytes," Cell Cycle 7(15):2368-76.

Sato et al., 2011, Characterization of porcine autism susceptibility candidate 2 as a candidate gene for the number of corpora lutea in pigs, Animal Reproduction Science 126:211-20.

Schena, 1995, Quantitative Monitoring of Gene Expression Patterns with a Complementary DNA Microarray, Science 270:467-70.

Schmidt, 2011, Prenatal vitamins, one-carbon metabolism gene variants, and risk for autism, Epidemiology 22 (4):476-85.

Schneider-Gadicke, 1989, "ZFX has a gene structure similar to ZFY, the putative human sex determinant, and escapes X inactivation," Cell 57(7):1247-58.

Schultz, 1977, Biochemical studies of mammalian oogenesis: protein synthesis during oocyte growth and meiotic maturation in the mouse, Journal of Cell Science 24:167-94.

Schultz, 2002, The molecular foundations of the maternal to zygotic transition in the preimplantation embryo, Hum Reprod Update 8:323-31.

Schumann, 2011, Genome-wide association and genetic functional studies identify autism susceptibility candidate 2 gene (AUTS2) in the regulation of alcohol consumption, Proc. Natl. Acad. Sci. U.S.A. 108:7119-24.

Seydoux, 2006, Pathway to totipotency: lessons from germ cells, Cell 127:891-904.

Shalon, 1996, A DNA microarray system for analyzing cmopelx DNA samples using two-color fluorescent probe hybridization, Genome Res 6:639-45.

Sharan, 2004, "BRCA2 deficiency in mice leads to meiotic impairment and infertility," Development 131(1):131-42.

Soni & Meller, 2007, Progress toward ultrafast DNA sequencing using solid-state nanopores, Clin Chem 53: 1996-2001.

Soyal, 2000, "FIGalpha, a germ cell-specific transcription factor required for ovarian follicle formation," Development 127(21):4645-54.

Stanislawska-Sachadyn, 2010, The transcobalamin (TCN2) 776C>G polymorphism affects homocysteine concentrations among subjects with low vitamin B12 status, Eur J Clin Nutr 64(11):1338-43.

Sturn, 2002, "Genesis: cluster analysis of microarray data," Bioinformatics 18(1):207-08.

Suzumori, 2003, "RFPL4 interacts with oocyte proteins of the ubiquitin-proteasome degradation pathway," Proc Natl Acad Sci U S A 100(2):550-5.

Swanson, 2002, The rapid evolution of reproductive proteins, Nat Rev Genet 3:137-44.

Talkowski, 2012, Sequencing Chromosomal Abnormalities Reveals Neurodevelopmental Loci that Confer Risk across Diagnostic Boundaries, Cell 149:525-37.

Tanwar, 2008, "In vivo evidence of role of bone morphogenetic protein-4 in the mouse ovary," Anim Reprod Sci 106 (3-4):232-40.

Teixeira Filho, 2002, "Aberrant expression of growth differentiation factor-9 in oocytes of women with polycystic ovary syndrome," J Clin Endocrinol Metab 87(3):1337-44.

Telford, 1990, Transition from maternal to embryonic control in early mammalian development: a comparison of several species, Mol Reprod Dev 26:90-100.

Thompson, 1998, Mouse embryos do not wait for the MBT: chromatin and RNA polymerase remodeling in genome activation at the onset of development, Dev Genet 22:31-42.

Tian, 2009, Evolution and functional divergence of NLRP genes in mammalian reproductive systems, BMC Evol Biol 9:202.

Tian, 2009, Gene Birth, Death, and Divergence: the Different Scenarios of Reproduction Related Gene Evolution, Biology of Reproduction 80:616-21.

(56) References Cited

OTHER PUBLICATIONS

Tokushige, 2006, High density of small nerve fibres in the functional layer of the endometrium in women with endometriosis, Human Reproduction 21(3):782-87.
Toralova, 2009, "Silencing CENPF in bovine preimplantation embryo induces arrest at 8-cell stage," Reproduction 138 (5):783-91.
Tormala, 2008, Zona pellucida components are present in human fetal ovary before follicle formation, Mol Cell Endocrinol 289(1-2):10-15.
Tschopp, 2003, NALPs: a novel protein family involved in inflammation, Nature Rev Malec Cell Biol 4:95-104.
Uda, 2004, "Foxl2 disruption causes mouse ovarian failure by pervasive blockage of follicle development," Hum Mol Genet 13(11):1171-81.
Uhlenhaut, 2006, "Foxl2 function in ovarian development," Mol Genet Metab 88(3):225-34.
Underwood, 1998, "A novel calcium-independent phospholipase A2, cPLA2-gamma, that is prenylated and contains homology to cPLA2," J Biol Chem 273(34):21926-32.
van Montfoort et al., 2008, "Differential gene expression in cumulus cells as a prognostic indicator of embryo viability: a microarray analysis," HMR-Basic Science of Reproductive Medicine, 14(3):157-168.
Vatansever, 2005, "Changed Bcl:Bax ratio in endometrium of patients with unexplained infertility," Acta Histochem 107 (5):345-55.
Velasco, 1999, Cloning and Characterization of Human MMP-23, a New Matrix Metalloproteinase Predominantly Expressed in Reproductive Tissues and Lacking Conserved Domains in Other Family Members, Journal of Biological Chemistry 274:4570-76.
Velculescu, 1995, Serial analysis of gene expression, Science 270:484-87.
Vernet, 1992, Changes in permissiveness for the expression of microinjected DNA during the first cleavages of mouse embryos, Mech Dev 36:129-39.
Vitale, 2007, "Proteomic profiling of murine oocyte maturation," Mol Reprod Dev 74(5):608-16.
Vitt, 2001, "Stage-dependent role of growth differentiation factor-9 in ovarian follicle development," Mol Cell Endocrinol 183(1-2):171-7.
Vogt, 2009, "Aurora kinase B, epigenetic state of centromeric heterochromatin and chiasma resolution in oocytes," Reprod Biomed Online 19(3):352-68.
Wan, 2008, "Maternal depletion of CTCF reveals multiple functions during oocyte and preimplantation embryo development," Development 135(16):2729-38.
Wang, 1996, "Purification and biochemical heterogeneity of the mammalian SWI-SNF complex," EMBO J 15 (19):5370-82.
Minaretzis et al., "Multivariate Analysis of Factors Predictive of Successful Live Births in In Vitro Fertilization (IVF) Suggests Strategies to Improve IVF Outcome," Journal of Assisted Reproduction and Genetics, vol. 15, No. 6, Jan. 1998, pp. 365-371.
Elashoff et al., "Accurate prediction of the number of cycles to achieve live birth," Fertility and Sterility, vol. 100, No. 3, Oct. 2013.
Kosaki, 2004, "Premature ovarian failure in a female with proximal symphalangism and Noggin mutation," Fertil Steril 81(4):1137-9.
Latham, 1992, Acquisition of a transcriptionally permissive state during the 1-cell stage of mouse embryogenesis, Dev Biol 149:457-62.
Lee, 2004, "Effects of bone morphogenetic protein-7 (BMP-7) on primordial follicular growth in the mouse ovary," Mol Reprod Dev 69(2):159-63.
Lefievre, 2004, "Four zona pellucida glycoproteins are expressed in the human," Hum Reprod 19(7):1580-6.
LeGouy, 1998, "Differential preimplantation regulation of two mouse homologues of the yeast SWI2 protein," Dev Dyn 212(1):38-48.
Leland, 2009, "Heterozygosity for a Bub1 mutation causes female-specific germ cell aneuploidy in mice," Proc Natl Acad Sci USA 106(31):12776-81.
Liang & Pardee, 1992, Differential display of eukaryotic messenger RNA by means of the polymerase chain reaction, Science 257:967-71.
Lockhart, 1996, Expression monitoring by hybridization to high-density oligonucleotide arrays, Nature Biotechnology 14 (13):1675.
Loffler, 2003, "Etiology of ovarian failure in blepharophimosis ptosis epicanthus inversus syndrome:FOXL2 is a conserved, early-acting gene in vertebrate ovarian development," Endocrinology 144(7):3237-43.
Loughery, 2011, DNMT1 deficiency triggers mismatch repair defects in human cells through depletion of repair protein levels in a process involving the DNA damage response, Human Molecular Genetics 20:3241-55.
Lyall, 2010, "Association between ovulation inducing drug use, infertility, and autism spectrum disorders in the nurses' health study II," Meeting for Autism Research: International Society for Autism Research [Retrieved Dec. 23, 2012] from https://imfar.confex.com/imfar/2010/webprogram/Paper5541.html. Abstract.
Lyall, 2011, Maternal Ealry Life Factors Associated with Hormone Levels and the Risk of Having a Child with an Autism Spectrum Disorder in the Nurses Health Study II, J Autism Dev Disord 41:618-27.
Ma, 2006, "Basonuclin:a novel mammalian maternal-effect gene," Development 133(10):2053-62.
Ma, 2008, Histone deacetylase 1 (HDAC1) regulates histone acetylation, development, and gene expression in preimplantation mouse embryos, Dev Biol 319:110-20.
Maldonado-Perez, 2007, "Potential roles of the prokineticins in reproduction," Trends Endocrinol Metab 18(2).
Mannikko, 2005, Association between Sequence variations in genes encoding human zona pellucida glycoproteins and fertilization failure in IVF, Human Reproduction, 20(6):1578-1585.
Maskos & Southern, 1992, Oligonucleotide hybridisations on glass supports: a novel linker for oligonucleotide synthesis and hybridisation properties of oligonucleotides synthesised in situ, Nuc Acids Res 20:1679-84.
Matzuk, 2002, Genetic dissection of mammalian fertility pathways, Nature Cell Bio 4 Suppl:s41-49.
McBride, 1983, An Investigation of Several Oeoxynucleoside Phosphoramidites Useful for Synthesizing Deoxyoligonucleotides, Tetrahedron Lett 24:245-48.
McCarthy, 2003, Loss of Bard1, the Heterodimeric Partner of the Brca1 Tumor Suppressor, Results in Early Embryonic Lethality and Chromosomal Instability, Molecular Cellular Biology 23(14):5056-63.
McKenzie, 2004, "Human cumulus granulosa cell gene expression: a predictor of fertilization and embryo selection in women undergoing IVF," Human reproduction, 19(12):2869-2874.
Medina & Lebovic, 2009, Endometriosis-associated nerve fibers and pain, Acta Obstet Gynecol Scand 88:968-75.
Messina, 2011, Dysregulation of Semaphorin7A/β1-integrin signaling leads to defective GnRH-1 cell migration, abnormal gonadal development and altered fertility, Hum Mol Genetics 20(24):4759-74.
Miettinen, 2001, Abnormal lipoprotein metabolism and reversible female infertility in HDL receptor (SR-BI)—deficient mice, J Clin Invest 108:1717-22.
Moore, 2005, "Molecular biology and physiological role of the oocyte factor, BMP-15," Mol Cell Endocrinol 234 (1-2):67-73.
Mottershead, 2008, "Characterization of recombinant human growth differentiation factor-9 signaling in ovarian granulosa cells," Mol Cell Endocrinol 283(1-2):58-67.
Moudrianakis & Beer, 1965, Base sequence determination in nucleic acids with the electron microscope, PNAS 53:564-71.
Mouillet, 2008, "DEAD-box protein-103 (DP103, Ddx20) is essential for early embryonic development and modulates ovarian morphology and function," Endocrinology 149(5):2168-75.
Murray, 1999, Microdeletions in FMR2 may be a significant cause of premature ovarian failure, Journal of Medical Genetics 36:767-70.
Nicotra, 1998, Adenosine deaminase and human reproduction: a comparative study of fertile women and women with recurrent spontaneous abortion, Am. J. Reprod. Immunol. 39:266-70.

(56) References Cited

OTHER PUBLICATIONS

Oh, 1997, "Spindlin, a major maternal transcript expressed in the mouse during the transition from oocyte to embryo," Development 124:493-503.
Okuwaki, 2012, Function of homo- and hetero-oligomers of human nucleoplasmin/nucleophosmin family proteins NPM1, NPM2 and NPM3 during sperm chromatin remodeling, Nucleic Acids Res 40(11):4861-78.
Palmer, 1990, "Comparison of human ZFY and ZFX transcripts," Proc Natl Acad Sci U S A 87(5):1681-5.
Park, 2006, Genetic approach to identify critical factors for mouse early embryogenesis, Integrative Biosciences 10:41-47.
Parker & Barnes, 1999, mRNA: Detection by In Situ and Northern Hybridization, Methods in Molecular Biology 106:247-83.
Parry, 2011, Mutations Causing Familial Biparental Hydatidiform Mole Implicate C6orf221 as a Possible Regulator of Genomic Imprinting in the Human Oocyte, Am J Hum Genet 89(3):451-58.
Pasini, 2004, "Suz12 is essential for mouse development and for EZH2 histone methyltransferase activity," EMBO J 23 (20):4061-71.
Patterson, 2003, "Proteomics: the first decade and beyond," Nat Genet Supplement 33:311-23.
Pavlik, 2011, Divergent effects of the 677C>T mutation of the 5,10-methylenetetrahydrofolate reductase (MTHFR) gene on ovarian responsiveness and anti-Mullerian hormone concentrations, Fertility and Sterility 95(7):2257-62.
Payer, 2003, "Stella is a maternal effect gene required for normal early development in mice," Curr Biol 13(23):2110-7.
Paynton, 1994, Polyadenylation and deadenylation of maternal mRNAs during oocyte growth and maturation in the mouse, Molecular Reproduction and Development 37.
Pease, 1994, Light-generated oligonucleotide arrays for rapid DNA sequence analysis, PNAS 91(11):5022-26.
Penny, 1996, "Requirement for Xist in X chromosome inactivation," Nature 379(6561):131-7.
Pittman, 2004, "Integrated modeling of clinical and gene expression information for personalized prediction of disease outcomes," PNAS 101(22):8431-36.
Pozzi, 2009, Maternal polymorphisms for methyltetrahydrofolate reductase and methionine synthetase reductase and risk of children with Down syndrome, Am J Obstet Gynecol 200(6):636.e1-6.
Prueitt, 2000, "Physical mapping of nine Xq translocation breakpoints and identification of XPNPEP2 as a premature ovarian failure candidate gene," Cytogenet Cell Genet 89(1-2):44-50.
Punnonen, 1996, "Increased levels of interleukin-6 and interleukin-10 in the peritoneal fluid of patients with endometriosis," Am J Obstet Gynecol 174(5):1522-6.
Rajkovic, 2002, "The ret finger protein-like 4 gene, Rfpl4, encodes a putative E3 ubiquitin-protein ligase expressed in adult germ cells," Mech Dev 112(1-2):173-7.
Rajkovic, 2004, "NOBOX deficiency disrupts early folliculogenesis and oocyte-specific gene expression," Science 305 (5687):1157-9.
Rankin, 1999, "Abnormal zonae pellucidae in mice lacking ZP1 result in early embryonic loss," Development 126 (17):3847-55.
Ertunc, 2005, Glutathione-S-transferase P1 gene polymorphism and susceptibility to endometriosis, Human Reprod 20 (8):2157-61.
Esposito, 2007, "Peptidylarginine deiminase (PAD) 6 is essential for oocyte cytoskeletal sheet formation and female fertility," Mol Cell Endocrinol 273(1-2):25-31.
Evans, 2008, "Prokineticin 1 signaling and gene regulation in early human pregnancy," Endocrinology 149(6):2877-87.
Fodor, 1991, Light-directed, spatially addressable parallel chemical synthesis, Science 251:767-773.
Fogli, 2003, "Ovarian failure related to eukaryotic initiation factor 2B mutations," Am J Hum Genet 72(6):1544-50.
Friedman, 1937, "The use of ranks to avoid the assumption of normality implicit in the analysis of variance," J Amer Stat Assoc 32(200):675-701.
Froehler, 1986, Synthesis of DNA via deoxynudeoside H-phosphonate Intermediates, Nucleic Acids Res 14:5399-5407.

Fu, 2010, Clathrin recruits phosphorylated TACC3 to spindle poles for bipolar spindle assembly and chromosome alignment, J. Cell. Sci. 123:3645-51.
Fujimoto, 2010, Highdensity lipoprotein metabolism and the human embryo, Human Reproduction Update 16, 25 20-38.
Galan-Caridad, 2007, "Zfx controls the self-renewal of embryonic and hematopoietic stem cells," Cell 129(2):345-57.
Galloway, 2000, "Mutations in an oocyte-derived growth factor gene (BMP15) cause increased ovulation rate and infertility in a dosage-sensitive manner," Nat Genet 25(3):279-83.
Garcia-Cruz, 2009, "ATR, BRCA1 and gammaH2AX localize to unsynapsed chromosomes at the pachytene stage in human oocytes," Reprod Biomed Online 18(1):37-44.
Gonzalo, 2006, DNA methyltransferases control telomere length and telomere recombination in mammalian cells, Nat. Cell Biol. 8:416-24.
Greenfeld, 2007, "BAX is involved in regulating follicular growth, but is dispensable for follicle atresia in adult mouse ovaries," Reproduction 133(1):107-16.
Greenfeld, 2007, "BAX regulates follicular endowment in mice," Reproduction 133(5):865-76.
Grigorova, 2007, "Haplotype structure of FSHB, the beta-subunit gene for fertility-associated follicle-stimulating hormone:possible influence of balancing selection," Ann Hum Genet 71(Pt 1):18-28.
Gurtu, 2002, "Maternal effect for DNA mismatch repair in the mouse," Genetics 160(1):271-7.
Guzman, 2006, Cystathionine beta-synthase is essential for female reproductive function, Hum Mol Genet 15 (21):3168-76.
Halperin, 2008, "Prolactin signaling through the short form of its receptor represses forkhead transcription factor FOXO3 and its target gene gait causing a severe ovarian defect," Mol Endocrinol 22(2):513-22.
Hao, 2002, "TACC3 expression and localization in the murine egg and ovary," Mol Reprod Dev 63(3):291-9.
Hardison, 1997, Long human-mouse sequence alignments reveal novel regulatory elements: a reason to sequence the mouse genome, Genome Res 7:959-66.
Hardouin & Nagy, 2000, Mouse models for human disease, Clinical Genetics 57(4):237-44.
Harris, 2005, "INHA promoter polymorphisms are associated with premature ovarian failure," Mol Hum Reprod 11 (11):779-84.
Hawkins, 2011, Functional MicroRNA Involved in Endometriosis, Molecular Endocrinology 25(5):821-32.
Hirasawa, 2008, "Maternal and zygotic Dnmt1 are necessary and sufficient for the maintenance of DNA methylation imprints during preimplantation development, Genes Dev 22(12):1607-16.
Hod, 1992, A simplified ribonuclease protection assay, Biotechniques 13(6):852-54.
Hollingsworth, 2004, Mucins in cancer: protection and control of the cell surface, Nature Rev Cancer 4(1):45-60.
Horn, 1995, "A member of the caudal family of homeobox genes maps to the X-inactivation centre region of the mouse and human X chromosomes," Hum Mol Genet 4(6):1041-7.
Howell, 2001, "Genomic imprinting disrupted by a maternal effect mutation in the Dnmt1 gene," Cell 104(6):829-38.
Hu, 2007, "p53 regulates maternal reproduction through LIF," Nature 450(7170):721-4.
Hu, 2008, "p53:a new player in reproduction," Cell Cycle 7(7):848-52.
Hu, 2010, FIGLA, a Basic Helix-Loop-Helix Transcription Factor, Balances Sexually Dimorphic Gene Expression in Postnatal Oocytes, Mol Cell Biol, 30(14):3661-67.
Huber, 2004, matchprobes: a Bioconductor package for the sequence-matching of microarray probe elements, Bioinformatics 20(10):1651-52.
Hughes, 2001, Expression profiling using microarrays fabricated by an ink-jet oligonucleotide synthesizer, Nat Biotech 19:342-47.
Huntriss, 2002, "Isolation, characterization and expression of the human Factor in the Germline alpha (FIGLA) gene in ovarian follicles and oocytes," Mol Hum Reprod 8(12):1087-95.
Huntriss, 2006, "cDNA cloning and expression of the human NOBOX gene in oocytes and ovarian follicles," Mol Hum Reprod 12(5):283-9.

(56) References Cited

OTHER PUBLICATIONS

Iglesias 2008, "Expression pattern of glypican-3 (GPC3) during human embryonic and fetal development," Histol Histopathol 23(11):1333-40.
Ikeda, 2010, Expression of methylation pathway enzymes in bovine oocytes and preimplantation embryos, J of Exper Zoology Part A: Ecol Genet & Physiol 313A(3):129-36.
Irizarry, 2003, Exploration, normalization, and summaries of high density oligonucleotide array probe level data, Biostatistics 4(2):249-64.
Iuchi, 1999, Basonuclin, a zinc finger protein of keratinocytes and reproductive germ cells, binds to the rRNA gene promoter, Proc. Natl. Acad. Sci. U.S.A. 96:9628-32.
Jeddi-Tehrani, 2011, Analysis of Plasminogen Activator Inhibitor-1, Integrin Beta3, Beta Fibrinogen, and Methylenetetrahydrofolate Reductase Polymorphisms in Iranian Women with Recurrent Pregnancy Loss, Am J of Reprod Immunol 66(2):149-56.
Kanai, 1994, Rapid and simple method for preparation of genomic DNA from easily obtainable clotted blood, J Clin Pathol 47:1043-44.
Kang, 2009, "Single-nucleotide polymorphisms in the p53 pathway regulate fertility in humans," Proc Natl Arad Sci U S A 106(24):9761-6.
Kanka, 2003, Gene expression and chromatin structure in the pre-implantation embryo, Theriogenology 59:3-19.
Kao, 2003, "Expression profiling of endometrium from women with endometriosis reveals candidate genes for disease-based implantation failure and infertility," Endocrinology 144(7):2870-81.
Karolchik, 2008, "Comparative genomic analysis using the UCSC genome browser," Comparative Genomics (Humana Press), 17-33.
Kawai, 2012, Negative regulation of Odd-skipped related 2 by TGF-beta achieves the induction of cellular migration and the arrest of cell cycle, Biochem & Biophys Research Communications 421(4):696-700.
Kay, 1993, "Expression of Xist during mouse development suggests a role in the initiation of X chromosome inactivation," Cell 72(2):171-82.
Kim, 2008, SEBOX Is Essential for Early Embryogenesis at the Two-Cell Stage in the Mouse, Biol Reprod 79 (6):1192-1201.
Komiyana, 2007, Local activation of TGF-beta1 at endometriosis sites, J Reprod Med 52(4):306-12.
International Search Report and the Written Opinion of the International Searching Authority for PCT/US13/63381, dated Dec. 16, 2013, 11 pages.
Abrams, 1997, Cognitive, behavioral, and neuroanatomical assessment of two unrelated male children expressing FRAXE, Am. J. Med. Genet. 74:73-81.
Agarwal, 2003, Role of reactive oxygen species in the pathophysiology of human reproduction, Fertility and Sterility 79 (4):829-43.
Allingham-Hawkins, 1999, "Fragile X premutation is a significant risk factor for premature ovarian failure: The international collaborative POF in fragile X study—preliminary data," Am J Med Genet 83:322-25.
Amano, 2006, "Identification and targeted disruption of the mouse gene encoding ESG1 (PH34/ECAT2/DPPA5)," BMC Dev Biol 6:11, 9 pages.
Andersson, 2007, "Distinct and cooperative roles of mammalian Vg1 homologs GDF1 and GDF3 during early embryonic development," Dev Biol 311(2):500-11.
Aoki, 1997, Regulation of transcriptional activity during the first and second cell cycles in the preimplantation mouse embryo, Dev Biol 181:296-307.
Arnhold, 2009, "Inactivating mutations of luteinizing hormone beta-subunit or luteinizing hormone receptor cause oligoamenorrhea and infertility in women," Horm Res 71(2):75-82.
Bachvarova, 1981, Synthesis, turnover, and stability of heterogeneous RNA in growing mouse oocytes, Dev Biol 86:384-92.
Barlow, 1998, "Atm deficiency results in severe meiotic disruption as early as leptonema of prophase I," Development 125(20):4007-17.
Bayne, 2004, "Increased expression of the FIGLA transcription factor is associated with primordial follicle formation in the human fetal ovary," Mol Hum Reprod 10(6):373-81.
Bedell, 1997, "Mouse models of human disease. Part I: Techniques and resources for genetic analysis in mice," Genes and Development 11:1-10.
Bedogni, 2010, Tbr1 regulates regional and laminar identity of postmitotic neurons in developing neocortex, Proceedings of the National Academy of Sciences 107:13129-34.
Benkhalifa, 2010, Imprinting: RNA expression for homocysteine recycling in the human oocyte, Fertility & Sterility 93(5) 1585-90.
Berker, 2009, Homocysteine concentrations in follicular fluid are associated with poor oocyte and embryo qualities in polycystic ovary syndrome patients undergoing assisted reproduction, Human Reproduction 24(9):2293-2302.
Bione, 1998, "A human homologue of the *Drosophila melanogaster* diaphanous gene is disrupted in a patient with premature ovarian failure:evidence for conserved function in oogenesis and implications for human sterility," Am J Hum Genet 62(3):533-41.
Blackburn, 2000, Metabolic Consequences of Adenosine Deaminase Deficiency in Mice Are Associated with Defects in Alveogenesis, Pulmonary Inflammation, and Airway Obstruction, Journal of Experimental Medicine 192:159-70.
Blanchard, 1996, High-density oligonucleotide arrays, Biosensors & Bioelectronics 11:687-90.
Blanchette, 2002, "Discovery of regulatory elements by a computational method for phylogenetic footprinting," Genome Res 12:739-48.
Bornstein, 2000, Thrombospondin 2 Modulates Collagen Fibrillogenesis and Angiogenesis, Journal of Investigative Dermatology Symposium Proceedings 5(1):61-66.
Bottini, 2001, Autism: evidence of association with adenosine deaminase genetic polymorphism, Neurogenetics 3:111-13.
Bottini, 2002, Cooperative effect of adenosine deaminase and ABO-secretor genetic complex on susceptibility to childhood asthma, European Respiratory Journal 20:1613-15.
Brenner, 2002, Conserved regulation of the lymphocyte-specific expression of Ick in the Fugu and mammals, PNAS 99:2936-41.
Bultman, 2000, "A Brg1 null mutation in the mouse reveals functional differences among mammalian SWI/SNF complexes," Mol Cell 6(6):1287-95.
Bultman, 2006, "Maternal BRG1 regulates zygotic genome activation in the mouse," Genes Dev 20(13):1744-54.
Burney, 2007, Gene Expression Analysis of Endometrium Reveals Progesterone Resistance and Candidate Susceptibility Genes in Women with Endometriosis, Endocrinology 148(8):3814-26.
Burns, 2003, Roles of NPM2 in chromatin and nucleolar organization in oocytes and embryos, Science 300:633-36.
Carabatsos, 1998, "Characterization of oocyte and follicle development in growth differentiation factor-9-deficient mice," Dev Biol 204(2):373-84.
Carlson, 1992, Properties and localization of DNA methyltransferase in preimplantation mouse embryos: implications for genomic imprinting, Genes Dev. 6:2536-41.
Cenarro, 2003, A common variant in the ABCA1 gene is associated with a lower risk for premature coronary heart disease in familial hypercholesterolaemia, Journal of Medical Genetics 40:163-68.
Chang, 2011, MUC4 gene polymorphisms associate with endometriosis development and endometriosis related infertility, BMC Med 9:19.
Chiu, 2008, Effects of Native Human Zona Pellucida Glycoproteins 3 and 4 on Acrosome Reaction and Zona Pellucida Binding of Human Spermatozoa, Biol Reprod 79(5):869-77.
Chong, 1993, "Preimplantation prevention of X-linked disease:reliable and rapid sex determination of single human cells by restriction analysis of simultaneously amplified ZFX and ZFY sequences," Hum Mol Genet 2(8):1187-91.
Christiansen-Weber, 2000, Functional Loss of ABCA1 in Mice Causes Severe Placental Malformation, Aberrant Lipid Distribution, and Kidney Glomerulonephritis As Well As High-Density Lipoprotein Cholesterol Deficiency, The American Journal of Pathology 157:1017.
Ciccone, 2009, "KDM1B is a histone H3K4 demethylase required to establish maternal genomic imprints," Nature 461 (7262):415-8.

(56) References Cited

OTHER PUBLICATIONS

Cirio, 2008, "DNA methyltransferase lo functions during preimplantation development to preclude a profound level of epigenetic variation," Dev Biol 324(1):139-50.
Collins, 2006, The Application of genomic and proteomic technoloies in predictive, preventive and personalized medicine, Vascular Pharmacology, Vascular Pharmacology 45(5):258-67.
Davidson, 2003, "Cdx4 mutants fail to specify blood progenitors and can be rescued by multiple hox genes," Nature 425(6955):300-6.
Davis, 1993, "A null c-myc mutation causes lethality before 10.5 days of gestation in homozygotes and reduced fertility in heterozygous female mice," Genes Dev 7(4):671-82.
de Klein, 2000, "Targeted disruption of the cell-cycle checkpoint gene ATR leads to early embryonic lethality in mice," Curr Biol 10(8):479-82.
Dean, 1992, "Biology of mammalian fertilization:role of the zona pellucida," J Clin Invest 89(4):1055-9.
DeRisi, 1996, Use of a cDNA microarray to analyse gene expression patterns in human cancer, Nature Genetics 14:457-60.
Ding & Cantor, 2003, A high-throughput gene expression analysis technique using competitive PCR and matrix-assisted laser desorption ionization time-of-flight MS, PNAS 100(6):3059-64.
Dion, 2008, Dnmtl deficiency promotes CAG repeat expansion in the mouse germline, Human Molecular Genetics 17:1306-17.
Dong, 1996, "Growth differentiation factor-9 is required during early ovarian folliculogenesis," Nature 383(6600):531-5.
Doolin, 2002, Maternal Genetic Effects, Exerted by Genes Involved in Homocysteine Remethylation Influence, Am J of Human Genet 71(5):1222-26.
Dube, 1998, "The bone morphogenetic protein 15 gene is X-linked and expressed in oocytes," Mol Endocrinol 12 (12):1809-17.
Egholm, 1993,PNA hybridizes to complementary oligonucleotides obeying the Watson—Crick hydrogen-bonding rules, Nature 365:566-68.
Eisen, 1998, "Cluster analysis and display of genome-wide expression patterns," PNAS 95(25):14863-68.
Elnakat & Ratnam, 2006, Role of folate receptor genes in reproduction and related cancers, Frontiers in Bioscience 11:506-19.
Fukumura, 2003, A sensitive transcriptome analysis method that can detect unknown transcripts, Nucl. Acids. Res. 31 (16):e94.
Genuis, 2012, J of Environmental & Public Health, article ID 185731, 10 pages.
Harris, 2008, Single-Molecule DNA Sequencing of a Viral Genome, Science 320:106-109.
Heid, 1996, Real Time Quantitative PCR, Genome Research 6:986-994.
Herr, 2008, "Distribution of RNA binding protein MOEP19 in the oocyte cortex and early embryo indicates pre-patterning related to blastomere polarity and trophectoderm specification," Dev Biol 314(2):300-16.
Howe, 2011, "Limitation of inverse probability-of-censoring weights in estimating survival in the presence of strong selection bias," Am J Epidmiology 173:569-77.
International Search Report and Written Opinion for PCT/US13/63381, dated Dec. 16, 2013, 10 pages.
Kawamoto, 1999, "Expression profiling by iAFLP: a PCR-based method for genome-wide gene expression profiling," Genome Res 12:1305-12.
Kononen, 1998, "Tissue microarrays for high-throughput molecular profiling of tumor specimens," Nat Med 4(7):844-47.
Li, 2008, "A subcortical maternal complex essential for preimplantation mouse embryogenesis," Dev Cell 15(3):416-25.
Malizia, 2009, "Cumulative live-birth rates after in vitro fertilization," New England J Med 360:236-43.
Marguilies, 2005, "Genome sequencing in microfabricated high-density picolitre reactors," Nature 437:376-80.
Maxam, 1977, A new method for sequencing DNA, Proc. of National Academy of Science USA 74:560-4.

Ohsugi, 2008, "Maternally derived FILIA-MATER complex localizes asymmetrically in cleavage-stage mouse embryos," Development 135(2):259-69.
Oliphant, 2002, "BeadArray Technology: Enabling an Accurate Cost-Effective Approach to High-Throughput Genotyping," Discovery of Markers for Disease, Biotechniques 32:s56-61.
Sanger, 1977, DNA sequencing with chain-terminating inhibitors, Proc.National Academy of Science USA 74 (12):5463-7.
Schena, 1996, Parallel human genome analysis: Microarray-based expression monitoring of 1000 genes, PNAS 93:10614-19.
Tong, 1999, "A mouse gene encoding an oocyte antigen associated with autoimmune premature ovarian failure," Endocrinology 140(8):3720-6.
Tong, 2000, "Mater encodes a maternal protein in mice with a leucine-rich repeat domain homologous to porcine ribonucleaseinhibitor," Mamm Genome 11(4):281-7.
Tong, 2000, "Mater, a maternal effect gene required for early embryonic development in mice," Nat Genet 26(3):267-8.
Tong, 2002, "A human homologue of mouse Mater, a maternal effect gene essential for early embryonic development," Hum Reprod 17(4):903-11.
Tong, 2004, "Developmental expression and subcellular localization of mouse MATER, an oocyte-specific protein essential for early development," Endocrinology 145(3):1427-34.
Velculescu, 1997, Characterization of the Yeast Transcriptome, Cell, 88:243 51.
Venners, 2006, "Urinary estrogen and progesterone metabolite concentrations in menstrual cycles of fertile women with non-conception, early pregnancy loss or clinical pregnancy," Human Reprod 21(9):2272-80.
Weis, 1992, Detection of rare mRNAs via quantitative RT-PCR, Trends in Genetics 8:263-64.
Wright, 2003, "ePAD, an oocyte and early embryo-abundant peptidylarginine deiminase-like protein that localizes to egg cytoplasmic sheets," Dev Biol 256(1):73-88.
Xiao, 1999, "HSF1 is required for extra-embryonic development, postnatal growth and protection during inflammatory responses in mice," EMBO J 18(21):5943-52.
Yang, 2001, "BADGE, BeadsArray for the Detection of Gene Expression, a High-Throughput Diagnostic Bioassay," Genome Res 11:1888-98.
Yurttas, 2008, "Role for PADI6 and the cytoplasmic lattices in ribosomal storage in oocytes and translational control in the early mouse embryo," Development 135(15):2627-36.
Yurttas, 2010, Use of proteomics to identify highly abundant maternal factors that drive the egg-to-embryo transition, Reproduction 139:809-23.
Zheng 2009, "Role of Filia, a maternal effect gene, in maintaining euploidy during cleavage-stage mouse embryogenesis," Proc Natl Arad Sci U S A 106(18):7473-8.
Ertunce et al., Human Reproduction vol. 20, No. 8 pp. 2157-2161, 2005.
International Search Report for Application No. PCT/US2012/58492 dated Jan. 24, 2013.
Lyall et al., Association Between Ovulation Inducing Drug Use, Infertility, and Autism Spectrum Disorders in the Nurses' Health Study II. Meeting for Autism Research: International Society for Autism Research. May 20, 2010, Retrieved on Dec. 213, 2012.
Lyall et al., Autism Dev Disord (2011) 41:618-627, published online Aug. 10, 2010.
Rupp & Locker, 1987, "Purification and analysis of RNA from paraffin-embedded tissues," Biotechniques 6(1):56-60.
Wang, 2006, Search for basonuclin target genes, Biochemical and Biophysical Research Communications 348:1261-71.
Watkins, 2006, "An investigation into FOXE1 polyalanine tract length in premature ovarian failure," Mol Hum Reprod 12 (3):145-9.
Wilcoxon, 1945, "Individual comparisons by ranking methods," Biometrics Bulletin 1(6):80-83.
Wu, 2003, "Zygote arrest 1 (Zar1) is a novel maternal-effect gene critical for the oocyte-to-embryo transition," Nat Genet 33(2):187-91.

(56) References Cited

OTHER PUBLICATIONS

Wu, 2009, "Maternal depletion of NLRP5 blocks early embryogenesis in rhesus macaque monkeys (Macaca mulatta)," Hum Reprod 24(2):415-24.
Yan, 2005, "Mice deficient in oocyte-specific oligoadenylate synthetase-like protein OAS1D display reduced fertility," Mol Cell Biol 25(11):4615-24.
Yang, 2008, "Towards a transgenic model of Huntington's disease in a non-human primate," Nature 453:921-24.
Yang, 2008, "Parental effect of DNA (Cytosine-5) methyltransferase 1 on grandparental-origin-dependent transmission ratio distortion in mouse crosses and human families," Genetics 178(1):35-45.
Yeung, 2001, "Principal component analysis for clustering gene expression data," Bioinformatics 17(9):763-74.
Youngson, 2011, A missense mutation in the transcription factor Foxo3a causes teratomas and oocyte abnormalities in mice, Mammalian Genome 22:235-48.
Yu & Bradley, 2001, "Mouse genomic technologies: engineering chromosomal rearrangements in mice," Nature Reviews Genetics 2:780-90.
Zhang 2005, "Localization of mitotic arrest deficient 1 (MAD1) in mouse oocytes during the first meiosis and its functions as a spindle checkpoint protein," Biol Reprod 72(1):58-68.
Zhang, 2007, Distinct sets of developmentally regulated genes that are expressed by human oocytes and human embryonic stem cells, Fertil Steril 87(3):677-90.
Zhang, 2008, "Expression analysis of the NLRP gene family suggests a role in human preimplantation development," PLoS One 3(7):e2755.
Zhang, 2009, "Proteomic-based identification of maternal proteins in mature mouse oocytes," BMC Genomics 10:348.
Zhao, 2008, "Transcription factor FIGLA is mutated in patients with premature ovarian failure," Am J Hum Genet 82 (6):1342-8.
Zheng, 2007, Oocyte-Specific Genes Affect Folliculogenesis, Fertilization, and Early Development, Semin Reprod Med 25(4):243-51.
Zuccotti, 2008, Maternal Oct-4 is a potential key regulator of the developmental competence of mouse oocytes, BMC Dev Biol 8:97.
Zuccotti, 2009, "Oct-4 regulates the expression of Stella and Foxj2 at the Nanog locus:implications for the developmental competence of mouse oocytes," Hum Reprod 24(9):2225-37.
Zuccotti 2009, Role of Oct-4 during acquisition of developmental competence in mouse oocyte, Reprod Biomed Online 19 Suppl 3:57-62.
Australian Patent Examination Report No. 1 for App. No. 2010351560, dated Apr. 22, 2014, 5 pages.
International Preliminary Report on Patentability for PCT/US10/50063, dated Oct. 23, 2012, 6 pages.
International Preliminary Report on Patentability for PCT/US12/58492, dated Jan. 23, 2013, 6 pages.
International Search Report and Written Opinion for PCT/US10/50063, dated Feb. 3, 2011, 9 pages.
International Search Report and Written Opinion for PCT/US12/58492, dated Jan. 24, 2013, 7 pages.
Supplementary European Search Report for EP10850395.4, dated Sep. 2, 2013.
Sha, G., et al. "Differentially expressed genes in human endometrial endothelial cells derived from eutopic endometrium of patients with endometriosis compared with those from patients without endometriosis." Human reproduction 22.12 (2007): 3159-3169.
Crispi, Stefania, et al. "Transcriptional profiling of endometriosis tissues identifies genes related to organogenesis defects." Journal of cellular physiology 228.9 (2013): 1927-1934.
Eyster, Kathleen M., et al. "Whole genome deoxyribonucleic acid microarray analysis of gene expression in ectopic versus eutopic endometrium." Fertility and sterility 88.6 (2007): 1505-1533.
Hever, Aniko, et al. "Human endometriosis is associated with plasma cells and overexpression of B lymphocyte stimulator." Proceedings of the National Academy of Sciences 104.30 (2007): 12451-12456.
Hull, M. Louise, et al. "Endometrial-peritoneal interactions during endometriotic lesion establishment." The American journal of pathology 173.3 (2008): 700-715.
Talbi, S., et al."Molecular phenotyping of human endometrium distinguishes menstrual cycle phases and underlying biological processes in normo-ovulatory women." Endocrinology 1473 (2006): 1097-1121.
International Search Report and Written Opinion for PCT/US15/40947 dated Nov. 2, 2015 (15 pages).
Nassieri et al. Elevated Day 3 Serum Follicle Stimulating Hormone and/or Estradiol May Predict Fetal Aneuploidy. Ferility and Sterility. Apr. 1999, vol. 71, No. 4, pp. 715-718.
International Search Report and Written Opinion for PCT/US2015/012887 dated Jun. 24, 2015 (16 pages).
Crackower et al., 2003, Essential Role of Fkbp6 in Male Fertility and Homologous Chromosome Pairing in Meiosis, Science 300(5623): 1291-1295.
O'Bryan et al, 2006, Mouse models for genes involved in impaired spermatogenesis, International Journal of Andrology, 29(1): 76-88.
Yatsenko et al, 2010, The power of mouse genetics to review study spermatogenesis, J. Androl., 31(1): 34-44.
Yurttas et al, 2013, Personalized reproductive medicine on the brink: progress, opportunities and challenges ahead, Reproductive BioMedicine Online 27: 611-623.
Freudenberg et al, 2002, A similarity-based method for genome-wide prediction of disease-relevant human genes, Bioinformatics, Suppl 2:S110-5.
Ford et al., Mutation Res., vol. 313, p. 153-164 (1994).
Borowczyk, 2009, Identification of a region of the DNMT1 methyltransferase that regulates the maintenance of genomic imprints, PNAS 106(49):20806-11.
Braslavsky, 2003, Sequence information can be obtained from single DNA molecules, Proceedings of the National Academy of Sciences, (USA) 100:3960-4.
Brenner, 2000, Gene expression analysis by massively parallel signature sequencing (MPSS) on microbead arrays, Nature Biotechnology 18:630-34.
Chirgwin, 1979, Isolation of biologically active ribonucleic acid from sources enriched in ribonuclease, Biochemistry, 18:5294-99.
Christians, 1997, "Evidence for the involvement of mouse heat shock factor 1 in the atypical expression of the HSP70.1 heat shock gene during mouse zygotic genome activation," Mol Cell Biol 17(2):778-88.
Christians, 2000, "Maternal effect of Hsf1 on reproductive success," Nature 407(6805):693-4.
De Andres, 1995, Improved Method for mRNA Extraction from Paraffin a Embedded Tissues, BioTechniques 18:42-44.
Ferguson, 1996, High-Density Fiber-Optic DNA Random Microsphere Array, Nature Biotech. 14:1681-84.
Ferguson, 2000, High-Density Fiber Optic DNA Random Microsphere Array, Analytical Chemistry 72:5618.
Agresti. An Introduction to Categorical Data Analysis, John Wiley & Sons, Inc., 1996, New York, Chapter 8.
Balen et al. The Influence of Body Weight on Response to Ovulation Induction with Gonadotrophins in 335 Women with World Health Organization Group II anovulatory infertility. BJOG 113:1195-1202 (2006).
Bonilla-Musoles et al. Endometrial receptivity: evaluation with ultrasound. Ultrasound Q 29(1):3-20 (2013).
Cakmak et al. Implantation failure: molecular mechanisms and clinical treatment. Human Reproduction Update 17(2):242-253 (2011).
Cheon et al. Immune-responsive gene 1 is a novel target of progesterone receptor and plays a critical role during implantation in the mouse. Endocrinology 144(12):5623-5639 (2003).
Cingolani et al. A program for annotating and predicting the effects of single nucleotide polymorphisms, SnpEff: SNPs in the genome of Drosophila melanogaster strain w1118; iso-2; iso-3. Fly (Austin) 6(2):80-92 (2012).
Cox. Regression Models and Life-Tables. Journal of the Royal Statistical Society, Series B. 34(2):187-220 (1972).
Danecek et al. The variant call format and VCFtools. Bioinformatics 27(15):2156-2158 (2011).

(56) References Cited

OTHER PUBLICATIONS

Daya. Life table (survival) analysis to generate cumulative pregnancy rates in assisted reproduction: are we overestimating our success rates? Hum Reprod 20(5):1135-1143 (2005).
Duda. Pattern Classification and Scene Analysis. 2nd ed. John Wiley & Sons, Inc. New York. (pgs. 211-256) (1995).
Duda. Pattern Classification. Powerpoint Slides (38 pgs) (2000).
Gross. How Charles Nicolle of the Pasteur Institute discovered that epidemic typhus is transmitted by lice: reminiscences from my years at the Pasteur Institute in Paris. PNAS USA 93:10539-10540 (1996).
Huang et al. Bioinformatics enrichment tools: paths toward the comprehensive functional analysis of large gene lists. Nucleic Acids Res. 37(1):1-13 (2009).
Huang et al. Systematic and integrative analysis of large gene lists using David bioinformatics resources. Nature Protocols 4(1):44-57 (2009).
Larsen. Research On Infertility: Which Definition Should We Use? Fertility and Sterility 83(4):846-852 (2005).
Li et al. Fast and accurate short read alignment with Burrows-Wheeler ransform. Bioinformatics 25:1754-60 (2009).
Li et al. The Sequence Alignment/Map format and SAMtools. Bioinformatics 25(16):2078-9 (2009).
Lockhart et al. Expression monitoring by hybridization to high-density oligonucleotide arrays. Nature Biotechnology 14:1675-1680 (1996).
Mafra et al. Association of WNT4 Polymorphisms with Endometriosis in Infertile Patients J Assist Reprod Genet 32:1359-1364 (2015).
Maniatis et al. Molecular Cloning: A Laboratory Manual, Cold Spring Harbor, N.Y., pp. 280-281 (1982).
McKenna et al. The Genome Analysis Toolkit: a MapReduce framework for analyzing next-generation DNA sequencing data. Genome Res 20(9):1297-1303 (2010).
Palomba et al. Prospective Parallel Randomized, Double-Blind, Double-Dummy Controlled Clinical Trial Comparing Clomiphene Citrate and Metformin as the First-Line Treatment for Ovulation Induction in Nonobese Anovulatory Women with Polycystic Ovary Syndrome. J Clin Endocrinol Metab 90(7):4068-4074 (2005).
Pandey et al. The impact of female obesity on the outcome of fertility treatment. J Hum Reprod Sci 3(2):62-67 (2010).
PCT/US2017/035259 International Search Report and Written Opinion dated Sep. 8, 2017.
PCT/US2017/056759 International Search Report and Written Opinion dated Feb. 9, 2018.
PCT/US2018/017402 International Preliminary Report on Patentability dated Aug. 29, 2019.
PCT/US2018/017402 International Search Report and Written Opinion dated Jul. 6, 2018.
PCT/US2019/019816 International Search Report and Written Opinion dated Jul. 25, 2019.
Sharan et al. BRCA2 deficiency in mice leads to meiotic impairment and infertility. Development 131(1):131-42 (2004).
U.S. Appl. No. 14/051,716 Office Action dated Apr. 27, 2017.
U.S. Appl. No. 14/051,716 Office Action dated Aug. 8, 2018.
U.S. Appl. No. 14/051,716 Office Action dated May 2, 2018.
U.S. Appl. No. 14/051,716 Office Action dated Oct. 5, 2016.
U.S. Appl. No. 14/051,716 Office Action dated Sep. 20, 2017.
Wu et al. Rare-Variant Association Testing for Sequencing Data with the Sequence Kernel Association Test. American Journal of Human Genetics 89(1):82-93 (2011).
Xiao et al. Chromosomal deletions and inversions mediated by TALENS and CRISPR/Cas in zebrafish. Nucl Acids Res 41(14):e141 (2013).
Zhang et al. Proteomic-based identification of maternal proteins in mature mouse oocytes. BMC Genomics 10:348 (2009).

IVF Model Factors

| Variable | Trait | Chi.Sq | d.f. | P |
|---|---|---|---|---|
| Age (Factor+Higher Order Factors) | Age | 288.15 | 6 | <.0001 |
| IVF.Fresh (Factor+Higher Order Factors) | Cycle was fresh IVF cycle | 117.04 | 4 | <.0001 |
| Age * IVF.Fresh (Factor+Higher Order Factors) | Age versus fresh IVF cycle | 116.86 | 3 | <.0001 |
| FreshVsFrz | Fresh/frozen IVF cycle | 66.28 | 1 | <.0001 |
| Fresh.CountOfGtrOrEq2pn.1 | Count of embryos w/≥2 cells; fresh cycle | 62.88 | 1 | <.0001 |
| Fresh.AvgICM.1 | Avg blastocyst inner cell mass grade>0; fresh cycle | 42.76 | 1 | <.0001 |
| Fresh.CountOfGtrOrEq7cells | Count of embryos w/≥7 cells; fresh cycle | 34.44 | 2 | <.0001 |
| FinalNumEmbryosReplaced.t | Final number of embryo transferred | 27.28 | 1 | <.0001 |
| Cryo.AvgICM.1 | Avg blastocyst inner cell mass grade>0; cryo cycle | 25.54 | 1 | <.0001 |
| TotileMotile.1 | Totile motile sperm count>0 | 24.67 | 1 | <.0001 |
| Fresh.EmbryoStageB | Embryo stage = blastocyst; fresh cycle | 23.91 | 1 | <.0001 |
| PrevChemPregAny | Prev chemical pregnancy during prior cycle | 20.87 | 1 | <.0001 |
| Stim.Antagon | Stimulation w/antagonist treatment | 20.44 | 1 | <.0001 |
| FNER.gt.1 | Final no. of embryos inserted>1 | 20.18 | 1 | <.0001 |
| usEndoThick.i | Endometrial thickness by ultrasound | 20.16 | 2 | <.0001 |
| Fresh.BCminusCBL.1 | Blastocyst count-Count blastocysts replaced>1 | 19.78 | 1 | <.0001 |
| Cryo.AvgTroph | Avg embryo trophectoderm grade; cryo cycle | 18.56 | 1 | <.0001 |
| Diag.Uterus | Diagnosis = Uterine dysfunction | 16.01 | 1 | 1e-04 |
| Fresh.AvgTroph | Avg embryo trophectoderm grade; fresh cycle | 13.52 | 1 | 2e-04 |
| GminusP | Gravidity minus parity | 12.83 | 1 | 3e-04 |
| Cryo.EmbryoStageNB | Embryo stage not = blastocyst; cryo cycle | 12.21 | 1 | 5e-04 |
| Fresh.AvgICM | Avg blastocyst inner cell mass grade; fresh cycle | 11.97 | 1 | 5e-04 |
| usEndoP.2 | Extent of endometrial maturity by ultrasound | 8.51 | 1 | 0.0035 |
| IVFf.LogE2.i | Log peak estradiol on day of hCG administration | 7.71 | 1 | 0.0055 |
| Diag.Tubal | Diagnosis = tubal dysfunction | 5.94 | 1 | 0.0148 |
| IVFf.BAFC.i | Basal antral follicle count | 5.54 | 1 | 0.0186 |
| PrevStim.Clomid | Stimulation w/Clomid during prev cycle | 5.00 | 1 | 0.0254 |
| Cryo.BlastCount | Blastocyst count; cryo cycle | 4.63 | 1 | 0.0315 |
| Diag.Endo4 | Diagnosis = Endometriosis Stage 4 | 4.49 | 1 | 0.0341 |
| OCP | Oral contraceptive use | 4.21 | 1 | 0.0401 |
| Cryo.AvgICM | Avg blastocyst inner cell mass grade; cryo cycle | 1.86 | 1 | 0.1732 |
| TOTAL | | 1127.25 | 37 | <.0001 |

Figure 6

RE Model Factors

| Variable | Trait | Chi.Sq | d.f. | P |
|---|---|---|---|---|
| RE.IUI (Factor+Higher Order Factors) | Intrauterine insemination | 409.69 | 2 | <.0001 |
| Stim.Clomid | Stimulation w/Clomid | 282.39 | 1 | <.0001 |
| Age | Age | 241.75 | 3 | <.0001 |
| GndCP | Gonadotropin treatment | 81.85 | 1 | <.0001 |
| SurgeFollicles.i | No. of follicles post gonadotropin treatment | 55.16 | 1 | <.0001 |
| PrevChemPregAny | Prev chemical pregnancy during prior cycle | 52.47 | 1 | <.0001 |
| PrevStim.Clomid | Stimulation w/Clomid during prior cycle | 45.87 | 1 | <.0001 |
| FSHMax.i | Follicle stimulating hormone | 30.51 | 1 | <.0001 |
| PeakEndoThick.i | Peak endometrial thickness | 22.91 | 1 | <.0001 |
| Diag.Male (Factor+Higher Order Factors) | Diagnosis = Male factor infertility | 16.28 | 2 | 3e-04 |
| Diag.Male * RE.IUI (Factor+Higher Order Factors) | Male infertility vs intrauterine insemination | 16.23 | 1 | 1e-04 |
| PartnerAge.i | Age of partner | 14.10 | 1 | 2e-04 |
| BMI.cat.45.i | BMI = Obese or very obese | 11.95 | 1 | 5e-04 |
| PrevStim.GND | Stimulation w/gonadotropin during prev cycle | 6.26 | 1 | 0.0124 |
| Diag.HyAmen | Diagnosis = Hypothalamic amenorrhea | 5.37 | 1 | 0.0205 |
| Stim.DownReg | Stimulation w/ DownReg treatment protocol | 5.32 | 1 | 0.0211 |
| Diag.Ovulatory | Diagnosis = Ovulatory dysfunction | 4.64 | 1 | 0.0313 |
| Diag.PCO | Diagnosis = Polycystic ovarian syndrome | 3.76 | 1 | 0.0525 |
| TOTAL | | 1760.88 | 20 | <.0001 |

Figure 7

IVF Patients by Score Quintile

RE Patients by Score Quintile

IVF Model: Dropouts

SYSTEMS AND METHODS FOR DETERMINING THE PROBABILITY OF A PREGNANCY AT A SELECTED POINT IN TIME

CROSS-REFERENCE TO RELATED APPLICATION

This application is a continuation of U.S. patent application Ser. No. 13/654,082 filed Oct. 17, 2012, the contents of which are incorporated by reference.

FIELD OF THE INVENTION

The present invention generally relates to systems and methods for determining the probability of a pregnancy at a selected point in time.

BACKGROUND

Approximately one in seven couples has difficulty conceiving. Infertility may be due to a single cause in either partner, or a combination of factors (e.g., genetic factors, diseases, or environmental factors) that may prevent a pregnancy from occurring or continuing. Every woman will become infertile in her lifetime due to menopause. On average, egg quality and number begins to decline precipitously at 35. However, a number of women are fertile well into their 40's, while some women experience that decline much earlier in life. Although advanced maternal age (35 and above) is generally associated with poorer fertility outcomes, there is no way of diagnosing egg quality issues in younger women or knowing when a particular woman will start to experience decline in her egg quality or reserve. When a woman seeks medical assistance for difficulty conceiving, she and her partner are advised to undergo a number of diagnostic procedures to ascertain potential causes. Throughout the process, the couple's main question is whether that treatment will result in a baby.

Predicting a couple's probability of achieving a pregnancy that results in a live birth is difficult, and most statistical approaches do not provide an accurate result, generally overestimating the couple's probability of achieving such a pregnancy. That problem is illustrated with the very common technology of in vitro fertilization (IVF), a process in which egg cells are fertilized outside a woman's womb and then implanted into the womb. Generally, about 52% of couples undergoing IVF do not achieve a pregnancy after a first cycle of treatment, and about 59% of couples undergoing IVF do not achieve a live birth after a first cycle of treatment ("2009 Clinic Summary Report", Society for Reproductive Medicine). Accordingly, many couples will undergo at least one subsequent cycle of IVF, and a percentage of those couples will not achieve a pregnancy or live birth even after numerous IVF cycles.

In IVF, the statistic typically reported to couples is outcome per cycle according to maternal age (cross-sectional reporting). For example, a physician may tell a couple in which the woman is under 35 that they have a 30% to 35% probability of achieving a live birth using IVF, meaning that for each cycle of IVF started, there is a 30% to 35% probability that a live birth will be achieved. That statistic is not accurate because it does not consider the potential need for multiple IVF cycles and the likely difference in success between a first-time patient and one who did not become pregnant in previous attempts. Thus, using this cross-section reporting approach, a physician overestimates a couple's probability of achieving a pregnancy that results in a live birth from IVF.

SUMMARY

The invention generally relates to systems and methods for determining the probability of a pregnancy at a selected point in time. Generally, aspects of the invention are accomplished by using data from a cohort of women for whom at least one of fertility-associated phenotypic traits, fertility-associated medical interventions, and pregnancy outcomes are known. A plurality of fertility-associated phenotypic traits of a female subject, and optionally an intimate male partner, are obtained and run through an algorithm trained by the cohort in order to determine a probability of pregnancy at a selected point in time using a particular fertility treatment. Accordingly, systems and methods of the invention provide a longitudinal analysis that makes use of repeated observations from the cohort over time, providing a better analysis based on the specific phenotypic traits of that couple in connection with their chosen medical intervention. In this manner, systems and methods of the invention are able to more accurately report to a couple whether the selected medical intervention the couple has chosen to undergo will result in a baby.

Further, systems and methods of the invention also recognize that women that have a poor prognosis of achieving a pregnancy or a live birth after beginning a medical intervention may choose to discontinue the course of treatment, i.e., not participate in further rounds of treatment. Failure to account for the phenotypic traits of those women leads to overestimating the probability of achieving a pregnancy or a live birth using a particular fertility treatment. Systems and methods of the invention account for that potential bias by analyzing the known phenotypic traits of the women from the cohort that have chosen to discontinue treatment and factor those traits into the analysis. Accordingly, traits from women with a poor prognosis of achieving a pregnancy or live birth are accounted for and the probabilities of achieving pregnancy are adjusted over time. In this manner, bias of the cohort is eliminated and systems and methods of the invention avoid reporting an overly optimistic probability of achieving a pregnancy or live birth in connection with a particular fertility treatment.

Systems and methods of the invention are useful with all types of fertility treatments, and are particularly useful with in vitro fertilization (IVF). In the context of IVF, the invention recognizes that the chance of achieving a pregnancy or live birth varies per cycle of IVF, and also recognizes that there is a difference in success between a first-time patient and one who did not become pregnant in previous attempts. Aspects of the invention are accomplished by using data from a cohort of women for whom fertility-associated phenotypic traits and pregnancy outcomes for each cycle of in vitro fertilization are known. A plurality of fertility-associated phenotypic traits of a female subject are obtained and run through an algorithm trained by the cohort in order to determine a probability of pregnancy in a selected cycle of IVF. Since the fertility-associated phenotypic traits and pregnancy outcomes for each cycle of in vitro fertilization of the women in the cohort are already known, systems and methods of the invention are able to report a woman's probability of achieving a pregnancy or live birth for a selected cycle of IVF that accounts for whether the woman is a first-time patient or a patient that did not become pregnant or achieve a live birth in previous attempts. Therefore, instead of a cross-sectional statistic, systems and methods of the invention provide a longitudinal analysis that makes use of repeated observations from the cohort over time and provides a better analysis of a woman's history over multiple IVF cycles. The cumulative pregnancy or live-birth rate is used to determine the probability of achieving a pregnancy or live birth over the entire course of treatment.

Further, the invention recognizes that women from the cohort that have a poor prognosis of achieving a pregnancy or a live birth after a first unsuccessful cycle of IVF may choose to discontinue IVF, i.e., not participate in further IVF cycles. Failure to account for the phenotypic traits of the women with a poor prognosis discontinuing treatment, leads to reporting a higher probability of achieving a pregnancy or a live birth in a subsequent cycle of IVF than is actually expected. Systems and methods of the invention account for that potential bias by analyzing the known phenotypic traits of the women that have chosen to discontinue IVF and factoring those traits into the analysis in subsequent IVF cycles. Accordingly, traits from those women are accounted for in subsequent IVF cycles and the phenotypic make-up of the cohort remains consistent over the subsequent IVF cycles. In this manner, bias of the cohort is eliminated and systems and methods of the invention avoid reporting an overly optimistic probability of achieving a pregnancy or live birth in a subsequent IVF cycle.

There are many known fertility-associated phenotypic traits, any combination of which may be used with systems and methods of the invention. Exemplary fertility-associated phenotypic traits include age, hormone levels, ovarian antral follicle count, body mass index, and combinations thereof. Any other fertility-associated traits are also suitable for use in accordance with the present invention. Information regarding the fertility-associated phenotypic traits of the female can be obtained by any means known in the art. In many cases, such information can be obtained from a questionnaire completed by the subject that contains questions regarding certain fertility-associated phenotypic traits. Additional information can be obtained from a questionnaire completed by the subject's partner and blood relatives. Information can also be obtained from the medical history of the subject, as well as the medical history of blood relatives and other family members. Additional information can be obtained from the medical history and family medical history of the subject's partner. In other cases, the information can be obtained by analyzing a sample collected from the female subject, reproductive partner(s) of the subject, blood relatives of the subject, and a combination thereof. The sample may include human tissue or bodily fluid.

Additionally, it is known that certain genetic regions are associated with fertility. The presence of certain mutations in those genes or abnormal expression levels of those genes may indicate fertility outcomes. Accordingly, in certain aspects of the invention, genotypic data is also collected and compared to known genotypic results from the women in the cohort to help determine a probability of pregnancy at a particular point in time using a certain fertility treatment. Genotype data can be obtained by any methods known in the art, for example, by sequencing at least a portion of a relevant genetic region to determine the presence or absence of a mutation that is associated with infertility. Exemplary mutations include, without limitation, a single nucleotide polymorphism, a deletion, an insertion, an inversion, a genetic rearrangement, a copy number variation, or a combination thereof.

Certain aspects of the invention are especially amenable for implementation using a computer. The computer or CPU is able to compare the data regarding the subject's fertility-associated phenotypic traits to the reference set of data to thereby provide a probability of achieving pregnancy. Such systems generally include a central processing unit (CPU) and storage coupled to the CPU. The storage stores instructions that when executed by the CPU, cause the CPU to accept as input, data that is representative of a plurality of fertility-associated phenotypic traits of a female subject. The executed instructions also cause the computer to provide a probability of achieving pregnancy at a certain point in time using a particular fertility treatment as a result of inputting the subject data into an algorithm trained on a reference set of data gathered from a plurality of women for whom fertility-associated phenotypic traits, fertility-associated medical interventions, and pregnancy outcomes are known.

In certain embodiments, the reference set is stored at a remote location separate from the computer and the computer communicates across a network to access the reference set in order to make the determination. In other embodiments, the reference set is stored locally within the computer and the computer accesses the reference set within the computer in order to make the determination.

BRIEF DESCRIPTION OF THE DRAWINGS

FIG. 6 is a listing of the fertility-associated phenotypic traits considered in an IVF study using methods of the present invention.

FIG. 7 is a listing of the fertility-associated phenotypic traits considered in a study of non-ART fertility treatments using methods of the present invention.

DETAILED DESCRIPTION

Figure 1:
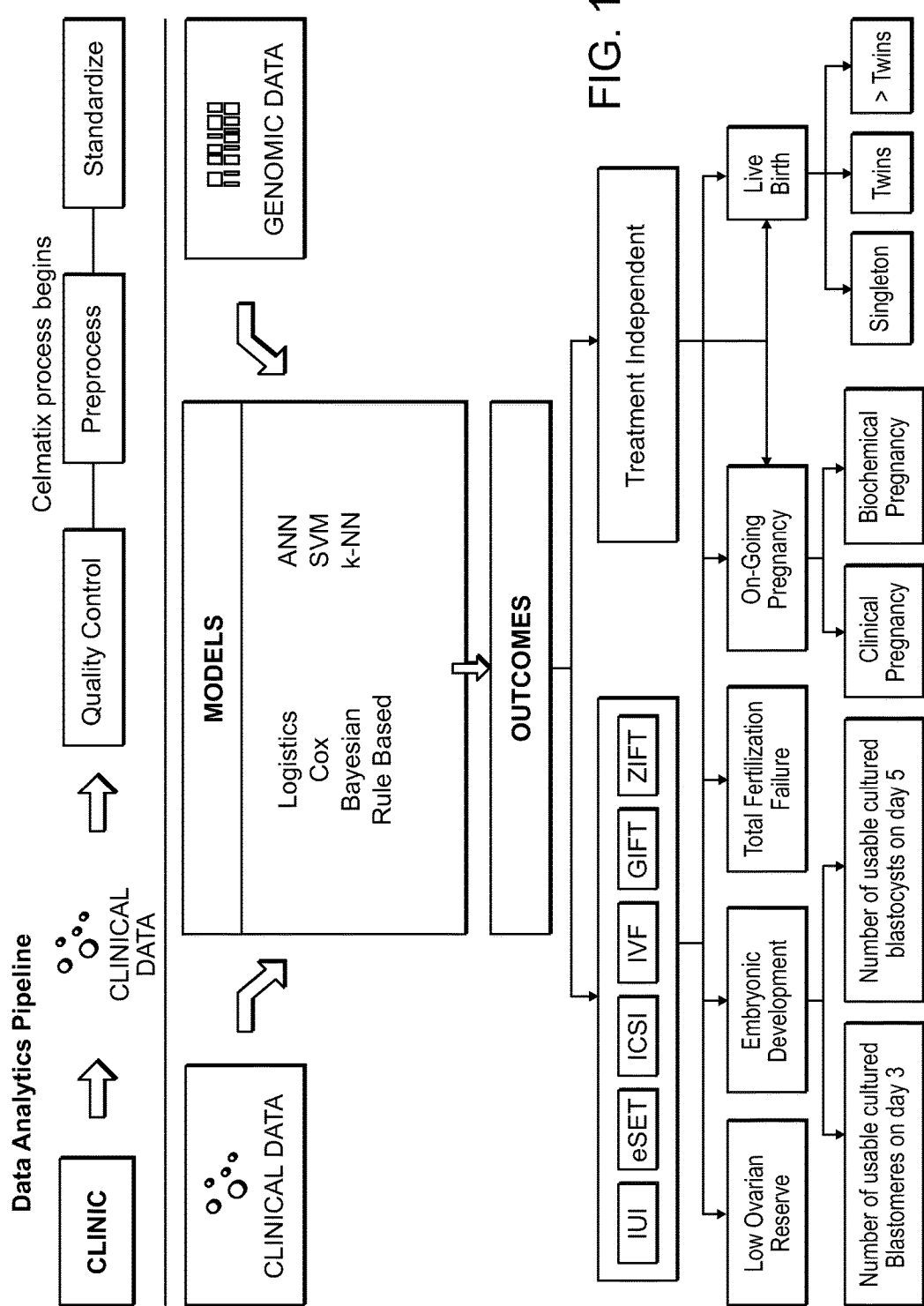
FIG. 1 depicts the data analytics pipeline used to predict outcomes for various fertility treatment protocols.

The present invention generally relates to systems and methods for determining the probability of achieving pregnancy at a selected point in time using a particular fertility treatment. Systems and methods of the invention are useful with all types of fertility treatments reproductive technologies, and are particularly useful with in vitro fertilization (IVF). In addition, it is to be understood that the invention is equally applicable to the determination of a pregnancy that results in a live birth.

Certain aspects of the invention are especially amenable for implementation using a computer. In those embodiments, systems and methods of the invention encompass a central processing unit (CPU) and storage coupled to the CPU. The storage stores instructions that when executed by the CPU, cause the CPU to accept as input data that is representative of a plurality of fertility-associated phenotypic traits of a female subject. The executed instructions also cause the computer to provide a probability of achieving pregnancy at a selected point in time using a certain fertility treatment as a result of comparing the input data to a reference set of data gathered from a plurality of women for whom fertility-associated phenotypic traits, fertility-associated medical interventions, and pregnancy outcomes are known. Systems and methods of the invention are able to account for any woman from the cohort who ceases attempting to become pregnant prior to reaching a live birth outcome.

Systems and methods of the invention may be used with all types of fertility treatments including assisted reproductive technologies (ART). Suitable assisted reproductive technologies include, without limitation, in vitro fertilization (IVF), zygote intrafallopian transfer (ZIFT), gametic intrafallopian transfer (GIFT), or intracytoplasmic sperm injection (ICSI) paired with one of the methods above, and non-ART fertility treatments (RE) include ovulation induction protocols with drugs such as Clomiphene or hormone therapy with or without intrauterine insemination (IUI) with sperm. In IVF, eggs are removed from the female subject, fertilized outside the body, and implanted inside the uterus of the female subject. ZIFT is similar to IVF in that eggs are removed and fertilization of the eggs occurs outside the body. In ZIFT, however, the eggs are implanted in the Fallopian tube rather than the uterus. GIFT involves transferring eggs and sperm into the female subject's Fallopian tube. Accordingly, fertilization occurs inside the woman's body. In ICSI, a single sperm is injected into a mature egg that has removed from the body. The embryo is then transferred to the uterus or Fallopian tube. In RE, hormone stimulation is used to improve the woman's fertility. In general, these fertility-associated medical interventions are not simply a one-time treatment but often require multiple rounds or cycles of treatment. Therefore, systems and methods of the invention encompass determining the likelihood of achieving pregnancy at a selected point in time, for example, a selected cycle of treatment.

The disclosed methods are also suitable when the female subject interested in having a child is not the one who will carry the baby. For example, if a surrogate is used, a couple may wish to know the likelihood that the surrogate can carry the embryo to live birth. Potential surrogates can include traditional and gestational surrogates. With a traditional surrogate, pregnancy may be achieved through insemination alone or through the assisted reproductive technologies described above, and the surrogate will be biologically related to the child. With a gestational carrier, eggs are removed from the female subject, fertilized with her partner's sperm, and transferred to the uterus of the gestational carrier. The gestational carrier will not be genetically related to the child. Whatever type of surrogate is used, the disclosed methods can also be applied to the surrogate as a secondary female subject.

FIG. 1 depicts the data analytics pipeline used to predict outcomes for various fertility treatment protocols. In order to determine the probability of pregnancy for a female subject as a result of the chosen reproductive technology, aspects of the invention include obtaining information regarding the subject's fertility-associated phenotypic traits. Exemplary traits are provided in Table 1 below.

TABLE 1

| Phenotypic and environmental variables impacting fertility success |
| --- |
| Cholesterol levels on different days of the menstrual cycle |
| Age of first menses for patient and female blood relatives (e.g. sisters, mother, grandmothers) |
| Age of menopause for female blood relatives (e.g. sisters, mother, grandmothers) |
| Number of previous pregnancies (biochemical/ectopic/clinical/fetal heart beat detected, live birth outcomes), age at the time, and outcome for patient and female blood relatives (e.g. sisters, mother, grandmothers) |
| Diagnosis of Polycystic Ovarian Syndrome |
| History of hydrosalpinx or tubal occlusion |
| History of endometriosis, pelvic pain, or painful periods |
| Cancer history/type of cancer/treatment/outcome for patient and female blood relatives (e.g. sisters, mother, grandmothers) |
| Age that sexual activity began, current level of sexual activity |
| Smoking history for patient and blood relatives |
| Travel schedule/number of flying hours a year/time difference changes of more than 3 hours (Jetlag and Flight-associated Radiation Exposure) |
| Nature of periods (length of menses, length of cycle) |
| Biological age (number of years since first menses) |

TABLE 1-continued

Phenotypic and environmental variables impacting fertility success

Birth control use
Drug use (illegal or legal)
Body mass index (current, lowest ever, highest ever)
History of polyps
History of hormonal imbalance
History of amenorrhoea
History of eating disorders
Alcohol consumption by patient or blood relatives
Details of mother's pregnancy with patient (i.e. measures of uterine environment): any drugs taken, smoking, alcohol, stress levels, exposure to plastics (i.e. Tupperware), composition of diet (see below)
Sleep patterns: number of hours a night, continuous/overall
Diet: meat, organic produce, vegetables, vitamin or other supplement consumption, dairy (full fat or reduced fat), coffee/tea consumption, folic acid, sugar (complex, artificial, simple), processed food versus home cooked.
Exposure to plastics: microwave in plastic, cook with plastic, store food in plastic, plastic water or coffee mugs.
Water consumption: amount per day, format: straight from the tap, bottled water (plastic or bottle), filtered (type: e.g. Britta/Pur)
Residence history starting with mother's pregnancy: location/duration
Environmental exposure to potential toxins for different regions (extracted from government monitoring databases)
Health metrics: autoimmune disease, chronic illness/condition
Pelvic surgery history
Life time number of pelvic X-rays
History of sexually transmitted infections: type/treatment/outcome
Reproductive hormone levels: follicle stimulating hormone, anti-Müllerian hormone, estrogen, progesterone
Stress
Thickness and type of endometrium throughout the menstrual cycle.
Age
Height
Fertility treatment history and details: history of hormone stimulation, brand of drugs used, basal antral follicle count, follicle count after stimulation with different protocols, number/quality/stage of retrieved oocytes/development profile of embryos resulting from in vitro insemination (natural or ICSI), details of IVF procedure (which clinic, doctor/embryologist at clinic, assisted hatching, fresh or thawed oocytes/embryos, embryo transfer (blood on the catheter/squirt detection and direction on ultrasound), number of successful and unsuccessful IVF attempts
Morning sickness during pregnancy
Breast size before/during/after pregnancy
History of ovarian cysts
Twin or sibling from multiple birth (mono-zygotic or di-zygotic)
Male factor infertility for reproductive partner: Semen analysis (count, motility, morphology), Vasectomy, male cancer, smoking, alcohol, diet, STIs
Blood type
DES exposure in utero
Past and current exercise/athletic history
Levels of phthalates, including metabolites:
MEP - monoethyl phthalate, MECPP - mono(2-ethyl-5-carboxypentyl) phthalate, MEHHP - mono(2-ethyl-5-hydroxyhexyl) phthalate, MEOHP - mono(2-ethyl-5-oxohexyl) phthalate, MBP - monobutyl phthalate, MBzP - monobenzyl phthalate, MEHP - mono(2-ethylhexyl) phthalate, MiBP - mono-isobutyl phthalate, MCPP - mono(3-carboxypropyl) phthalate, MCOP - monocarboxyisooctyl phthalate, MCNP - monocarboxyisononyl phthalate
Familial history of Premature Ovarian Failure/Insufficiency
Autoimmunity history - Antiadrenal antibodies (anti-21-hydroxylase antibodies), antiovarian antibodies, antithyroid anitibodies (anti-thyroid peroxidase, antithyroglobulin)
Hormone levels: Leutenizing hormone (using immunofluorometric assay), $\Delta 4$-Androstenedione (using radioimmunoassay), Dehydroepiandrosterone (using radioimmunoassay), and Inhibin B (commercial ELISA)
Number of years trying to conceive
Dioxin and PVC exposure
Hair color
Nevi (moles)
Lead, cadmium, and other heavy metal exposure
For a particular ART cycle: the percentage of eggs that were abnormally fertilized, if assisted hatching was performed, if anesthesia was used, average number of cells contained by the embryo at the time of cryopreservation, average degree of expansion for blastocyst represented as a score, average degree of expansion of a previously frozen embryo represented as a score, embryo quality metrics including but not limited to degree
of cell fragmentation and visualization of a or organization/number of cells contained in the inner cell mass (ICM), the fraction of overall embryos that make it to the blastocyst stage of development, the number of embryos that make it to the blastocyst stage of development, use of birth control, the brand name of the hormones used in ovulation induction, hyperstimulation syndrome, reason for cancelation of a treatment cycle,

TABLE 1-continued

Phenotypic and environmental variables impacting fertility success chemical pregnancy detected, clinical pregnancy detected, count of germinal vesicle containing oocytes upon retrieval, count of metaphase I stage eggs upon retrieval, count of metaphase II stage eggs upon retrieval, count of embryos or oocytes arrested in development and the stage of development or day of development post oocyte retrieval, number of embryos transferred and date in days post-oocyte retrieval that the embryos were transferred, how many embryos were cryopreserved and at what stage of development Information regarding the fertility-associated phenotypic traits of the female, such as those listed in Table 1, can be obtained by any means known in the art. In many cases, such information can be obtained from a questionnaire completed by the subject that contains questions regarding certain fertility-associated phenotypic traits. Additional information can be obtained from a questionnaire completed by the subject's partner and blood relatives. The questionnaire includes questions regarding the subject's fertility-associated phenotypic traits, such as her age, smoking habits, or frequency of alcohol consumption. Information can also be obtained from the medical history of the subject, as well as the medical history of blood relatives and other family members. Additional information can be obtained from the medical history and family medical history of the subject's partner. Medical history information can be obtained through analysis of electronic medical records, paper medical records, a series of questions about medical history included in the questionnaire, and a combination thereof.

Clinical Samples

In other embodiments, information useful for determining the likelihood of pregnancy is obtained by analyzing a sample collected from the female subject, reproductive partners of the subject, blood relatives of the subject, gamete or embryo donors involved in the pregnancy effort, pregnancy surrogates, and a combination thereof. The sample may include a human tissue or bodily fluid and may be collected in any clinically acceptable manner. A tissue is a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue, e.g. an endometrial aspirate, breast tissue biopsy, and the like. A sample also may be media containing cells or biological material. A sample may also be a blood clot, for example, a blood clot that has been obtained from whole blood after the serum has been removed. In certain embodiments, the sample may include reproductive cells or tissues, such as gametic cells, gonadal tissue, fertilized embryos, and placenta. In certain embodiments, the sample is blood or saliva collected from the female subject.

In other embodiments, an assay specific to an environmental exposure is used to obtain the phenotypic trait of interest. Such assays are known to those of skill in the art, and may be used with methods of the invention. For example, the hormones used in birth control pills (estrogen and progesterone) may be detected from a urine or blood test. Venners et al. (Hum. Reprod. 21(9): 2272-2280, 2006) reports assays for detecting estrogen and progesterone in urine and blood samples. Venner also reports assays for detecting the chemicals used in fertility treatments.

Similarly, illicit drug use may be detected from a tissue or body fluid, such as hair, urine sweat, or blood, and there are numerous commercially available assays (LabCorp) for conducting such tests. Standard drug tests look for ten different classes of drugs, and the test is commercially known as a "10-panel urine screen". The 10-panel urine screen consists of the following: 1. Amphetamines (including Methamphetamine) 2. Barbiturates 3. Benzodiazepines 4. Cannabinoids (THC) 5. Cocaine 6. Methadone 7. Methaqualone 8. Opiates (Codeine, Morphine, Heroin, Oxycodone, Vicodin, etc.) 9. Phencyclidine (PCP) 10. Propoxyphene. Use of alcohol can also be detected by such tests.

Numerous assays can be used to tests a patient's exposure to plastics (e.g., Bisphenol A (BPA)). BPA is most commonly found as a component of polycarbonates (about 74% of total BPA produced) and in the production of epoxy resins (about 20%). As well as being found in a myriad of products including plastic food and beverage contains (including baby and water bottles), BPA is also commonly found in various household appliances, electronics, sports safety equipment, adhesives, cash register receipts, medical devices, eyeglass lenses, water supply pipes, and many other products. Assays for testing blood, sweat, or urine for presence of BPA are described, for example, in Genuis et al. (Journal of Environmental and Public Health, Volume 2012, Article ID 185731, 10 pages, 2012).

Genotypic information from the sample can be obtained by nucleic acid extraction from the sample. Methods for extracting nucleic acid from a sample are known in the art. See for example, Maniatis, et al., Molecular Cloning: A Laboratory Manual, Cold Spring Harbor, N.Y., pp. 280-281, 1982, the contents of which are incorporated by reference herein in their entirety. In certain embodiments, a sample is collected from a subject followed by enrichment for genes or gene fragments of interest, for example by hybridization to a nucleotide array including fertility-related genetic regions or genetic fragments of interest. The sample may be enriched for genetic regions of interest (e.g., infertility-associated genetic regions) using methods known in the art, such as hybrid capture. See for examples, Lapidus (U.S. Pat. No. 7,666,593), the content of which is incorporated by reference herein in its entirety.

RNA may be isolated from eukaryotic cells by procedures that involve lysis of the cells and denaturation of the proteins contained therein. Tissue of interest includes gametic cells, gonadal tissue, endometrial tissue, fertilized embryos, and placenta. Fluids of interest include blood, menstrual fluid, mammary fluid, follicular fluid of the ovary, peritoneal fluid, or culture medium. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+ RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex™ (see Ausubel et al., CURRENT PROTOCOLS IN MOLECULAR BIOLOGY, vol. 2, Current Protocols Publishing, New York (1994). Once bound, poly(A)+ mRNA is eluted from the affinity column using 2 mM EDTA/0.1% SDS.

Biomarkers

In certain aspects of the invention, genotypic data is obtained from the collected sample. It is known that certain genetic regions are associated with infertility. Variations in these genetic regions may affect pregnancy outcomes; therefore, it may be necessary to collect genotype data from the female subject A biomarker generally refers to a molecule that may act as an indicator of a biological state. Biomarkers for use with methods of the invention may be any marker that is associated with infertility. Exemplary biomarkers include genes (e.g. any region of DNA encoding a functional product), genetic regions (e.g. regions including genes and intergenic regions with a particular focus on regions conserved throughout evolution in placental mammals), and gene products (e.g., RNA and protein). In certain embodiments, the biomarker is an infertility-associated genetic region. An infertility-associated genetic region is any DNA sequence in which variation is associated with a change in fertility. Examples of changes in fertility include, but are not limited to, the following: a homozygous mutation of an infertility-associated gene leads to a complete loss of fertility; a homozygous mutation of an infertility-associated gene is incompletely penetrant and leads to reduction in fertility that varies from individual to individual; a heterozygous mutation is completely recessive, having no effect on fertility; and the infertility-associated gene is X-linked, such that a potential defect in fertility depends on whether a non-functional allele of the gene is located on an inactive X chromosome (Ban body) or on an expressed X chromosome.

In particular embodiments, the assessed infertility-associated genetic region is a maternal effect gene. Maternal effects genes are genes that have been found to encode key structures and functions in mammalian oocytes (Yurttas et al., Reproduction 139:809-823, 2010). Maternal effect genes are described, for example in, Christians et al. (Mol Cell Biol 17:778-88, 1997); Christians et al., Nature 407:693-694, 2000); Xiao et al. (EMBO J 18:5943-5952, 1999); Tong et al. (Endocrinology 145:1427-1434, 2004); Tong et al. (Nat Genet 26:267-268, 2000); Tong et al. (Endocrinology, 140:3720-3726, 1999); Tong et al. (Hum Reprod 17:903-911, 2002); Ohsugi et al. (Development 135:259-269, 2008); Borowczyk et al. (Proc Natl Acad Sci USA., 2009); and Wu (Hum Reprod 24:415-424, 2009). Maternal effects genes are also described in U.S. Ser. No. 12/889,304. The content of each of these is incorporated by reference herein in its entirety.

In particular embodiments, the infertility-associated genetic region is a gene (including exons, introns, and 10 kb of DNA flanking either side of said gene) selected from the genes shown in Table 1 below. In Table 1, OMIM reference numbers are provided when available

TABLE 2

Human Infertility-Related Genes (OMIM #)

| | | | |
|---|---|---|---|
| ABCA1 (600046) | ACTL6A (604958) | ACTL8 | ACVR1 (102576) |
| ACVR1B (601300) | ACVR1C (608981) | ACVR2 (102581) | ACVR2A (102581) |
| ACVR2B (602730) | ACVRL1 (601284) | ADA (608958) | ADAMTS1 (605174) |
| ADM (103275) | ADM2 (608682) | AFF2 (300806) | AGT (106150) |
| AHR (600253) | AIRE (607358) | AK2 (103020) | AK7 |
| AKR1C1 (600449) | AKR1C2 (600450) | AKR1C3 (603966) | AKR1C4 (600451) |
| AKT1 (164730) | ALDOA (103850) | ALDOB (612724) | ALDOC (103870) |
| ALPL (171760) | AMBP (176870) | AMD1 (180980) | AMH (600957) |
| AMHR2 (600956) | ANK3 (600465) | ANXA1 (151690) | APC (611731) |
| APOA1 (107680) | APOE (107741) | AQP4 (600308) | AR (313700) |
| AREG (104640) | ARF1 (103180) | ARF3 (103190) | ARF4 (601177) |
| ARF5 (103188) | ARFRP1 (604699) | ARL1 (603425) | ARL10 (612405) |
| ARL11 (609351) | ARL13A | ARL13B (608922) | ARL15 |
| ARL2 (601175) | ARL3 (604695) | ARL4A (604786) | ARL4C (604787) |
| ARL4D (600732) | ARL5A (608960) | ARL5B (608909) | ARL5C |
| ARL6 (608845) | ARL8A | ARL8B | ARMC2 |
| ARNTL (602550) | ASCL2 (601886) | ATF7IP (613644) | ATG7 (608760) |
| ATM (607585) | ATR (601215) | ATXN2 (601517) | AURKA (603072) |
| AURKB (604970) | AUTS2 (607270) | BARD1 (601593) | BAX (600040) |
| BBS1 (209901) | BBS10 (610148) | BBS12 (610683) | BBS2 (606151) |
| BBS4 (600374) | BBS5 (603650) | BBS7 (607590) | BBS9 (607968) |
| BCL2 (151430) | BCL2L1 (600039) | BCL2L10 (606910) | BDNF (113505) |
| BECN1 (604378) | BHMT (602888) | BLVRB (600941) | BMP15 (300247) |
| BMP2 (112261) | BMP3 (112263) | BMP4 (112262) | BMP5 (112265) |
| BMP6 (112266) | BMP7 (112267) | BMPR1A (601299) | BMPR1B (603248) |

TABLE 2-continued

| Human Infertility-Related Genes (OMIM #) | | | |
|---|---|---|---|
| BMPR2 (600799) | BNC1 (601930) | BOP1 (610596) | BRCA1 (113705) |
| BRCA2 (600185) | BRIP1 (605882) | BRSK1 (609235) | BRWD1 |
| BSG (109480) | BTG4 (605673) | BUB1 (602452) | BUB1B (602860) |
| C2orf86 (613580) | C3 (120700) | C3orf56 | C6orf221 (611687) |
| CA1 (114800) | CARD8 (609051) | CARM1 (603934) | CASP1 (147678) |
| CASP2 (600639) | CASP5 (602665) | CASP6 (601532) | CASP8 (601763) |
| CBS (613381) | CBX1 (604511) | CBX2 (602770) | CBX5 (604478) |
| CCDC101 (613374) | CCDC28B (610162) | CCL13 (601391) | CCL14 (601392) |
| CCL4 (182284) | CCL5 (187011) | CCL8 (602283) | CCND1 (168461) |
| CCND2 (123833) | CCND3 (123834) | CCNH (601953) | CCS (603864) |
| CD19 (107265) | CD24 (600074) | CD55 (125240) | CD81 (186845) |
| CD9 (143030) | CDC42 (116952) | CDK4 (123829) | CDK6 (603368) |
| CDK7 (601955) | CDKN1B (600778) | CDKN1C (600856) | CDKN2A (600160) |
| CDX2 (600297) | CDX4 (300025) | CEACAM20 | CEBPA (116897) |
| CEBPB (189965) | CEBPD (116898) | CEBPE (600749) | CEBPG (138972) |
| CEBPZ (612828) | CELF1 (601074) | CELF4 (612679) | CENPB (117140) |
| CENPF (600236) | CENPI (300065) | CEP290 (610142) | CFC1 (605194) |
| CGA (118850) | CGB (118860) | CGB1 (608823) | CGB2 (608824) |
| CGB5 (608825) | CHD7 (608892) | CHST2 (603798) | CLDN3 (602910) |
| COIL (600272) | COL1A2 (120160) | COL4A3BP (604677) | COMT (116790) |
| COPE (606942) | COX2 (600262) | CP (117700) | CPEB1 (607342) |
| CRHR1 (122561) | CRYBB2 (123620) | CSF1 (120420) | CSF2 (138960) |
| CSTF1 (600369) | CSTF2 (600368) | CTCF (604167) | CTCFL (607022) |
| CTF2P | CTGF (121009) | CTH (607657) | CTNNB1 (116806) |
| CUL1 (603134) | CX3CL1 (601880) | CXCL10 (147310) | CXCL9 (601704) |
| CXorf67 | CYP11A1 (118485) | CYP11B1 (610613) | CYP11B2 (124080) |
| CYP17A1 (609300) | CYP19A1 (107910) | CYP1A1 (108330) | CYP27B1 (609506) |
| DAZ2 (400026) | DAZL (601486) | DCTPP1 | DDIT3 (126337) |
| DDX11 (601150) | DDX20 (606168) | DDX3X (300160) | DDX43 (606286) |
| DEPDC7 (612294) | DHFR (126060) | DHFRL1 | DIAPH2 (300108) |
| DICER1 (606241) | DKK1 (605189) | DLC1 (604258) | DLGAP5 |
| DMAP1 (605077) | DMC1 (602721) | DNAJB1 (604572) | DNMT1 (126375) |
| DNMT3B (602900) | DPPA3 (608408) | DPPA5 (611111) | DPYD (612779) |
| DTNBP1 (607145) | DYNLL1 (601562) | ECHS1 (602292) | EEF1A1 (130590) |
| EEF1A2 (602959) | EFNA1 (191164) | EFNA2 (602756) | EFNA3 (601381) |
| EFNA4 (601380) | EFNA5 (601535) | EFNB1 (300035) | EFNB2 (600527) |
| EFNB3 (602297) | EGR1 (128990) | EGR2 (129010) | EGR3 (602419) |
| EGR4 (128992) | EHMT1 (607001) | EHMT2 (604599) | EIF2B2 (606454) |
| EIF2B4 (606687) | EIF2B5 (603945) | EIF2C2 (606229) | EIF3C (603916) |
| EIF3CL (603916) | EPHA1 (179610) | EPHA10 (611123) | EPHA2 (176946) |
| EPHA3 (179611) | EPHA4 (602188) | EPHA5 (600004) | EPHA6 (600066) |
| EPHA7 (602190) | EPHA8 (176945) | EPHB1 (600600) | EPHB2 (600997) |
| EPHB3 (601839) | EPHB4 (600011) | EPHB6 (602757) | ERCC1 (126380) |
| ERCC2 (126340) | EREG (602061) | ESR1 (133430) | ESR2 (601663) |
| ESR2 (601663) | ESRRB (602167) | ETV5 (601600) | EZH2 (601573) |
| EZR (123900) | FANCC (613899) | FANCG (602956) | FANCL (608111) |
| FAR1 | FAR2 | FASLG (134638) | FBN1 (134797) |
| FBN2 (612570) | FBN3 (608529) | FBRS (608601) | FBRSL1 |
| FBXO10 (609092) | FBXO11 (607871) | FCRL3 (606510) | FDXR (103270) |
| FGF23 (605380) | FGF8 (600483) | FGFBP1 (607737) | FGFBP3 |
| FGFR1 (136350) | FHL2 (602633) | FIGLA (608697) | FILIP1L (612993) |
| FKBP4 (600611) | FMN2 (606373) | FMR1 (309550) | FOLR1 (136430) |
| FOLR2 (136425) | FOXE1 (602617) | FOXL2 (605597) | FOXN1 (600838) |
| FOXO3 (602681) | FOXP3 (300292) | FRZB (605083) | FSHB (136530) |
| FSHR (136435) | FST (136470) | GALT (606999) | GBP5 (611467) |
| GCK (138079) | GDF1 (602880) | GDF3 (606522) | GDF9 (601918) |
| GGT1 (612346) | GJA1 (121014) | GJA10 (611924) | GJA3 (121015) |
| GJA4 (121012) | GJA5 (121013) | GJA8 (600897) | GJB1 (304040) |
| GJB2 (121011) | GJB3 (603324) | GJB4 (605425) | GJB6 (604418) |
| GJB7 (611921) | GJC1 (608655) | GJC2 (608803) | GJC3 (611925) |
| GJD2 (607058) | GJD3 (607425) | GJD4 (611922) | GNA13 (604406) |
| GNB2 (139390) | GNRH1 (152760) | GNRH2 (602352) | GNRHR (138850) |
| GPC3 (300037) | GPRC5A (604138) | GPRC5B (605948) | GREM2 (608832) |
| GRN (138945) | GSPT1 (139259) | GSTA1 (138359) | H19 (103280) |
| H1FOO (142709) | HABP2 (603924) | HADHA (600890) | HAND2 (602407) |
| HBA1 (141800) | HBA2 (141850) | HBB (141900) | HELLS (603946) |
| HK3 (142570) | HMOX1 (141250) | HNRNPK (600712) | HOXA11 (142958) |
| HPGD (601688) | HS6ST1 (604846) | HSD17B1 (109684) | HSD17B12 (609574) |
| HSD17B2 (109685) | HSD17B4 (601860) | HSD17B7 (606756) | HSD3B1 (109715) |
| HSF1 (140580) | HSF2BP (604554) | HSP90B1 (191175) | HSPG2 (142461) |
| HTATIP2 (605628) | ICAM1 (147840) | ICAM2 (146630) | ICAM3 (146631) |
| IDH1 (147700) | IFI30 (604664) | IFITM1 (604456) | IGF1 (147440) |
| IGF1R (147370) | IGF2 (147470) | IGF2BP1 (608288) | IGF2BP2 (608289) |
| IGF2BP3 (608259) | IGF2BP3 (608259) | IGF2R (147280) | IGFALS (601489) |
| IGFBP1 (146730) | IGFBP2 (146731) | IGFBP3 (146732) | IGFBP4 (146733) |
| IGFBP5 (146734) | IGFBP6 (146735) | IGFBP7 (602867) | IGFBPL1 (610413) |
| IL10 (124092) | IL11RA (600939) | IL12A (161560) | IL12B (161561) |
| IL13 (147683) | IL17A (603149) | IL17B (604627) | IL17C (604628) |

TABLE 2-continued

Human Infertility-Related Genes (OMIM #)

| | | | |
|---|---|---|---|
| IL17D (607587) | IL17F (606496) | IL1A (147760) | IL1B (147720) |
| IL23A (605580) | IL23R (607562) | IL4 (147780) | IL5 (147850) |
| IL5RA (147851) | IL6 (147620) | IL6ST (600694) | IL8 (146930) |
| ILK (602366) | INHA (147380) | INHBA (147290) | INHBB (147390) |
| IRF1 (147575) | ISG15 (147571) | ITGA11 (604789) | ITGA2 (192974) |
| ITGA3 (605025) | ITGA4 (192975) | ITGA7 (600536) | ITGA9 (603963) |
| ITGAV (193210) | ITGB1 (135630) | JAG1 (601920) | JAG2 (602570) |
| JARID2 (601594) | JMY (604279) | KAL1 (300836) | KDM1A (609132) |
| KDM1B (613081) | KDM3A (611512) | KDM4A (609764) | KDM5A (180202) |
| KDM5B (605393) | KHDC1 (611688) | KIAA0430 (614593) | KIF2C (604538) |
| KISS1 (603286) | KISS1R (604161) | KITLG (184745) | KL (604824) |
| KLF4 (602253) | KLF9 (602902) | KLHL7 (611119) | LAMC1 (150290) |
| LAMC2 (150292) | LAMP1 (153330) | LAMP2 (309060) | LAMP3 (605883) |
| LDB3 (605906) | LEP (164160) | LEPR (601007) | LFNG (602576) |
| LHB (152780) | LHCGR (152790) | LHX8 (604425) | LIF (159540) |
| LIFR (151443) | LIMS1 (602567) | LIMS2 (607908) | LIMS3 |
| LIMS3L | LIN28 (611043) | LIN28B (611044) | LMNA (150330) |
| LOC613037 | LOXL4 (607318) | LPP (600700) | LYRM1 (614709) |
| MAD1L1 (602686) | MAD2L1 (601467) | MAD2L1BP | MAF (177075) |
| MAP3K1 (600982) | MAP3K2 (609487) | MAPK1 (176948) | MAPK3 (601795) |
| MAPK8 (601158) | MAPK9 (602896) | MB21D1 (613973) | MBD1 (156535) |
| MBD2 (603547) | MBD3 (603573) | MBD4 (603574) | MCL1 (159552) |
| MCM8 (608187) | MDK (162096) | MDM2 (164785) | MDM4 (602704) |
| MECP2 (300005) | MED12 (300188) | MERTK (604705) | METTL3 (612472) |
| MGAT1 (160995) | MITF (156845) | MKKS (604896) | MKS1 (609883) |
| MLH1 (120436) | MLH3 (604395) | MOS (190060) | MPPED2 (600911) |
| MRS2 | MSH2 (609309) | MSH3 (600887) | MSH4 (602105) |
| MSH5 (603382) | MSH6 (600678) | MST1 (142408) | MSX1 (142983) |
| MSX2 (123101) | MTA2 (603947) | MTHFD1 (172460) | MTHFR (607093) |
| MTO1 (614667) | MTOR (601231) | MTRR (602568) | MUC4 (158372) |
| MVP (605088) | MX1 (147150) | MYC (190080) | NAB1 (600800) |
| NAB2 (602381) | NAT1 (108345) | NCAM1 (116930) | NCOA2 (601993) |
| NCOR1 (600849) | NCOR2 (600848) | NDP (300658) | NFE2L3 (604135) |
| NLRP1 (606636) | NLRP10 (609662) | NLRP11 (609664) | NLRP12 (609648) |
| NLRP13 (609660) | NLRP14 (609665) | NLRP2 (609364) | NLRP3 (606416) |
| NLRP4 (609645) | NLRP5 (609658) | NLRP6 (609650) | NLRP7 (609661) |
| NLRP8 (609659) | NLRP9 (609663) | NNMT (600008) | NOBOX (610934) |
| NODAL (601265) | NOG (602991) | NOS3 (163729) | NOTCH1 (190198) |
| NOTCH2 (600275) | NPM2 (608073) | NPR2 (108961) | NR2C2 (601426) |
| NR3C1 (138040) | NR5A1 (184757) | NR5A2 (604453) | NRIP1 (602490) |
| NRIP2 | NRIP3 (613125) | NTF4 (162662) | NTRK1 (191315) |
| NTRK2 (600456) | NUPR1 (614812) | OAS1 (164350) | OAT (613349) |
| OFD1 (300170) | OOEP (611689) | ORAI1 (610277) | OTC (300461) |
| PADI1 (607934) | PADI2 (607935) | PADI3 (606755) | PADI4 (605347) |
| PADI6 (610363) | PAEP (173310) | PAIP1 (605184) | PARP12 (612481) |
| PCNA (176740) | PCP4L1 | PDE3A (123805) | PDK1 (602524) |
| PGK1 (311800) | PGR (607311) | PGRMC1 (300435) | PGRMC2 (607735) |
| PIGA (311770) | PIM1 (164960) | PLA2G2A (172411) | PLA2G4C (603602) |
| PLA2G7 (601690) | PLAC1L | PLAG1 (603026) | PLAGL1 (603044) |
| PLCB1 (607120) | PMS1 (600258) | PMS2 (600259) | POF1B (300603) |
| POLG (174763) | POLR3A (614258) | POMZP3 (600587) | POU5F1 (164177) |
| PPID (601753) | PPP2CB (176916) | PRDM1 (603423) | PRDM9 (609760) |
| PRKCA (176960) | PRKCB (176970) | PRKCD (176977) | PRKCDBP |
| PRKCE (176975) | PRKCG (176980) | PRKCQ (600448) | PRKRA (603424) |
| PRLR (176761) | PRMT1 (602950) | PRMT10 (307150) | PRMT2 (601961) |
| PRMT3 (603190) | PRMT5 (604045) | PRMT6 (608274) | PRMT7 (610087) |
| PRMT8 (610086) | PROK1 (606233) | PROK2 (607002) | PROKR1 (607122) |
| PROKR2 (607123) | PSEN1 (104311) | PSEN2 (600759) | PTGDR (604687) |
| PTGER1 (176802) | PTGER2 (176804) | PTGER3 (176806) | PTGER4 (601586) |
| PTGES (605172) | PTGES2 (608152) | PTGES3 (607061) | PTGFR (600563) |
| PTGFRN (601204) | PTGS1 (176805) | PTGS2 (600262) | PTN (162095) |
| PTX3 (602492) | QDPR (612676) | RAD17 (603139) | RAX (601881) |
| RBP4 (180250) | RCOR1 (607675) | RCOR2 | RCOR3 |
| RDH11 (607849) | REC8 (608193) | REXO1 (609614) | REXO2 (607149) |
| RFPL4A (612601) | RGS2 (600861) | RGS3 (602189) | RSPO1 (609595) |
| RTEL1 (608833) | SAFB (602895) | SAR1A (607691) | SAR1B (607690) |
| SCARB1 (601040) | SDC3 (186357) | SELL (153240) | SEPHS1 (600902) |
| SEPHS2 (606218) | SERPINA10 (605271) | SFRP1 (604156) | SFRP2 (604157) |
| SFRP4 (606570) | SFRP5 (604158) | SGK1 (602958) | SGOL2 (612425) |
| SH2B1 (608937) | SH2B2 (605300) | SH2B3 (605093) | SIRT1 (604479) |
| SIRT2 (604480) | SIRT3 (604481) | SIRT4 (604482) | SIRT5 (604483) |
| SIRT6 (606211) | SIRT7 (606212) | SLC19A1 (600424) | SLC28A1 (606207) |
| SLC28A2 (606208) | SLC28A3 (608269) | SLC2A8 (605245) | SLC6A2 (163970) |
| SLC6A4 (182138) | SLCO2A1 (601460) | SLITRK4 (300562) | SMAD1 (601595) |
| SMAD2 (601366) | SMAD3 (603109) | SMAD4 (600993) | SMAD5 (603110) |
| SMAD6 (602931) | SMAD7 (602932) | SMAD9 (603295) | SMARCA4 (603254) |
| SMARCA5 (603375) | SMC1A (300040) | SMC1B (608685) | SMC3 (606062) |
| SMC4 (605575) | SMPD1 (607608) | SOCS1 (603597) | SOD1 (147450) |

TABLE 2-continued

Human Infertility-Related Genes (OMIM #)

| | | | |
|---|---|---|---|
| SOD2 (147460) | SOD3 (185490) | SOX17 (610928) | SOX3 (313430) |
| SPAG17 | SPARC (182120) | SPIN1 (609936) | SPN (182160) |
| SPO11 (605114) | SPP1 (166490) | SPSB2 (611658) | SPTB (182870) |
| SPTBN1 (182790) | SPTBN4 (606214) | SRCAP (611421) | SRD5A1 (184753) |
| SRSF4 (601940) | SRSF7 (600572) | ST5 (140750) | STAG3 (608489) |
| STAR (600617) | STARD10 | STARD13 (609866) | STARD3 (607048) |
| STARD3NL (611759) | STARD4 (607049) | STARD5 (607050) | STARD6 (607051) |
| STARD7 | STARD8 (300689) | STARD9 (614642) | STAT1 (600555) |
| STAT2 (600556) | STAT3 (102582) | STAT4 (600558) | STAT5A (601511) |
| STAT5B (604260) | STAT6 (601512) | STC1 (601185) | STIM1 (605921) |
| STK3 (605030) | SULT1E1 (600043) | SUZ12 (606245) | SYCE1 (611486) |
| SYCE2 (611487) | SYCP1 (602162) | SYCP2 (604105) | SYCP3 (604759) |
| SYNE1 (608441) | SYNE2 (608442) | TAC3 (162330) | TACC3 (605303) |
| TACR3 (162332) | TAF10 (600475) | TAF3 (606576) | TAF4 (601796) |
| TAF4B (601689) | TAF5 (601787) | TAF5L | TAF8 (609514) |
| TAF9 (600822) | TAP1 (170260) | TBL1X (300196) | TBXA2R (188070) |
| TCL1A (186960) | TCL1B (603769) | TCL6 (604412) | TCN2 (613441) |
| TDGF1 (187395) | TERC (602322) | TERF1 (600951) | TERT (187270) |
| TEX12 (605791) | TEX9 | TF (190000) | TFAP2C (601602) |
| TFPI (152310) | TFPI2 (600033) | TG (188450) | TGFB1 (190180) |
| TGFB1I1 (602353) | TGFBR3 (600742) | THOC5 (612733) | THSD7B |
| TLE6 (612399) | TM4SF1 (191155) | TMEM67 (609884) | TNF (191160) |
| TNFAIP6 (600410) | TNFSF13B (603969) | TOP2A (126430) | TOP2B (126431) |
| TP53 (191170) | TP53I3 (605171) | TP63 (603273) | TP73 (601990) |
| TPMT (187680) | TPRXL (611167) | TPT1 (600763) | TRIM32 (602290) |
| TSC2 (191092) | TSHB (188540) | TSIX (300181) | TTC8 (608132) |
| TUBB4Q (158900) | TUFM (602389) | TYMS (188350) | UBB (191339) |
| UBC (191340) | UBD (606050) | UBE2D3 (602963) | UBE3A (601623) |
| UBL4A (312070) | UBL4B (611127) | UIMC1 (609433) | UQCR11 (609711) |
| UQCRC2 (191329) | USP9X (300072) | VDR (601769) | VEGFA (192240) |
| VEGFB (601398) | VEGFC (601528) | VHL (608537) | VIM (193060) |
| VKORC1 (608547) | VKORC1L1 (608838) | WAS (300392) | WISP2 (603399) |
| WNT7A (601570) | WNT7B (601967) | WT1 (607102) | XDH (607633) |
| XIST (314670) | YBX1 (154030) | YBX2 (611447) | ZAR1 (607520) |
| ZFX (314980) | ZNF22 (194529) | ZNF267 (604752) | ZNF689 |
| ZNF720 | ZNF787 | ZNF84 | ZP1 (195000) |
| ZP2 (182888) | ZP3 (182889) | ZP4 (613514) | |

The molecular products of the genes in Table 1 are involved in different aspects of oocyte and embryo physiology from transcription and chromosome remodeling to RNA processing and binding. Mutations in these classes of genes result in fertility difficulties for mammals containing these mutations. Exemplary genes that affect fertility are further described below.

Peptidylarginine deiminase 6 (PADI6) Padi6 was originally cloned from a 2D murine egg proteome gel based on its relative abundance, and Padi6 expression in mice appears to be almost entirely limited to the oocyte and pre-implantation embryo (Yurttas et al., 2010). Padi6 is first expressed in primordial oocyte follicles and persists, at the protein level, throughout pre-implantation development to the blastocyst stage (Wright et al., Dev Biol, 256:73-88, 2003). Inactivation of Padi6 leads to female infertility in mice, with the Padi6-null developmental arrest occurring at the two-cell stage (Yurttas et al., 2008).

Nucleoplasmin 2 (NPM2) Nucleoplasmin is another maternal effect gene, and is thought to be phosphorylated during mouse oocyte maturation. NPM2 exhibits a phosphate sensitive increase in mass during oocyte maturation. Increased phosphorylation is retained through the pronuclear stage of development. NPM2 then becomes dephosphorylated at the two-cell stage and remains in this form throughout the rest of pre-implantation development. Further, its expression pattern appears to be restricted to oocytes and early embryos. Immunofluorescence analysis of NPM2 localization shows that NPM2 primarily localizes to the nucleus in mouse oocytes and early embryos. In mice, maternally-derived NPM2 is required for female fertility (Burns et al., 2003).

Brahma-related gene 1 (BRG1) Mammalian SWI/SNF-related chromatin remodeling complexes regulate transcription and are believed to be involved in zygotic genome activation (ZGA). Such complexes are composed of approximately nine subunits, which can be variable depending on cell type and tissue. The BRG1 catalytic subunit exhibits DNA-dependent APTase activity, and the energy derived from ATP hydrolysis alters the conformation and position of nucleosomes. Brg1 is expressed in oocytes and has been shown to be essential in the mouse as null homozygotes do not progress beyond the blastocyst stage (Bultman et al., 2000).

Factor located in oocytes permitting embryonic development (FLOPED/OOEP) The subcortical maternal complex (SCMC) is a poorly characterized murine oocyte structure to which several maternal effect gene products localize (Li et al. Dev Cell 15:416-425, 2008). PADI6, MATER, FILIA, TLE6, and FLOPED have been shown to localize to this complex (Li et al. Dev Cell 15:416-425, 2008; Yurttas et al. Development 135:2627-2636, 2008). This complex is not present in the absence of Floped and Nlrp5, and similar to embryos resulting from Nlrp5-depleted oocytes, embryos resulting from Floped-null oocytes do not progress past the two cell stage of mouse development (Li et al., 2008). FLOPED is a small (19 kD) RNA binding protein that has also been characterized under the name of MOEP19 (Herr et al., Dev Biol 314:300-316, 2008).

KH domain containing 3-like, subcortical maternal complex member (FILIA/KHDC3L) FILIA is another small RNA-binding domain containing maternally inherited murine protein. FILIA was identified and named for its interaction with MATER (Ohsugi et al. Development 135: 259-269, 2008). Like other components of the SCMC, maternal inheritance of the Khdc3 gene product is required for early embryonic development. In mice, loss of Khdc3 results in a developmental arrest of varying severity with a high incidence of aneuploidy due, in part, to improper chromosome alignment during early cleavage divisions (Li et al., 2008). Khdc3 depletion also results in aneuploidy, due to spindle checkpoint assembly (SAC) inactivation, abnormal spindle assembly, and chromosome misalignment (Zheng et al. Proc Natl Acad Sci USA 106:7473-7478, 2009).

Basonuclin (BNCI) Basonuclin is a zinc finger transcription factor that has been studied in mice. It is found expressed in keratinocytes and germ cells (male and female) and regulates rRNA (via polymerase I) and mRNA (via polymerase II) synthesis (Iuchi and Green, 1999; Wang et al., 2006). Depending on the amount by which expression is reduced in oocytes, embryos may not develop beyond the 8-cell stage. In Bsn1 depleted mice, a normal number of oocytes are ovulated even though oocyte development is perturbed, but many of these oocytes cannot go on to yield viable offspring (Ma et al., 2006).

Zygote Arrest 1 (ZAR1) Zar1 is an oocyte-specific maternal effect gene that is known to function at the oocyte to embryo transition in mice. High levels of Zar1 expression are observed in the cytoplasm of murine oocytes, and homozygous-null females are infertile: growing oocytes from Zar1-null females do not progress past the two-cell stage.

In certain embodiments, the gene is a gene that is expressed in an oocyte. Exemplary genes include CTCF, ZFP57, POU5F1, SEBOX, and HDAC1.

In other embodiments, the gene is a gene that is involved in DNA repair pathways, including but not limited to, MLH1, PMS1 and PMS2. In other embodiments, the gene is BRCA1 or BRCA2.

In other embodiments, the biomarker is a gene product (e.g., RNA or protein) of an infertility-associated gene. In particular embodiments, the gene product is a gene product of a maternal effect gene. In other embodiments, the gene product is a product of a gene from Table 2. In certain embodiments, the gene product is a product of a gene that is expressed in an oocyte, such as a product of CTCF, ZFP57, POU5F1, SEBOX, and HDAC1. In other embodiments, the gene product is a product of a gene that is involved in DNA repair pathways, such as a product of MLH1, PMS1, or PMS2. In other embodiments, gene product is a product of BRCA1 or BRCA2.

In other embodiments, the biomarker may be an epigenetic factor, such as methylation patterns (e.g., hypermethylation of CpG islands), genomic localization or post-translational modification of histone proteins, or general post-translational modification of proteins such as acetylation, ubiquitination, phosphorylation, or others.

Assays

Genotype data regarding the above genetic regions can be obtained, for example, by conducting an assay that detects either a mutation in an infertility-associated genetic region or abnormal expression of an infertility-associated genetic region. The presence of certain mutations in those genetic regions or abnormal expression levels of those genetic regions is indicative a fertility outcomes, i.e., whether a pregnancy or live birth is achievable. Exemplary mutations include, but are not limited to, a single nucleotide polymorphism, a deletion, an insertion, an inversion, a genetic rearrangement, a copy number variation, or a combination thereof.

In particular embodiments, the assay is conducted on genetic regions from Table 2 or gene products of genes from Table 2. Detailed descriptions of conventional methods, such as those employed to make and use nucleic acid arrays, amplification primers, hybridization probes, and the like can be found in standard laboratory manuals such as: Genome Analysis: A Laboratory Manual Series (Vols. I-IV), Cold Spring Harbor Laboratory Press; PCR Primer: A Laboratory Manual, Cold Spring Harbor Laboratory Press; and Sambrook, J et al., (2001) Molecular Cloning: A Laboratory Manual, 2nd ed. (Vols. 1-3), Cold Spring Harbor Laboratory Press. Custom nucleic acid arrays are commercially available from, e.g., Affymetrix (Santa Clara, Calif.), Applied Biosystems (Foster City, Calif.), and Agilent Technologies (Santa Clara, Calif.).

Methods of detecting mutations in genetic regions are known in the art. In certain embodiments, a mutation in a single infertility-associated genetic region selected from Table 2 indicates infertility. In other embodiments, the assay is conducted on more than one genetic region from Table 2 (e.g., all of the genes from Table 2), and a mutation in at least two of the genetic regions from Table 2 indicates infertility. In other embodiments, a mutation in at least three of the genetic regions from Table 2 indicates infertility; a mutation in at least four of the genetic regions from Table 2 indicates infertility; a mutation in at least five of the genetic regions from Table 2 indicates infertility; a mutation in at least six of the genetic regions from Table 2 indicates infertility; a mutation in at least seven of the genetic regions from Table 2 indicates infertility; a mutation in at least eight of the genetic regions from Table 2 indicates infertility; a mutation in at least nine of the genetic regions from Table 2 indicates infertility; a mutation in at least 10 of the genetic regions from Table 2 indicates infertility; a mutation in at least 15 of the genetic regions from Table 2 indicates infertility; or a mutation in all of the genetic regions from Table 2 indicates infertility.

In certain embodiments, a known single nucleotide polymorphism at a particular position can be detected by single base extension for a primer that binds to the sample DNA adjacent to that position. See for example Shuber et al. (U.S. Pat. No. 6,566,101), the content of which is incorporated by reference herein in its entirety. In other embodiments, a hybridization probe might be employed that overlaps the SNP of interest and selectively hybridizes to sample nucleic acids containing a particular nucleotide at that position. See for example Shuber et al. (U.S. Pat. Nos. 6,214,558 and 6,300,077), the content of which is incorporated by reference herein in its entirety.

In particular embodiments, nucleic acids are sequenced in order to detect variants (i.e., mutations) in the nucleic acid compared to wild-type and/or non-mutated forms of the sequence. The nucleic acid can include a plurality of nucleic acids derived from a plurality of genetic elements. Methods of detecting sequence variants are known in the art, and sequence variants can be detected by any sequencing method known in the art e.g., ensemble sequencing or single molecule sequencing.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes One conventional method to perform sequencing is by chain termination and gel separation, as described by Sanger et al., Proc Natl. Acad. Sci. USA, 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. See, e.g., Harris et al., (U.S. patent application number 2009/0156412). The content of each reference is incorporated by reference herein in its entirety.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H$^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

If the nucleic acid from the sample is degraded or only a minimal amount of nucleic acid can be obtained from the sample, PCR can be performed on the nucleic acid in order to obtain a sufficient amount of nucleic acid for sequencing (See e.g., Mullis et al. U.S. Pat. No. 4,683,195, the contents of which are incorporated by reference herein in its entirety).

Methods of detecting levels of gene products (e.g., RNA or protein) are known in the art. Commonly used methods known in the art for the quantification of mRNA expression in a sample include northern blotting and in situ hybridization (Parker & Barnes, Methods in Molecular Biology 106:247 283 (1999), the contents of which are incorporated by reference herein in their entirety); RNAse protection assays (Hod, Biotechniques 13:852 854 (1992), the contents of which are incorporated by reference herein in their entirety); and PCR-based methods, such as reverse transcription polymerase chain reaction (RT-PCR) (Weis et al., Trends in Genetics 8:263 264 (1992), the contents of which are incorporated by reference herein in their entirety). Alternatively, antibodies may be employed that can recognize specific duplexes, including RNA duplexes, DNA-RNA hybrid duplexes, or DNA-protein duplexes. Other methods known in the art for measuring gene expression (e.g., RNA or protein amounts) are shown in Yeatman et al. (U.S. patent application number 2006/0195269), the content of which is hereby incorporated by reference in its entirety.

A differentially or abnormally expressed gene refers to a gene whose expression is activated to a higher or lower level in a subject suffering from a disorder, such as infertility, relative to its expression in a normal or control subject. The terms also include genes whose expression is activated to a higher or lower level at different stages of the same disorder. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example.

Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disorder, such as infertility, or between various stages of the same disorder. Differential expression includes both quantitative, as well as qualitative, differences in the temporal or cellular expression pattern in a gene or its expression products. Differential gene expression (increases and decreases in expression) is based upon percent or fold changes over expression in normal cells. Increases may be of 1, 5, 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or 10 fold over expression levels in normal cells. Decreases may be of 1, 5, 10, 20, 30, 40, 50, 55, 60, 65, 70, 75, 80, 82, 84, 86, 88, 90, 92, 94, 96, 98, 99 or 100% relative to expression levels in normal cells.

In certain embodiments, reverse transcriptase PCR (RT-PCR) is used to measure gene expression. RT-PCR is a quantitative method that can be used to compare mRNA levels in different sample populations to characterize patterns of gene expression, to discriminate between closely related mRNAs, and to analyze RNA structure.

The first step is the isolation of mRNA from a target sample. The starting material is typically total RNA isolated from human tissues or fluids.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). The contents of each of these references are incorporated by reference herein in their entirety. In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE Complete DNA and RNA Purification Kit (EPICENTRE, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In certain embodiments, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and actin, beta (ACTB). For performing analysis on pre-implantation embryos and oocytes, conserved helix-loop-helix ubiquitous kinase (CHUK) is a gene that is used for normalization.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, in which internal competitor for each target sequence is used for normalization, and with quantitative comparative PCR using a normalization gene contained within the sample, or a housekeeping gene for RT-PCR. For further details see, e.g. Held et al., Genome Research 6:986 994 (1996), the contents of which are incorporated by reference herein in their entirety.

In another embodiment, a MassARRAY-based gene expression profiling method is used to measure gene expression. In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059 3064 (2003).

Further PCR-based techniques include, for example, differential display (Liang and Pardee, Science 257:967 971 (1992)); amplified fragment length polymorphism (iAFLP)

(Kawamoto et al., Genome Res. 12:1305 1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888 1898 (2001)); and high coverage expression profiling (HiCEP) analysis (Fukumura et al., Nucl. Acids. Res. 31(16) e94 (2003)). The contents of each of which are incorporated by reference herein in their entirety.

In certain embodiments, differential gene expression can also be identified, or confirmed using a microarray technique. In this method, polynucleotide sequences of interest (including cDNAs and oligonucleotides) are plated, or arrayed, on a microchip substrate. The arrayed sequences are then hybridized with specific DNA probes from cells or tissues of interest. Methods for making microarrays and determining gene product expression (e.g., RNA or protein) are shown in Yeatman et al. (U.S. patent application number 2006/0195269), the content of which is incorporated by reference herein in its entirety.

In a specific embodiment of the microarray technique, PCR amplified inserts of cDNA clones are applied to a substrate in a dense array, for example, at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106 149 (1996), the contents of which are incorporated by reference herein in their entirety). Microarray analysis can be performed by commercially available equipment, following manufacturer's protocols, such as by using the Affymetrix GenChip technology, or Incyte's microarray technology.

Alternatively, protein levels can be determined by constructing an antibody microarray in which binding sites comprise immobilized, preferably monoclonal, antibodies specific to a plurality of protein species encoded by the cell genome. Preferably, antibodies are present for a substantial fraction of the proteins of interest. Methods for making monoclonal antibodies are well known (see, e.g., Harlow and Lane, 1988, ANTIBODIES: A LABORATORY MANUAL, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art. Generally, the expression, and the level of expression, of proteins of diagnostic or prognostic interest can be detected through immunohistochemical staining of tissue slices or sections.

Finally, levels of transcripts of marker genes in a number of tissue specimens may be characterized using a "tissue array" (Kononen et al., Nat. Med 4(7):844-7 (1998)). In a tissue array, multiple tissue samples are assessed on the same microarray. The arrays allow in situ detection of RNA and protein levels; consecutive sections allow the analysis of multiple samples simultaneously.

In other embodiments, Serial Analysis of Gene Expression (SAGE) is used to measure gene expression. Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997, the contents of each of which are incorporated by reference herein in their entirety).

In other embodiments Massively Parallel Signature Sequencing (MPSS) is used to measure gene expression. This method, described by Brenner et al., Nature Biotechnology 18:630 634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Immunohistochemistry methods are also suitable for detecting the expression levels of the gene products of the present invention. Thus, antibodies (monoclonal or polyclonal) or antisera, such as polyclonal antisera, specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

In certain embodiments, a proteomics approach is used to measure gene expression. A proteome refers to the totality of the proteins present in a sample (e.g. tissue, organism, or cell culture) at a certain point of time. Proteomics includes, among other things, study of the global changes of protein expression in a sample (also referred to as expression proteomics). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

In some embodiments, mass spectrometry (MS) analysis can be used alone or in combination with other methods (e.g., immunoassays or RNA measuring assays) to determine the presence and/or quantity of the one or more biomarkers disclosed herein in a biological sample. In some embodiments, the MS analysis includes matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples are known in the art. See, for example, U.S. Pat. Nos. 6,925,389; 6,989,100; and 6,890,763, each of which is incorporated by reference herein in their entirety.

Prognosis Predictor

The information collected from the female subject is then compared to a reference set of data in order to provide a probability of achieving pregnancy. In certain aspects, the reference set includes data collected from of a cohort or plurality of women that have previously undergone the selected fertility treatment. Such data may include the fertility-associated phenotypic traits of the women, fertility-associated medical interventions, and their pregnancy outcome, i.e., whether or not a pregnancy or live-birth was achieved, per cycle of the selected reproductive method. For example, information collected from the women from the reference set could include age, smoking habits, alcohol intake, etc. The reference set could also include information regarding the fertility-associated traits of the women from the reference set. Information can be obtained by any means known in the art. In certain embodiments, the information is obtained via a questionnaire. In other embodiments, information can be obtained by analyzing a sample collected from the women in the reference set. In further embodiments of the invention, when data comprising the fertility-associated phenotypic traits of a male subject is obtained, the reference set will include data regarding those traits collected from a plurality of men. Additional details for preparing a mass data set for use, for example, in IVF studies are provided in Malizia et al., Cumulative live-birth rates after in vitro fertilization, N Engl J Med 2009; 360: 236-43, incorporated by reference herein in its entirety.

The invention provides methods and systems for predicting a pregnancy outcome in a female subject based on the subject's fertility-associated phenotypic traits and/or genotypic data. In some embodiments, methods and systems of the invention use a prognosis predictor for predicting pregnancy outcomes. The prognosis predictor can be based on any appropriate pattern recognition method that receives input data representative of a plurality of fertility-associated phenotypic traits and provides an output that indicates a probability of achieving pregnancy or a live birth. The prognosis predictor is trained with training data from a plurality of women for whom fertility-associated phenotypic traits, fertility-associated medical interventions, and pregnancy outcomes are known. The plurality of women used to train the prognosis predictor is also known as the training population. For each woman in the training population, the training data comprises (a) data representative of a plurality of fertility-associated phenotypic traits; (b) fertility-associated medical interventions; and (c) pregnancy outcome information (i.e., whether or not pregnancy occurred over a predetermined time period, for example, at a given cycle of IVF). Various prognosis predictors that can be used in conjunction with the present invention are described below. In some embodiments, additional women having known trait profiles and pregnancy outcomes can be used to test the accuracy of the prognosis predictor obtained using the training population. Such additional patients are known as the testing population.

In certain embodiments, the methods of invention use a prognosis predictor, also called a classifier, for determining the probability of achieving pregnancy. As noted above, the prognosis predictor can be based on any appropriate pattern recognition method that receives a profile, such as a profile based on a plurality of fertility-associated phenotypic traits and provides an output comprising data indicating a good prognosis or a poor prognosis, i.e., whether or not pregnancy or live birth will be achieved. As discussed previously, the profile can be obtained by completion of a questionnaire containing questions regarding certain fertility-associated phenotypic traits or the collection of a biological sample to obtain genotypic data or a combination thereof. The prognosis predictor is trained with training data from a training population of women for whom fertility-associated phenotypic traits, fertility-associated medical interventions, and pregnancy outcomes are known.

A prognosis predictor based on any of such methods can be constructed using the profiles and prognosis data of the training patients. Such a prognosis predictor can then be used to predict the pregnancy outcome of a female subject based on her profile of fertility-associated phenotypic traits, genotypic traits, or both. The methods can also be used to identify traits that discriminate between achieving pregnancy and not achieving pregnancy using a trait profile and prognosis data of the training population.

In one embodiment, the prognosis predictor can be prepared by (a) generating a reference set of women for whom fertility-associated phenotypic traits, fertility-associated medical interventions, and pregnancy outcomes are known; (b) determining for each trait, a metric of correlation between the trait and pregnancy outcome in a plurality of women having known pregnancy outcomes at a predetermined time; (c) selecting one or more traits based on said level of correlation; (d) training a prognosis predictor, in which the prognosis predictor receives data representative of the traits selected in the prior step and provides an output indicating a probability of achieving pregnancy, with training data from the reference set of subjects including assessments of traits taken from the women.

Various known statistical pattern recognition methods can be used in conjunction with the present invention. Suitable statistical methods include, without limitation, logic regression, ordinal logistic regression, linear or quadratic discriminant analysis, clustering, principal component analysis, nearest neighbor classifier analysis, and Cox proportional hazards regression. Non-limiting examples of implementing particular prognosis predictors in conjunction are provided herein to demonstrate the implementation of statistical methods in conjunction with the training set.

In some embodiments, the prognosis predictor is based on a regression model, preferably a logistic regression model. Such a regression model includes a coefficient for each of the markers in a selected set of markers of the invention. In such embodiments, the coefficients for the regression model are computed using, for example, a maximum likelihood approach.

Cox proportional hazards regression also includes a coefficient for each of the markers in a selected set of markers of the invention. Cox proportional hazards regression incorporates censored data (women in the reference set that did not return for treatment). In such embodiments, the coefficients for the regression model are computed using, for example, a maximum partial likelihood approach.

Some embodiments of the present invention provide generalizations of the logistic regression model that handle multicategory (polychotomous) responses. Such embodiments can be used to discriminate an organism into one or three or more prognosis groups. Such regression models use multicategory logit models that simultaneously refer to all pairs of categories, and describe the odds of response in one category instead of another. Once the model specifies logits for a certain (J-1) pairs of categories, the rest are redundant. See, for example, Agresti, An Introduction to Categorical Data Analysis, John Wiley & Sons, Inc., 1996, New York, Chapter 8, which is hereby incorporated by reference. Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the selected fertility-associated phenotypic traits serve as the requisite continuous independent variables. The prognosis group classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how selected fertility-associated phenotypic trait manifests in the two groups (e.g., a group that achieves pregnancy and a group that does not) and how the selected trait correlates with the manifestation of other traits. For example, LDA can be applied to the data matrix of the N members in the training sample by K genes in a combination of genes described in the present invention. Then, the linear discriminant of each member of the training population is plotted. Ideally, those members of the training population representing a first subgroup (e.g. those subjects that do not achieve pregnancy) will cluster into one range of linear discriminant values (e.g., negative) and those member of the training population representing a second subgroup (e.g. those subjects that achieve pregnancy) will cluster into a second range of linear discriminant values (e.g., positive). The LDA is considered more successful when the separation between the clusters of discriminant values is larger. For more information on linear discriminant analysis, see Duda, Pattern Classification, Second Edition, 2001, John Wiley & Sons, Inc; and Hastie, 2001, The Elements of Statistical Learning, Springer, New York; Venables & Ripley, 1997, Modern Applied Statistics with s-plus, Springer, New York.

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

In some embodiments of the present invention, decision trees are used to classify patients using expression data for a selected set of molecular markers of the invention. Decision tree algorithms belong to the class of supervised learning algorithms. The aim of a decision tree is to induce a classifier (a tree) from real-world example data. This tree can be used to classify unseen examples which have not been used to derive the decision tree.

A decision tree is derived from training data. An example contains values for the different attributes and what class the example belongs. In one embodiment, the training data is data representative of a plurality of fertility-associated phenotypic traits, fertility-associated medical interventions, and pregnancy outcomes.

The following algorithm describes a decision tree derivation:

```
Tree(Examples,Class,Attributes)
Create a root node
If all Examples have the same Class value, give the root this label
Else if Attributes is empty label the root according to the most
common value
Else begin
Calculate the information gain for each attribute
Select the attribute A with highest information gain and make
this the root attribute
For each possible value, v, of this attribute
Add a new branch below the root, corresponding to A = v
Let Examples(v) be those examples with A = v
If Examples(v) is empty, make the new branch a leaf node labeled
with the most common value among Examples
Else let the new branch be the tree created by
Tree(Examples(v),Class,Attributes - {A})
end
```

A more detailed description of the calculation of information gain is shown in the following. If the possible classes vi of the examples have probabilities P(vi) then the information content I of the actual answer is given by:

$$I(P(v_1), \ldots, P(v_n)) = n\Sigma i = 1 - P(v_i) \log_2 P(v_i)$$

The I-value shows how much information we need in order to be able to describe the outcome of a classification for the specific dataset used. Supposing that the dataset contains p positive (e.g. pregnancy achievers) and n negative (e.g. pregnancy non-achievers) examples (e.g. individuals), the information contained in a correct answer is:

$$I(p/p+n, n/p+n) = -p/p+n \log_2 p/p+n - n/p+n \log_2 n/p+n$$

where $\log_2$ is the logarithm using base two. By testing single attributes the amount of information needed to make a correct classification can be reduced. The remainder for a specific attribute A (e.g. a trait) shows how much the information that is needed can be reduced.

$$\text{Remainder}(A) = v\Sigma i = 1 \ p_i + n_i/p + n \ I(p_i/pi + n_i, n_i/p_i + n_i)$$

"v" is the number of unique attribute values for attribute A in a certain dataset, "i" is a certain attribute value, "$p_i$" is the number of examples for attribute A where the classification is positive (e.g. pregnancy achiever), "$n_i$" is the number of examples for attribute A where the classification is negative (e.g., pregnancy non-achiever).

The information gain of a specific attribute A is calculated as the difference between the information content for the classes and the remainder of attribute A:

$$\text{Gain}(A) = I(p/p+n, n/p+n) - \text{Remainder}(A)$$

The information gain is used to evaluate how important the different attributes are for the classification (how well they split up the examples), and the attribute with the highest information.

In general there are a number of different decision tree algorithms, many of which are described in Duda, Pattern Classification, Second Edition, 2001, John Wiley & Sons, Inc. Decision tree algorithms often require consideration of feature processing, impurity measure, stopping criterion, and pruning. Specific decision tree algorithms include, cut are not limited to classification and regression trees (CART), multivariate decision trees, ID3, and C4.5.

In one approach, when an exemplary embodiment of a decision tree is used, the data representative of a plurality of fertility-associated phenotypic traits across a training population is standardized to have mean zero and unit variance. The members of the training population are randomly divided into a training set and a test set. For example, in one embodiment, two thirds of the members of the training population are placed in the training set and one third of the members of the training population are placed in the test set. The expression values for a select combination of traits are used to construct the decision tree. Then, the ability for the decision tree to correctly classify members in the test set is determined. In some embodiments, this computation is performed several times for a given combination of molecular markers. In each iteration of the computation, the members of the training population are randomly assigned to the training set and the test set. Then, the quality of the combination of traits is taken as the average of each such iteration of the decision tree computation.

In some embodiments, the fertility-associated phenotypic traits and/or genotypic data are used to cluster a training set. For example, consider the case in which ten genes described in the present invention are used. Each member m of the training population will have expression values for each of the ten genes. Such values from a member m in the training population define the vector:

$$X_{1m} X_{2m} X_{3m} X_{4m} X_{5m} X_{6m} X_{7m} X_{8m} X_{9m} X_{10m}$$

where $X_{im}$ is the expression level of the $i^{th}$ gene in organism m. If there are m organisms in the training set, selection of i genes will define m vectors. Note that the methods of the present invention do not require that each the expression value of every single trait used in the vectors be represented in every single vector m. In other words, data from a subject in which one of the ith traits is not found can still be used for clustering. In such instances, the missing expression value is assigned either a "zero" or some other normalized value. In some embodiments, prior to clustering, the trait expression values are normalized to have a mean value of zero and unit variance.

Those members of the training population that exhibit similar expression patterns across the training group will tend to cluster together. A particular combination of traits of the present invention is considered to be a good classifier in this aspect of the invention when the vectors cluster into the trait groups found in the training population. For instance, if the training population includes patients with good or poor prognosis, a clustering classifier will cluster the population into two groups, with each group uniquely representing either good or poor prognosis.

Clustering is described on pages 211-256 of Duda and Hart, Pattern Classification and Scene Analysis, 1973, John Wiley & Sons, Inc., New York. As described in Section 6.7 of Duda, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda. Criterion functions are discussed in Section 6.8 of Duda.

More recently, Duda et al., Pattern Classification, 2nd edition, John Wiley & Sons, Inc. New York, has been published. Pages 537-563 describe clustering in detail. More information on clustering techniques can be found in Kaufman and Rousseeuw, 1990, Finding Groups in Data: An Introduction to Cluster Analysis, Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Nearest neighbor classifiers are memory-based and require no model to be fit. Given a query point $x_0$, the k training points $x_{(r)}$, r, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_0\|.$$

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. Profiles represent the feature space into which members of the test set are plotted. Next, the ability of the training set to correctly characterize the members of the test set is computed. In some embodiments, nearest neighbor computation is performed several times for a given combination of fertility-associated phenotypic traits. In each iteration of the computation, the members of the training population are randomly assigned to the training set and the test set. Then, the quality of the combination of traits is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, Pattern Classification, Second Edition, 2001, John Wiley & Sons, Inc; and Hastie, 2001, The Elements of Statistical Learning, Springer, New York.

The pattern classification and statistical techniques described above are merely examples of the types of models that can be used to construct a model for classification. It is to be understood that any statistical method can be used in accordance with the invention. Moreover, combinations of these described above also can be used. Further detail on other statistical methods and their implementation are described in U.S. patent application Ser. No. 11/134,688, incorporated by reference herein in its entirety It is understood that during the course of treatments, women that make-up the reference set may drop out prior to achieving a pregnancy or a live birth. It is not known whether those women eventually achieve a pregnancy at some later point or if they never became pregnant. Simply omitting those women from the reference set would result bias to the reference data set by omitting characteristics of women having a poor prognosis of achieving a pregnancy or a live-birth. Such a bias would result in reporting an overly optimistic probability of achieving a pregnancy or live birth in connection with a particular fertility treatment.

With systems and methods of the invention, rather than omitting those subjects wholesale, the present invention takes advantage of certain methods of statistical analysis to account for dropouts. The Kaplan-Meier method, for example, can be used to censor or exclude data for women in the reference set that did not return for treatment. Other forms of statistical analysis can be used in accordance with the present invention to compile the data of the reference set. For example, logistic regression, ordinal logistic regression, Cox proportional hazards regression, and other methods can all be used to compile the data within the reference set. In addition, it is contemplated that the reference set can censor or account for dropouts based on the fertility-associated traits of the women rather than making blanket assumptions regarding the fertility status of the dropouts. For example, rather than simply assuming that a dropout had the same chance of becoming pregnant as the women who continued treatment, or assuming that a dropout had no chance of becoming pregnant, the present invention can evaluate the fertility-associated traits of the dropouts and informatively censor the dropouts based on such information. In this manner, overly-optimistic estimates (resulting from the assumption that all dropouts had equal chances of achieving live birth) or overly-conservative estimates (resulting from the assumption that the dropouts had no chances of achieving live birth) are avoided.

In certain aspects, the present invention incorporates the use of artificial censoring to account for dropouts. In artificial censoring, participants are censored when they meet a predefined study criterion, such as exposure to an intervention, noncompliance with their treatment regimen, or the occurrence of a competing outcome. Further analytical methods, such as inverse-probability-of-censoring weights (IPCW), can then be used to determine what the survival experiences of the artificially censored participants would have been had they never been exposed to the intervention, complied, or not developed the competing outcome. In some embodiments, methods encompassing the use of artificial censoring and further, the use of IPCW are encompassed by the invention to account for dropouts in the reference set. Additional detail regarding the use of artificial censoring and the use of IPCW is described in Howe et al., Limitation of inverse probability-of-censoring weights in estimating survival in the presence of strong selection bias, Am J Epidemiology, 2011, incorporated by reference herein in its entirety.

As mentioned above, the information collected from the female subject is run through an algorithm trained on the reference set of data in order to provide a probability of pregnancy for a selected cycle of treatment. The pregnancy outcomes per cycle of treatment for the matched traits are then identified. Based on the identified pregnancy outcomes, the probability of pregnancy for the female subject for a given cycle of treatment is provided. Various statistical models, as discussed above, can be used in accordance with the invention to improve the accuracy of the determination.

In further aspects of the invention, the fertility-associated traits within the reference set that are assessed for determining the probability of achieving a pregnancy are adjusted per cycle of treatment. For example, in a first round of in vitro fertilization, a woman's drinking or smoking habits may be especially relevant. In a later round, however, a women's age may be more pertinent. Accordingly, aspects of the invention encompass adjusting the assessed fertility-associated traits per cycle of treatment. Methods of the invention also include adjusting the assessed fertility-associated traits according to the selected fertility-associated medical intervention. For example, if IVF is the selected procedure, the condition of the woman's uterus may be more important than in ZIFT, which uses the Fallopian tubes rather than the uterus for implantation.

Figure 2:
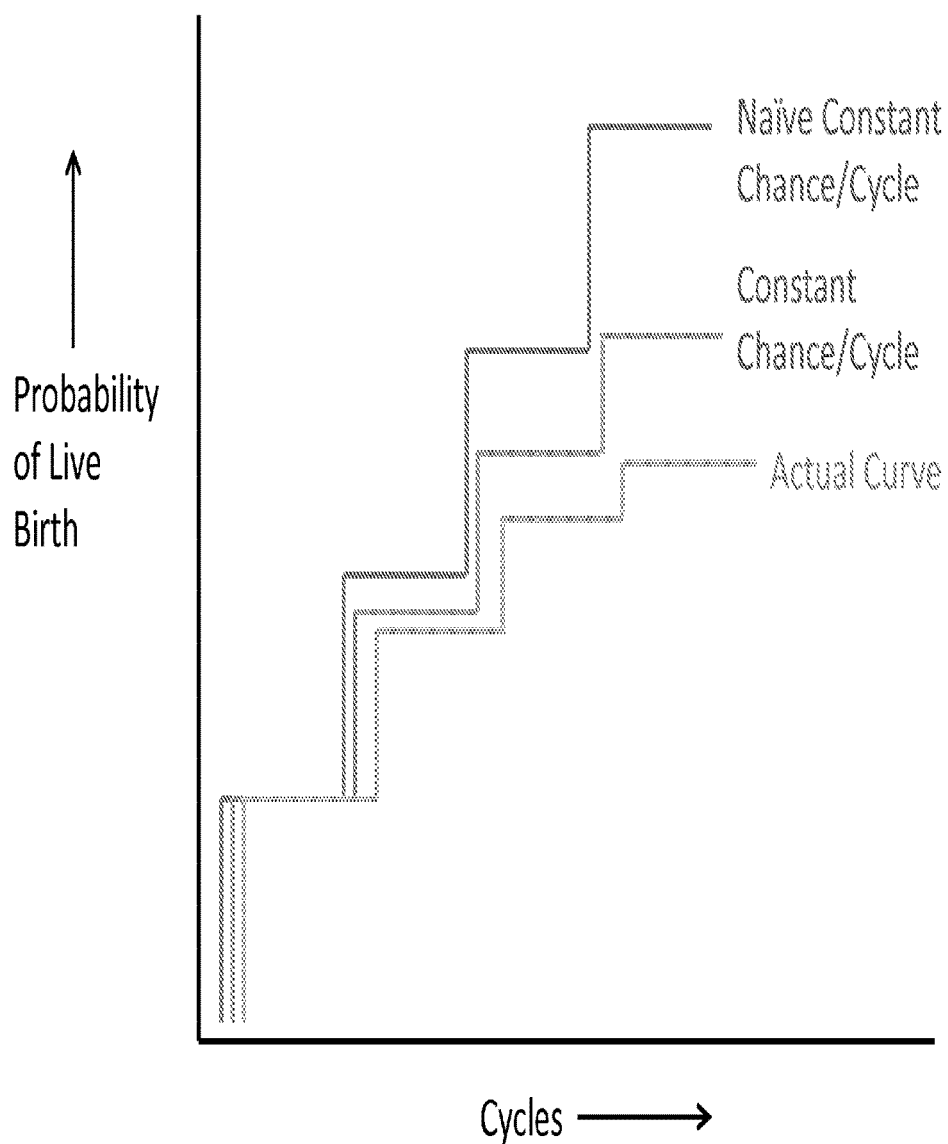
FIG. 2 is a chart depicting the probability of live birth per cycle of IVF according to observed probabilities and conventional methods of determining the probability.
Figure 3:
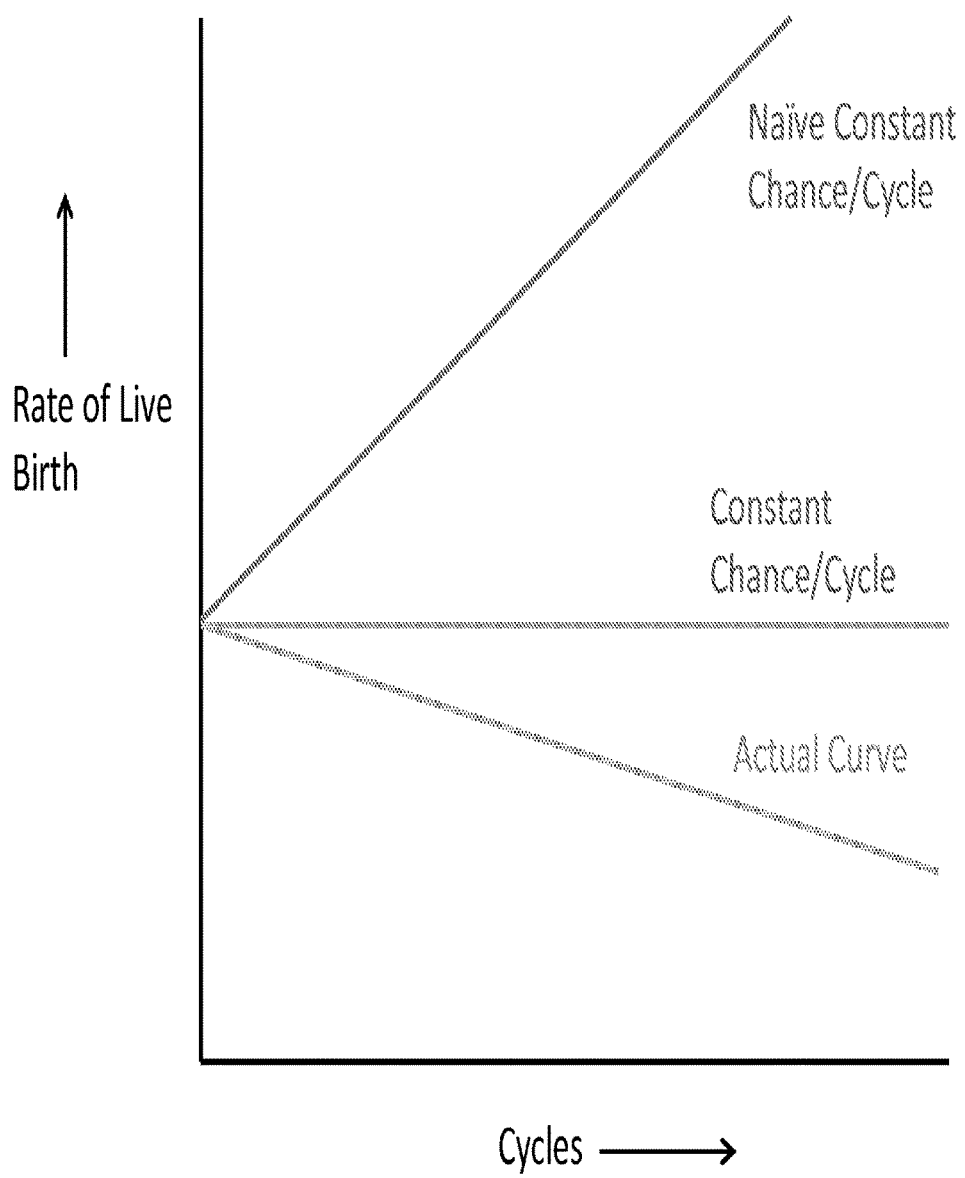
FIG. 3 is a chart depicting assumptions about the rate of live birth resulting from IVF over time.

The advantages of the disclosed methods are depicted in FIGS. 2 and 3. FIG. 2 charts the cumulative probability of live birth versus cycles of IVF treatment. The naïve constant chance/cycle and constant chance/cycle are conventional methods that have been used to predict a woman's chances of achieving pregnancy. The naïve constant chance/cycle method assumes that a woman's odds of achieving live birth are exactly the same for each cycle of IVF. Therefore, if a woman's probability of achieving live birth at a first cycle of IVF is 25%, she will have a 50% cumulative probability at a second cycle, a 75% cumulative probability at a third cycle, and a 100% cumulative probability of achieving live birth after four cycles of IVF, according to the naïve constant chance method.

The constant chance method still assumes each woman has a 25% probability of achieving live birth after a cycle of IVF but when determining the cumulative probability, applies the 25% probability to the percentage of women still not pregnant. For example, the constant chance method assumes that for the first cycle, the probability of achieving live birth is 25%. But for the second cycle, the 25% probability is applied to the 75% of the population still not pregnant, resulting in 19% probability of achieving live birth and a cumulative probability of 44% (25% first cycle+19% second cycle). For the third cycle, the cumulative probability is 58%. After four cycles of IVF, the cumulative probability of live birth is 68.5%. Even though the constant chance method is more conservative than the naïve chance method, the method still over-estimates a woman's actual odds of achieving pregnancy that results in a live birth. As shown on FIG. 2, if a woman's actual probability of achieving live birth is charted on the same graph, the estimate is even more conservative than that of the conventional methods. By factoring the fertility-associated phenotypic traits of the female subject according to the disclosed methods, aspects of the invention are able to provide a more accurate estimation of a woman's odds of achieving live birth.

FIG. 3 presents the same problem from a different perspective. FIG. 3 tracks the rate of live birth per cycle of IVF. Under the constant chance method, the rate of live birth remains the same due to the exclusion of the women in the previous cycle who actually achieved pregnancy. Under the naïve constant chance method, however, the pool remains the same, therefore, the rate of live birth actually increases per cycle of IVF. If the actual rate is charted on the same graph, the rate of live birth decreases per cycle of IVF. That means for a woman who did not achieve a pregnancy that resulted in a live birth after a first round of IVF, her probability of achieving a pregnancy that results in a live birth actually decreases per subsequent round of IVF undertaken. Methods of the invention account for this discrepancy between the naïve constant chance or constant chance determined rates and the observed rate by taking into account a female subject's fertility associated phenotypic traits to provide a more accurate estimation. Because the women of the reference set have undergone the selected reproductive method, information regarding the pregnancy outcome per cycle of treatment is available to incorporate into the reference set data. As mentioned earlier, assisted reproductive technologies such as IVF typically do not include a single cycle of treatment, but rather include several cycles of treatment. Accordingly, knowing the pregnancy outcome per cycle is useful.

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access the reference set to compare data derived from the female subject to the reference set. In other embodiments, however, the reference set is stored locally within the computer and the computer accesses the reference set within the CPU to compare subject data to the reference set. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 4:
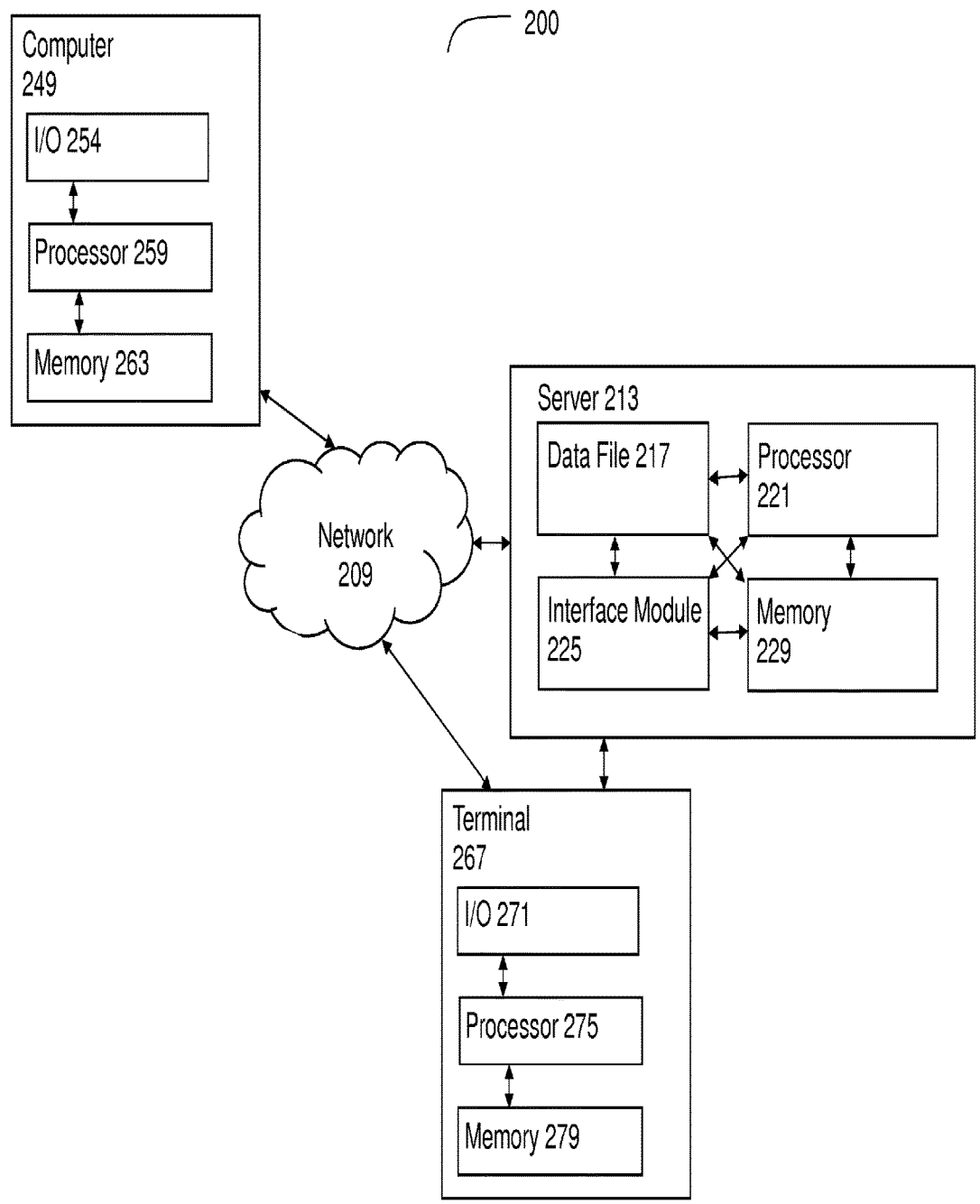
FIG. 4 illustrates a system for performing methods of the invention.

In an exemplary embodiment shown in FIG. 4, system 200 can include a computer 249 (e.g., laptop, desktop, or tablet). The computer 249 may be configured to communicate across a network 209. Computer 249 includes one or more processor 259 and memory 263 as well as an input/output mechanism 254. Where methods of the invention employ a client/server architecture, an steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

System 200 or machines according to the invention may further include, for any of I/O 249, 237, or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Figure 5:
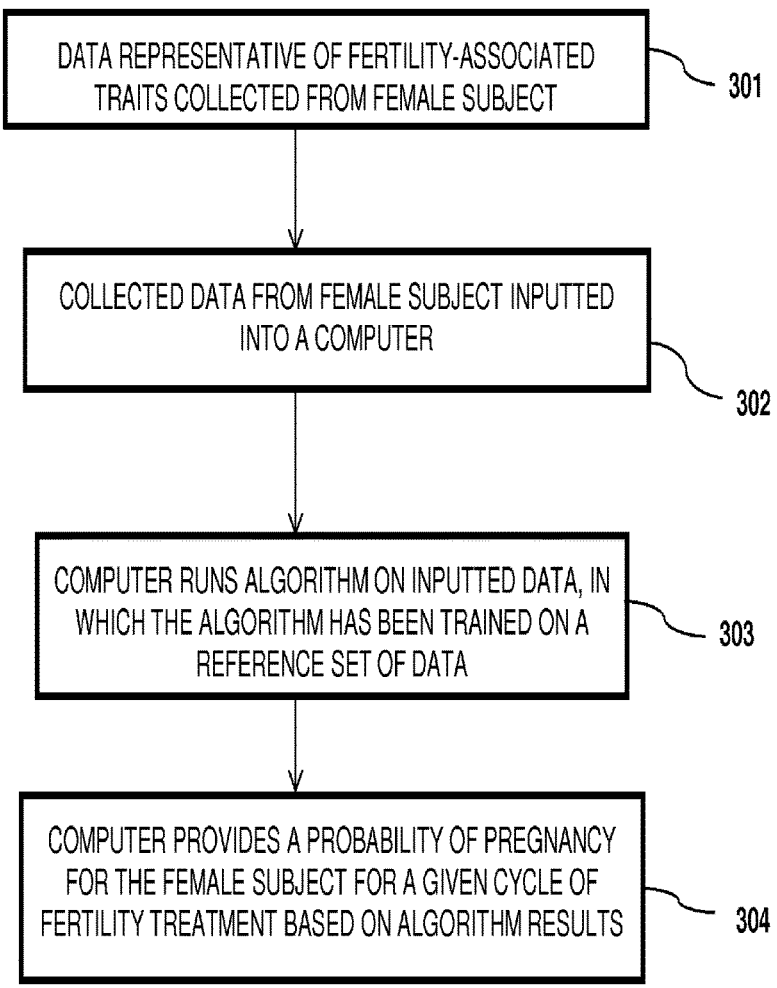
FIG. 5 is a process chart depicting the procedural steps for determining the probability of a pregnancy in a selected cycle of in vitro fertilization, according to certain embodiments.

Exemplary step-by-step methods are described schematically in FIG. 5. It will be understood that of the methods described in FIG. 3, as well as any portion of the systems and methods disclosed herein, can be implemented by computer, including the devices described above. Information is collected from the female subject regarding her fertility associated traits 301. This data is then inputted into the central processing unit (CPU) of a computer 302. The CPU is coupled to a storage or memory for storing instructions for implementing methods of the present invention. The instructions, when executed by the CPU, cause the CPU to provide a probability of successful in vitro fertilization in a selected cycle of in vitro fertilization. The CPU provides this determination by inputting the subject data into an algorithm trained on a reference set of data from a plurality of women for whom fertility-associated phenotypic traits and pregnancy outcomes for each cycle of IVF is known 303. The reference set of data may be stored locally within the computer, such as within the computer memory. Alternatively, the reference set may be stored in a location that is remote from the computer, such as a server. In this instance, the computer communicates across a network to access the reference set of data. The CPU then provides a probability of achieving pregnancy at a selected point in time based on the data entered into the algorithm.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1: Reference Set

A reference set of 12,841 women (36257 cycles) was obtained that included women that underwent a fertility treatment. For each woman in the cohort, at least one of fertility-associated phenotypic traits, fertility-associated medical interventions, or pregnancy outcomes were known.

The reference set was divided into an algorithm development set (8640 women, 24209 cycles) and a validation set (4201 women, 12048 cycles). The algorithm development set was further separated into three groups based on the reproductive technology used to treat the women. The first group included 4,312 women (6588 cycles) that underwent in vitro fertilization (IVF; "IVF group"). Of those women, many underwent more than one cycle of IVF, because a pregnancy that resulted in a live birth was not achieved at the end of a first cycle of IVF. The second group included 6,308 women (17940 cycles) that underwent a non-ART fertility treatment procedure (RE; "RE group"). Many of these women also underwent more than one cycle of treatment. The third group included 8,640 women (24209 cycles) who received either IVF or RE treatments ("All group"). The third group was not mutually exclusive of either the first or second groups, (i.e., there is overlap among women in either the first and second group and women in the third group).

Example 2: Algorithm Development

The algorithm development set was used to train an algorithm that can determine a female subject's probability of achieving pregnancy that results in a live birth at a selected point in time using a particular fertility treatment. The algorithm developed was based on a discrete time Cox proportional hazards model with time-varying covariates. Initially, indicator variables were established for categorical factors, i.e., the various fertility-associated phenotypic traits of the reference set members. Related categories were grouped where appropriate. Those variables provided the basis on which the algorithm predicts the likelihood of pregnancy outcome. For each variable, data was generally truncated at approximately the $99^{th}$ percentile. In addition, missing data was accounted for prior to developing the algorithm using imputation models derived for each numeric variable based on subjects in the reference set with complete data. Separate imputation models were developed for RE and IVF cycles.

To select the most useful variables for training the algorithm, an L1 penalized (LASSO) discrete time Cox model was used. The selected variables were cross-validated for accuracy and validity. The initial list of predicting variables was then narrowed using AIC (Akaike information criterion), which measured the relative goodness of fit in the statistical model. Certain predicting variables were further dropped or combined based on manual supervision to ensure model assumptions or to make the model more stringent. Manual supervision was also used to identify possible interaction effects between various traits, such as Male Infertility and Intrauterine Insemination. The final list of predicting variables for the IVF and RE reference sets are presented in FIGS. 6 and 7, respectively.

Example 3: Validation of Algorithm Using Validation Set

The algorithm was validated using the validation set by taking data (e.g., phenotypic and/or genotypic traits) of individual females from the reference set and running that data through the algorithm. The data was stratified based upon reproductive technology used and within each technology group, by quintile based on scores obtained for the selected fertility associated phenotypic traits. The first quintile represents the lowest 20% of women; the second quintile represents the 21%-40% group of women, the third quintile represents the 41% to 60% group of women, the fourth quintile represents the 61% to 80% group of women, and the fifth quintile represents the top 20% group of women.

Figure 8:
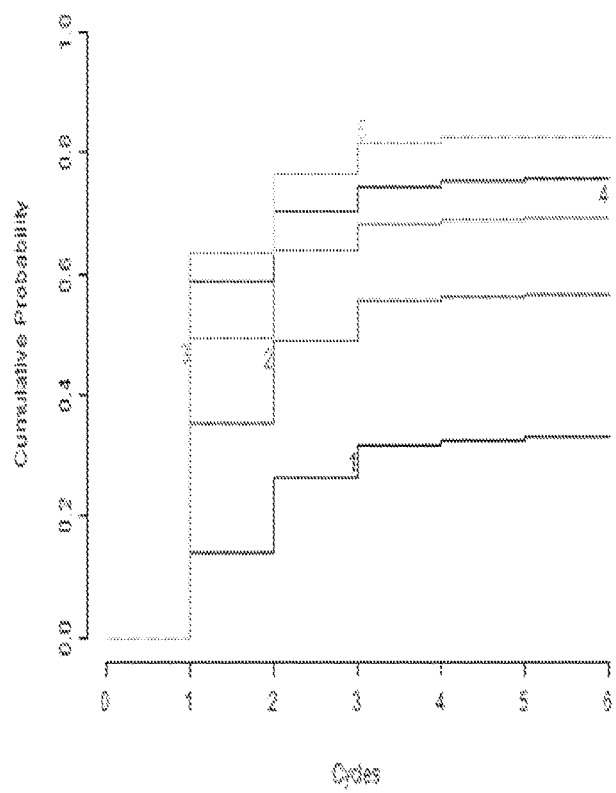
FIG. 8 is a chart depicting the cumulative probability of live birth as determined by methods of the present invention for IVF patients separated by score quintile.

FIG. 8 shows results by quintile for women from the reference set that underwent six cycles of IVF treatment. For the first quintile, the probability of achieving a pregnancy that results in a live birth after one cycle of IVF was approximately 15%, after two cycles of IVF was approximately 25%, after three cycles was approximately 30%, after four cycles was approximately 31%, after five cycles was approximately 32%, and after six cycles was approximately 33%. For the second quintile, the probability of achieving a pregnancy that results in a live birth after one cycle of IVF was approximately 38%, after two cycles of IVF was approximately 50%, after three cycles was approximately 58%, after four cycles was approximately 58%, after five cycles was approximately 59%, and after six cycles was approximately 59%. For the third quintile, the probability of achieving a pregnancy that results in a live birth after one cycle of IVF was approximately 55%, after two cycles of IVF was approximately 65%, after three cycles was approximately 70%, after four cycles was approximately 71%, after five cycles was approximately 72%, and after six cycles was approximately 72%. For the fourth quintile, the probability of achieving a pregnancy that results in a live birth after one cycle of IVF was approximately 60%, after two cycles of IVF was approximately 70%, after three cycles was approximately 75%, after four cycles was approximately 77%, after five cycles was approximately 77%, and after six cycles was approximately 77%. For the fifth quintile, the probability of achieving a pregnancy that results in a live birth after one cycle of IVF was approximately 65%, after two cycles of IVF was approximately 75%, after three cycles was approximately 80%, after four cycles was approximately 81%, after five cycles was approximately 81%, and after six cycles was approximately 81%.

The data also show that the probability of achieving a pregnancy that results in a live birth for each additional cycle of IVF undergone decreases per cycle for all five quintiles. For the first quintile, the difference between cycle zero and cycle one is about 18%, the difference between cycle one and cycle two is about 7%, the difference between cycle two and cycle three is about 5%, the difference between cycle three and cycle four is about 1%, the difference between cycle four and cycle five is about 1%, and the difference between cycle five and cycle six is about 0%. For the second quintile, the difference between cycle zero and cycle one is about 38%, the difference between cycle one and cycle two is about 12%, the difference between cycle two and cycle three is about 5%, the difference between cycle three and cycle four is about 1%, the difference between cycle four and cycle five is about 1%, and the difference between cycle five and cycle six is about 0%. For the third quintile, the difference between cycle zero and cycle one is about 50%, the difference between cycle one and cycle two is about 15%, the difference between cycle two and cycle three is about 5%, the difference between cycle three and cycle four is about 1%, the difference between cycle four and cycle five is about 1%, and the difference between cycle five and cycle six is about 0%. For the fourth quintile, the difference between cycle zero and cycle one is about 65%, the difference between cycle one and cycle two is about 10%, the difference between cycle two and cycle three is about 2%, the difference between cycle three and cycle four is about 1%, the difference between cycle four and cycle five is about 1%, and the difference between cycle five and cycle six is about 1%. For the fifth quintile, the difference between cycle zero and cycle one is about 65%, the difference between cycle one and cycle two is about 10%, the difference between cycle two and cycle three is about 5%, the difference between cycle three and cycle four is about 2%, the difference between cycle four and cycle five is about 1%, and the difference between cycle five and cycle six is about 0%.

Figure 9:
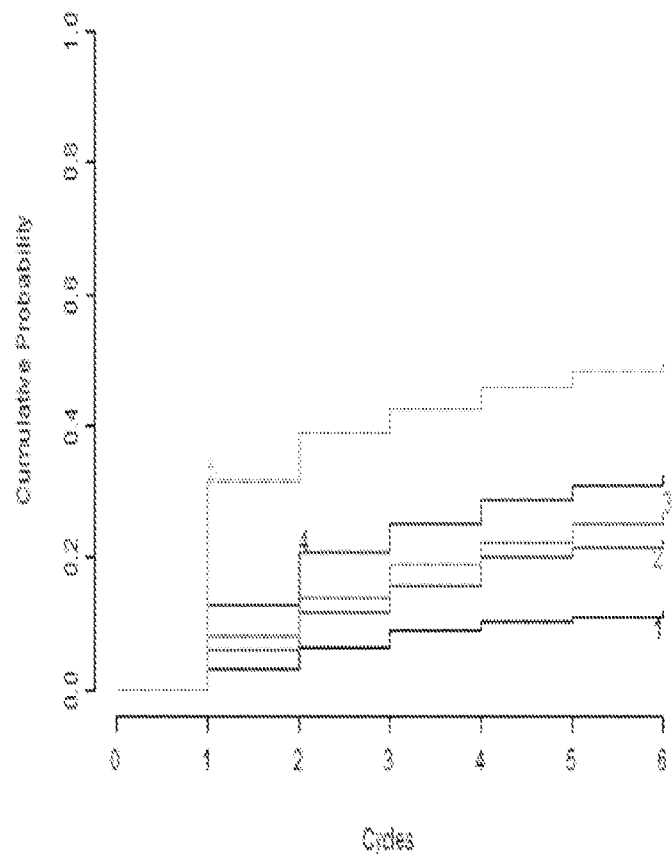
FIG. 9 a chart depicting the cumulative probability of live birth as determined by methods of the present invention for non-ART fertility treatment (RE) patients separated by score quintile.

FIG. 9 shows results by quintile for women from the reference set that underwent six cycles of RE treatment. For the first quintile, the probability of achieving a pregnancy that results in a live birth after one cycle of RE was approximately 5%, after two cycles of RE was approximately 10%, after three cycles was approximately 13%, after four cycles was approximately 14%, after five cycles was approximately 15%, and after six cycles was approximately 15%. For the second quintile, the probability of achieving a pregnancy that results in a live birth after one cycle of RE was approximately 10%, after two cycles of RE was approximately 15%, after three cycles was approximately 17%, after four cycles was approximately 18%, after five cycles was approximately 19%, and after six cycles was approximately 19%. For the third quintile, the probability of achieving a pregnancy that results in a live birth after one cycle of RE was approximately 12%, after two cycles of RE was approximately 18%, after three cycles was approximately 20%, after four cycles was approximately 23%, after five cycles was approximately 25%, and after six cycles was approximately 28%. For the fourth quintile, the probability of achieving a pregnancy that results in a live birth after one cycle of RE was approximately 15%, after two cycles of RE was approximately 20%, after three cycles was approximately 25%, after four cycles was approximately 30%, after five cycles was approximately 32%, and after six cycles was approximately 33%. For the fifth quintile, the probability of achieving a pregnancy that results in a live birth after one cycle of IVF was approximately 35%, after two cycles of RE was approximately 40%, after three cycles was approximately 43%, after four cycles was approximately 48%, after five cycles was approximately 50%, and after six cycles was approximately 50%.

The data also show that the probability of achieving a pregnancy that results in a live birth for each additional cycle of RE undergone decreases per cycle for all five quintiles. For the first quintile, the difference between cycle zero and cycle one is about 5%, the difference between cycle one and cycle two is about 5%, the difference between cycle two and cycle three is about 3%, the difference between cycle three and cycle four is about 1%, the difference between cycle four and cycle five is about 1%, and the difference between cycle five and cycle six is about 0%. For the second quintile, the difference between cycle zero and cycle one is about 10%, the difference between cycle one and cycle two is about 5%, the difference between cycle two and cycle three is about 2%, the difference between cycle three and cycle four is about 1%, the difference between cycle four and cycle five is about 1%, and the difference between cycle five and cycle six is about 0%. For the third quintile, the difference between cycle zero and cycle one is about 12%, the difference between cycle one and cycle two is about 6%, the difference between cycle two and cycle three is about 2%, the difference between cycle three and cycle four is about 3%, the difference between cycle four and cycle five is about 2%, and the difference between cycle five and cycle six is about 3%. For the fourth quintile, the difference between cycle zero and cycle one is about 15%, the difference between cycle one and cycle two is about 5%, the difference between cycle two and cycle three is about 5%, the difference between cycle three and cycle four is about 5%, the difference between cycle four and cycle five is about 3%, and the difference between cycle five and cycle six is about 1%.

For the fifth quintile, the difference between cycle zero and cycle one is about 35%, the difference between cycle one and cycle two is about 5%, the difference between cycle two and cycle three is about 3%, the difference between cycle three and cycle four is about 3%, the difference between cycle four and cycle five is about 2%, and the difference between cycle five and cycle six is about 0%.

The data show that women respond to different therapies differently and respond to the same therapy differently. See FIGS. 8 and 9. Regardless of therapy (IVF or RE) the cumulative probability of achieving a live birth for each quintile increases incrementally for each additional cycle until a plateau is reached. That benefit reaches a maximum for each quintile to the point that the therapy being used no longer increases the probability of achieving a pregnancy that results in a live birth. Rather, the probability remains constant regarding of the number of additional cycles undergone. Thus contrary to previously used reporting methods, data herein show that at a certain point in time, continuing to undergo additional therapy cycles does not correlate with increasing the probability of achieving a live birth.

The data also show that the type of fertility treatment used is important for determining a probability of achieving a pregnancy that results in live birth. The data show that using IVF compared to RE gives a female subject a higher probability of achieving a pregnancy that results in a live birth for all quintiles. See data in FIG. 8 as compared to data in FIG. 9 for all quintiles. Additionally, the data show that there is greater per/cycle benefit using IVF than there is using RE. See data in FIG. 8 as compared to data in FIG. 9 for all quintiles. Thus, a single subject may be able to increase their probability of achieving a pregnancy that results in a live birth by choosing the appropriate fertility treatment, and in this case, switching from RE treatments to IVF treatments. This is particularly useful when a woman has undergone multiple cycles of a specific therapy unsuccessfully and has reached a point that the probability of achieving a live birth using that therapy remains constant regardless of the number of additional cycles undergone.

Example 4: Impact of Dropouts on the Live Birth Rate

Figure 10:
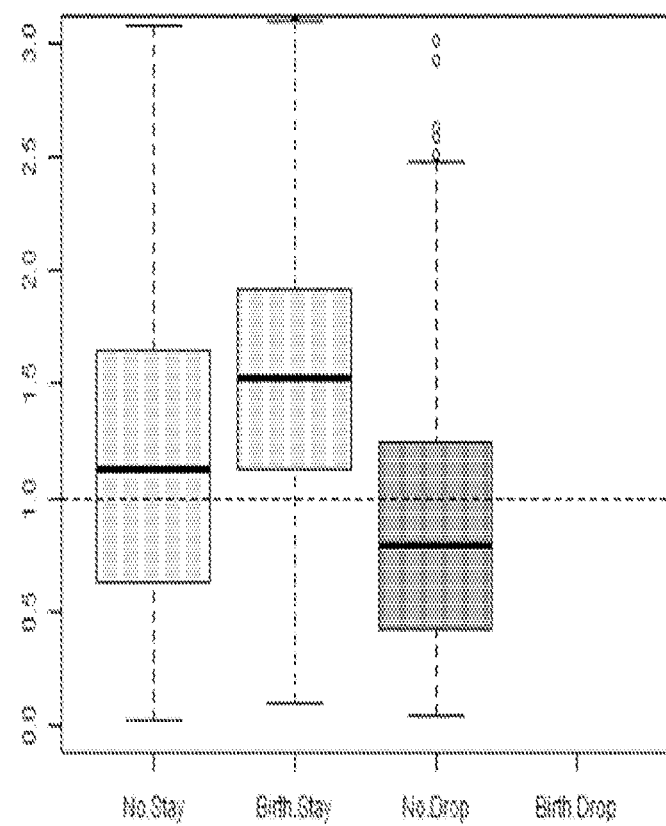
FIG. 10 is a chart depicting the varying predicted future success rates of IVF patients staying in a particular study and those who dropped out.
Figure 11:
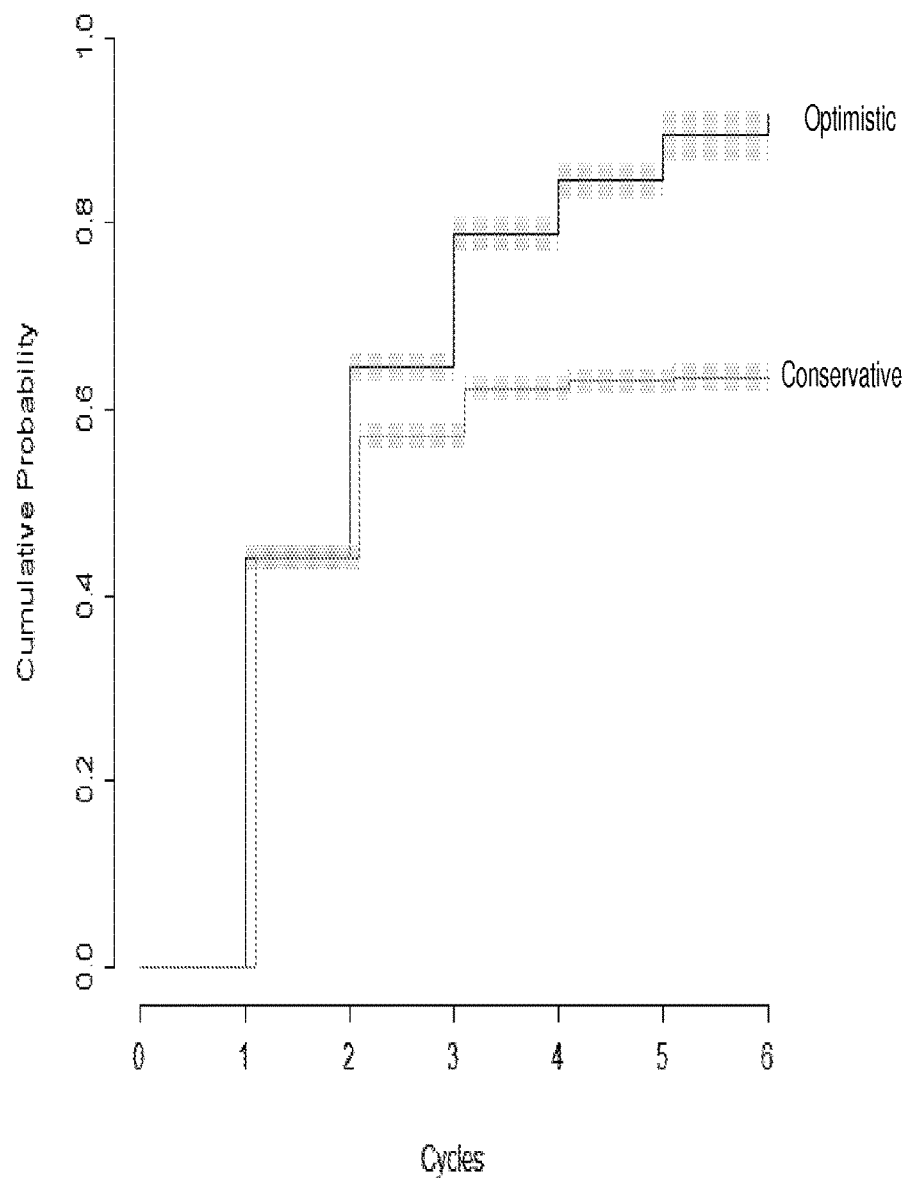
FIG. 11 is a chart depicting the cumulative probability of live birth per cycle of IVF according to optimistic and conservative approximation methods.
Figure 12:
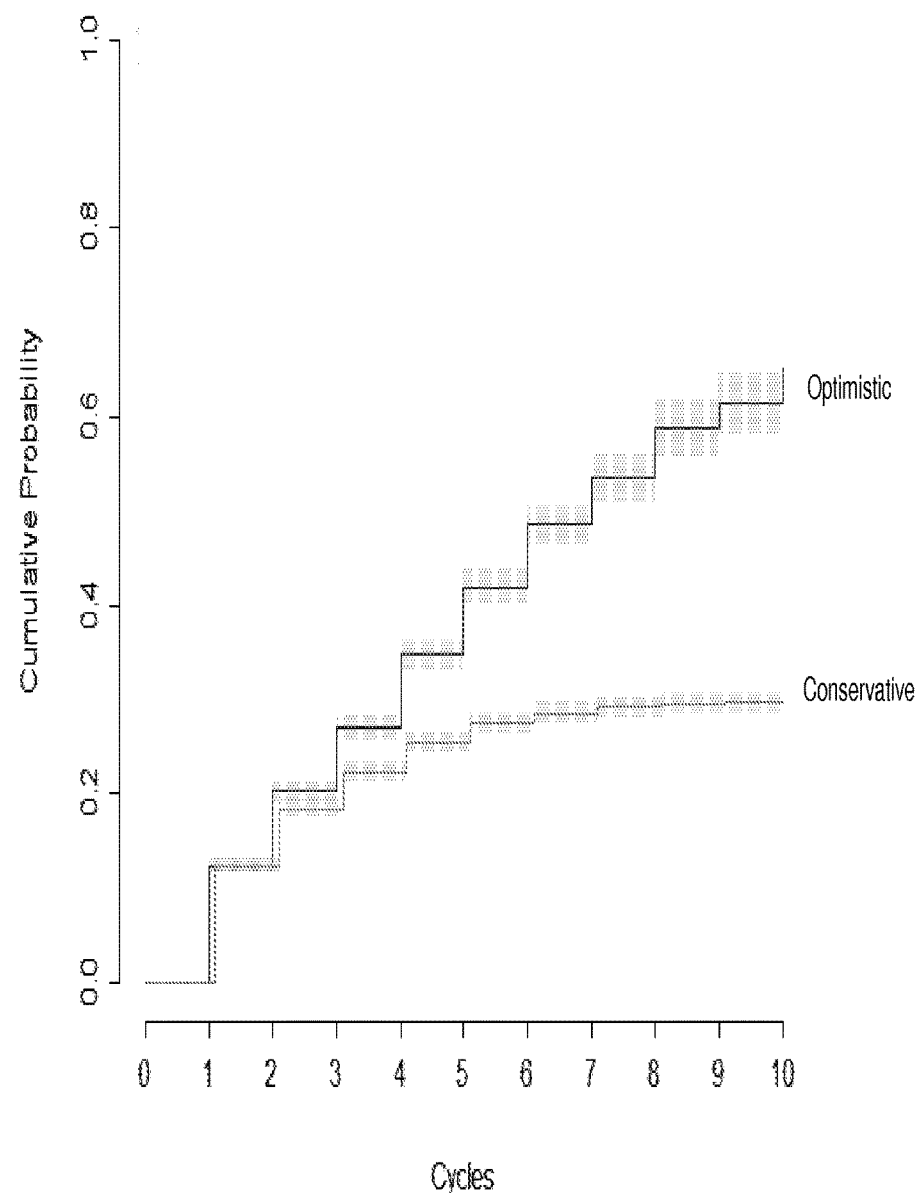
FIG. 12 is a chart depicting the cumulative probability of live birth per cycle of non-ART fertility treatments according to optimistic and conservative approximation methods.
Figure 13:
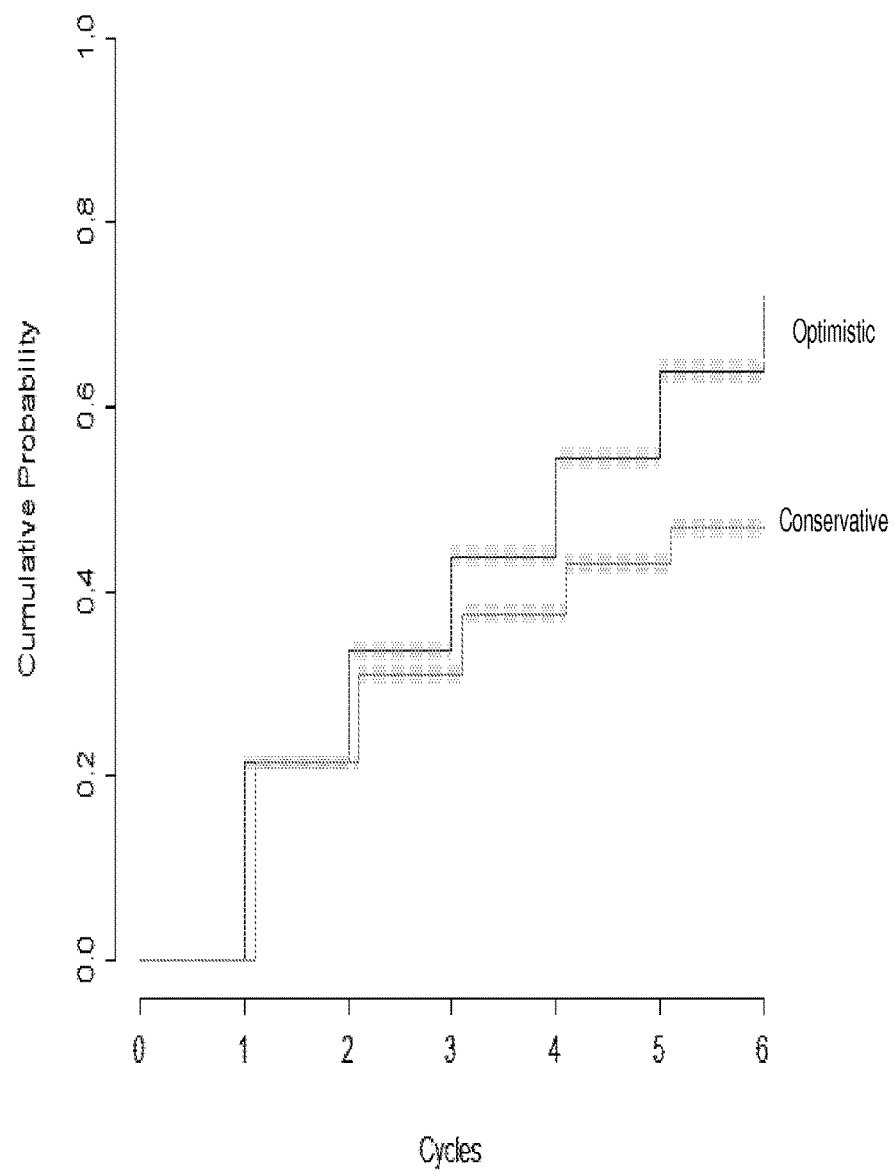
FIG. 13 is a chart depicting the cumulative probability of live birth for IVF and non-ART fertility treatments combined per cycle of treatment according to optimistic and conservative approximation methods.

It is known that certain women stop using an fertility treatment prior to achieving a pregnancy that results in a live birth ("dropouts"), and it is known that certain women dropped out of the reference set. As shown in FIG. 10, patients who did not achieve live birth and then discontinued further IVF treatment ("No.Drop") had a lower predicted future success rate than patients who did not achieve live birth but continued treatment ("No.Stay"). Accordingly, not accounting for the dropouts leads to an overly optimistic estimation of the cumulative birth rate To account for dropouts, investigations were performed using two assumptions. The first assumption was that patients who did not return for further cycles of treatment had the same chance of pregnancy resulting in a live birth as those who continued treatment (optimistic). The second assumption was that patients who did not return for further cycles of treatment had no chance of achieving live birth (conservative). The reference set was split into three groups based upon fertility treatment used (IVF group, RE group, and All group (both IVF and RE)). Based on the provided data, the algorithm determined the cumulative live-birth rate for the IVF, RE, and All group as shown in FIGS. 11-13, respectively. The cumulative birth rate was determined under both optimistic and conservative assumptions regarding patients who dropped out of the study.

FIG. 11 shows optimistic and conservative results for women from the reference set that underwent IVF treatment. As shown in FIG. 11, the conservative and optimistic birth rates were approximately 45% after one cycle of IVF. After cycle 1, the conservative and the optimistic birth rates diverge, with the optimistic birth rate having a higher probability of achieving a live birth for each additional cycle than the conservative birth rates. The divergence continuously increased with each additional cycle. FIG. 12 shows optimistic and conservative results for women from the reference set that underwent RE treatment. As shown in FIG. 12, the conservative and optimistic cumulative live birth rates were roughly 15% after one cycle of RE. After cycle 1, the conservative and the optimistic birth rates diverge, with the optimistic birth rate having a higher probability of achieving a live birth for each additional cycle than the conservative birth rates. The divergence continuously increased with each additional cycle. FIG. 13 shows optimistic and conservative results for women from the reference set that underwent both IVF and RE treatments. FIG. 13 shows that the conservative and optimistic live birth rates were 20% for All groups after one cycle. After cycle 1, the conservative and the optimistic birth rates diverge, with the optimistic birth rate having a higher probability of achieving a live birth for each additional cycle than the conservative birth rates. The divergence continuously increased with each additional cycle.

The data show that dramatically different results are obtained based on the assumptions made about the women that dropped out of the reference set. The assumption that patients who did not return for further cycles of treatment had the same chance of pregnancy resulting in a live birth as those who continued treatment is overly optimistic and results in reporting a per cycle probability higher than would be expected. The assumption that patients who did not return for further cycles of treatment that patients who did not return for further cycles of treatment had no chance of achieving live birth is overly pessimistic and results in reporting a per cycle probability lower than would be expected. The data illustrate that dropouts must be accounted for to accurately report a female's probability of achieving a pregnancy that results in a live birth at a selected point in time using a particular fertility treatment Example 5: Algorithm that Accounts for Dropouts Dropout models were developed for each of the groups within the reference set (IVF, RE, and All) and subsequently used to train the algorithm. The dropout model estimates the likelihood of dropout for each subject at each cycle. The subjects who do not dropout are weighted proportionally to the likelihood that they would have dropped out. Accounting for the dropouts in this manner attempts to preserve the population characteristics in the analysis with the progression of time.

Models were built using logistic regression statistical methods. The dropout models were then used in conjunction with Inverse Probability of Censoring Weighting (IPCW) methods to adjust the clinical models or Kaplan-Meier curves based on the reference data from an overly optimistic assessment to a more accurate determination of live birth. As simple example of developing the dropout model, assume 30% of the subjects in the reference set have high levels of follicle stimulating hormone (FSH). After cycle 1, assume 50% of the subjects with high FSH drop out, i.e., discontinue treatment. Without weights, the population at cycle 2 would only be 15% high FSH. To account for the dropouts, for cycle 2, assign a weight of 2 for a high FSH subject still in the study and a weight of 1 for a low FSH subject still in the study. With weights, the population at cycle 2 is 30% FSH (i.e., the high FSH subjects count twice), which is the same as if dropout had not occurred. Since the influence of a subject in the model is proportional to the weight, mathematically speaking, the model coefficients are corrected for bias induced by the non-random dropout.

Figure 14:
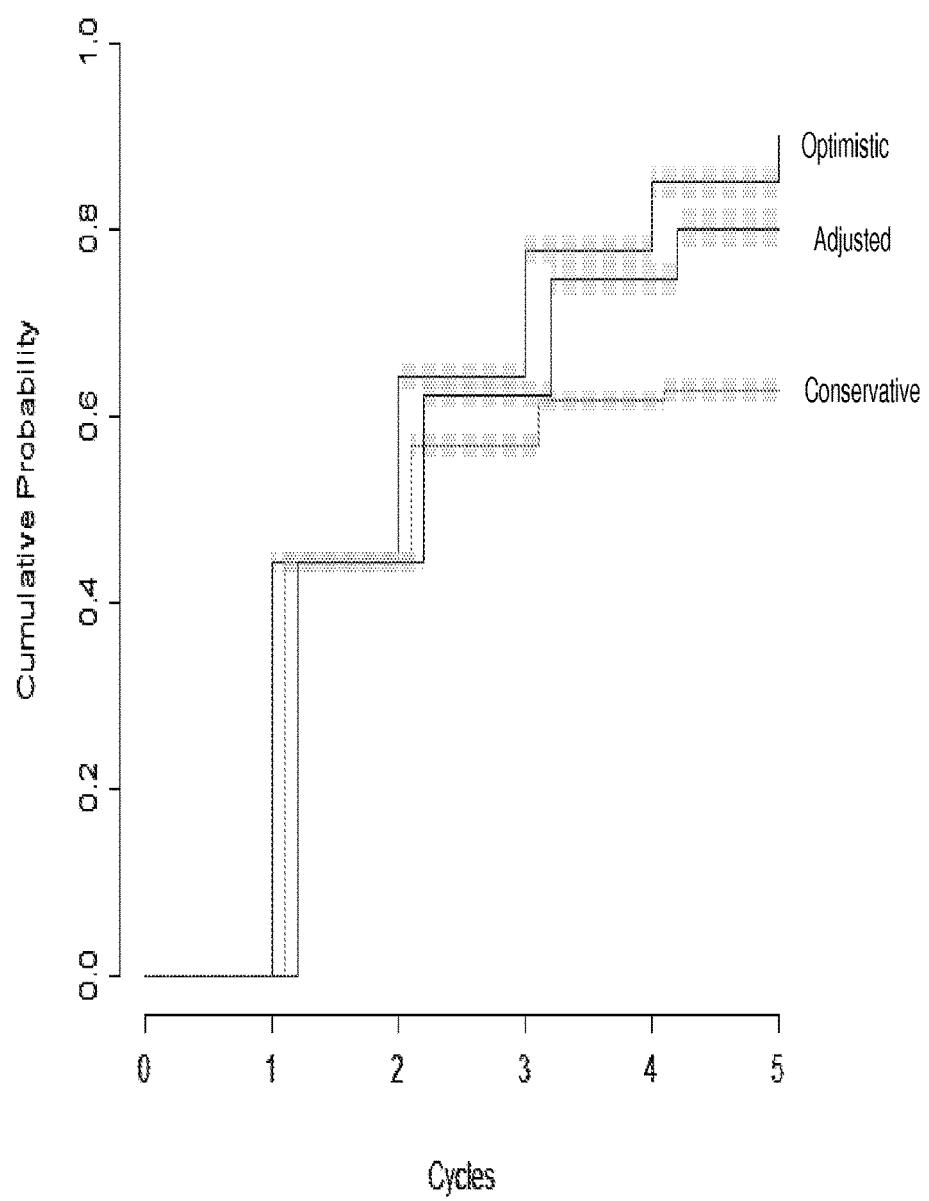
FIG. 14 is a chart depicting the cumulative probability of live birth per cycle of IVF according to optimistic and conservative approximation methods as well as the adjusted probability as determined by methods of the invention.
Figure 15:
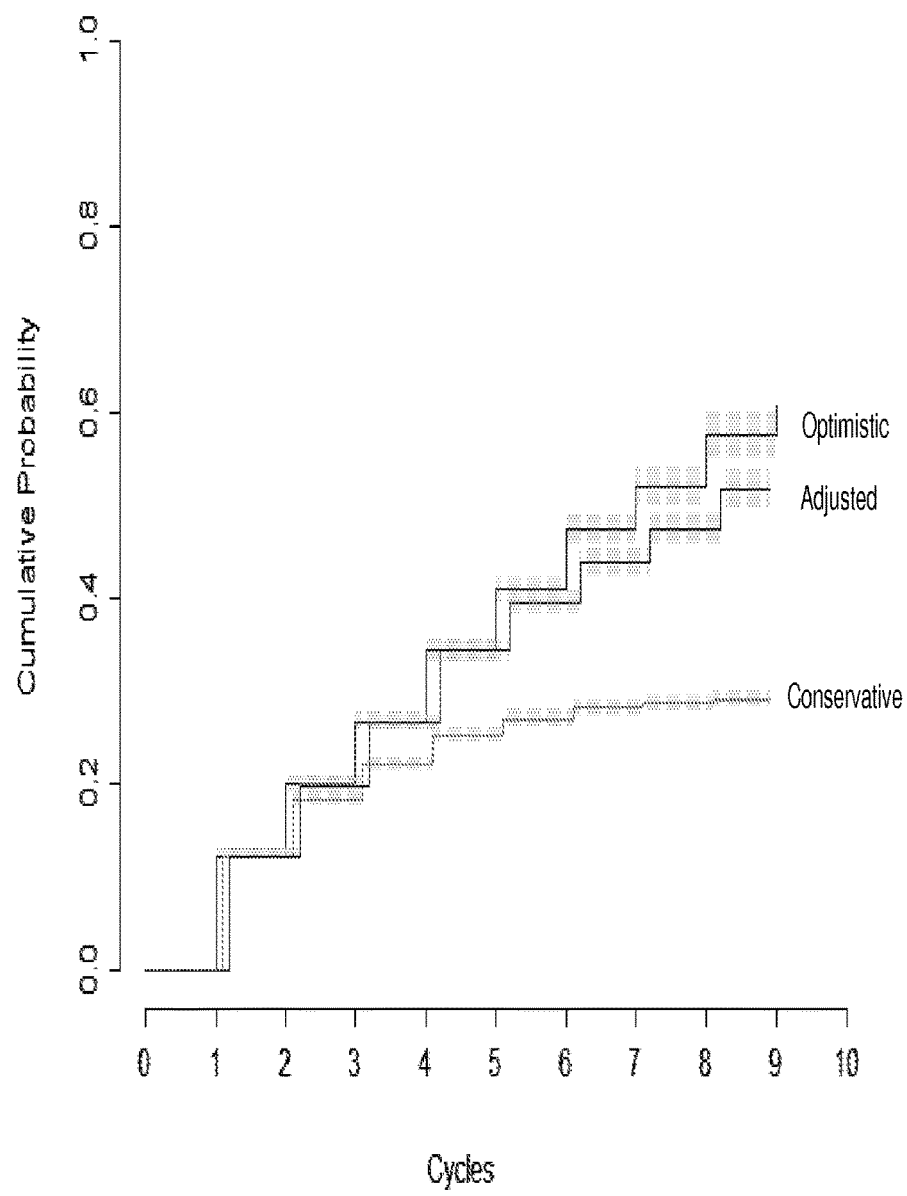
FIG. 15 is a chart depicting the cumulative probability of live birth per cycle of non-ART fertility treatments according to optimistic and conservative approximation methods as well as the adjusted probability as determined by methods of the invention.
Figure 16:
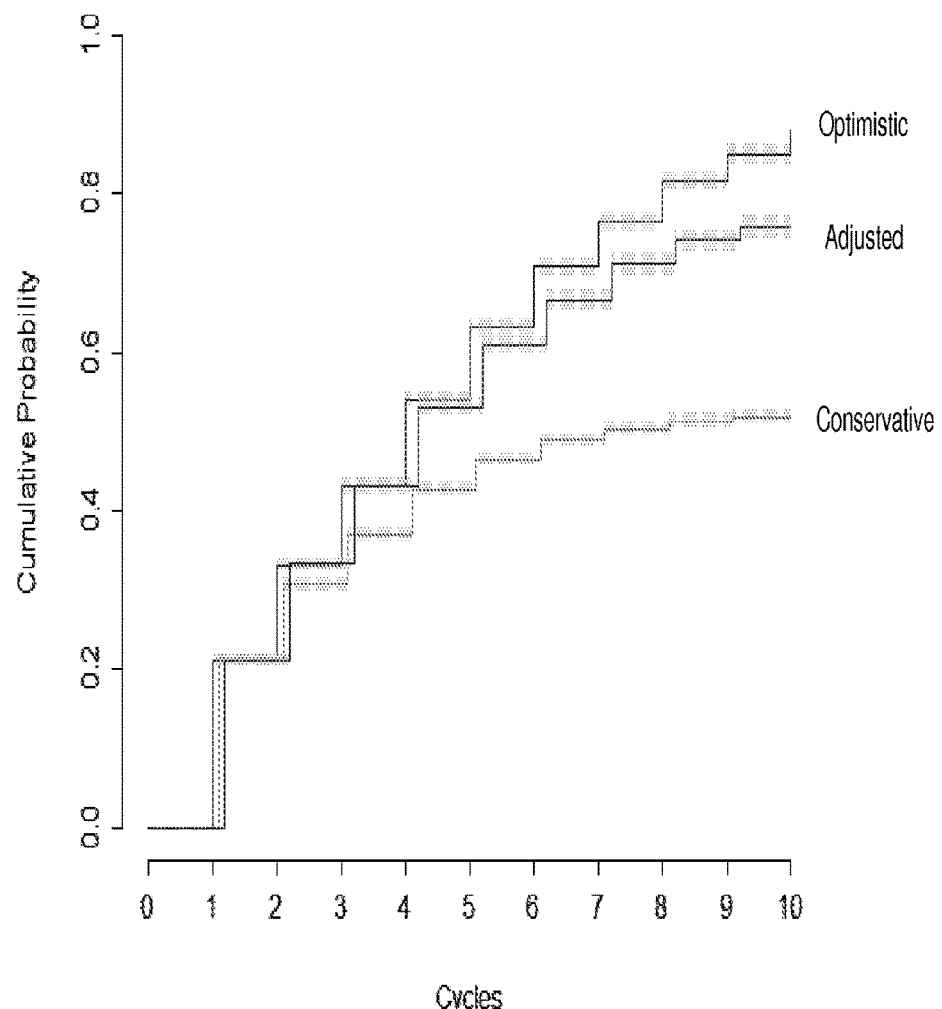
FIG. 16 is a chart depicting the cumulative probability of live birth for IVF and non-ART fertility treatments combined according to optimistic and conservative approximation methods as well as the adjusted probability as determined by methods of the invention.

Example 6: Validation of Algorithm that Accounts for Dropouts Using Validation Set The Algorithm that accounts for dropouts was then validated using the validation set by taking data (e.g., phenotypic and/or genotypic traits) of individual females from the validation set and running that data through the algorithm. The data was stratified based upon reproductive technology used. FIGS. 14-16 present adjusted birth rates that account for dropouts in the various reference sets. Optimistic and conservative rates are also provided along with the adjusted rate. As shown in FIG. 16, the cumulative live birth rate using IVF is approximately the same for the first two cycles of treatment using optimistic, conservative, or "adjusted" methods. As cycles progress, however, the adjusted birth rate is observed to be between the optimistic and conservative birth rate. Similar trends are observed for the RE and All groups, as shown in FIGS. 15-16, respectively. Good predictive accuracy was observed for all three models based on AUC (Area Under Curve) analysis. IVF model AUC was determined to be 0.71±0.02; the RE Model AUC was determined to be 0.73±0.02; and the All Model AUC was determined to be 0.81±0.02.

As those Figures demonstrate, the more accurate assessment of a subject's probability for achieving a live birth does not follow the optimistic rate or the conservative rate but lies between those rates respectively. Accordingly, using the methods disclosed herein, one can determine a probability of achieving a pregnancy at a selected point in time with greater accuracy and confidence than previously used algorithms.

What is claimed is:

1. A method for determining a probability of achieving a pregnancy at a selected point in time, the method comprising:

training a prognosis predictor, using training data from a population that includes women who ceased pregnancy attempts after one or more reproductive cycles without conception and women who continued pregnancy attempts until live birth, to determine a correlation between fertility-associated characteristics and known pregnancy outcomes, the fertility-associated characteristics comprising phenotypic traits, fertility-associated interventions, and pregnancy outcomes;

accepting as input, data representative of a plurality of fertility-associated phenotypic traits of a female subject;

analyzing the input data using the prognosis predictor;

providing, based on the analysis, a probability of achieving a pregnancy at a selected point in time; and treating the female subject with a fertility treatment based on the probability of achieving a pregnancy.

2. The method of claim 1, wherein the pregnancy of the female subject results in a live birth.

3. The method of claim 1, wherein said fertility-associated traits are adjusted per pre-specified time interval or fertility-associated medical intervention.

4. The method of claim 1, wherein said input data are obtained from at least one selected from the group consisting of: a questionnaire, a medical history of said subject, a family medical history of said subject, and a combination thereof.

5. The method of claim 1, wherein said input data are obtained by analyzing a sample collected from a person selected from the group consisting of: said female subject, intimate partners of said subject, blood-related relatives of said subject, gamete donors, embryo donors, gestational carriers, and a combination thereof.

6. The method of claim 5, wherein said sample is a human tissue or bodily fluid.

7. The method of claim 1, wherein the input data further comprises fertility-associated genotypic traits of the female subject.

8. The method of claim 7, wherein the training data further comprises fertility-associated genotypic traits.

9. The method of claim 7, wherein the genotypic traits of the subject are obtained by conducting an assay on a sample from the subject to determine the presence or absence of a genetic variation that is associated with infertility.

10. The method of claim 9, wherein the assay is selected from the group consisting of: sequencing, hybridization to an array, and an amplification reaction.

11. The method of claim 9, wherein the genetic variation is selected from the group consisting of: a single nucleotide polymorphism, a deletion, an insertion, a rearrangement, a copy number variation, and a combination thereof.

12. The method of claim 7, wherein the genotypic traits are reflective of expression levels of one or more fertility-associated genes.

13. The method of claim 1, wherein the fertility-associated phenotypic traits comprise a trait selected from Table 1.

14. The method of claim 1, wherein the input data further comprises a plurality of fertility-associated phenotypic traits of a male subject.

15. A method for determining a probability of achieving a pregnancy at a selected point in time, the method comprising:

using at least one computer to train a prognosis predictor using training data from a population that includes women who ceased pregnancy attempts after one or more reproductive cycles without conception and women who continued pregnancy attempts until live birth, to determine a correlation between fertility-associated characteristics and known pregnancy outcomes, the fertility-associated characteristics comprising phenotypic traits, fertility-associated interventions, and pregnancy outcomes;

inputting data representative of a plurality of fertility-associated phenotypic traits of a female subject into the at least one computer;

analyzing the input data using the prognosis predictor;

causing the at least one computer to provide a probability of achieving a pregnancy at a selected point in time based on the analysis; and treating the female subject with a fertility treatment based on the probability of achieving a pregnancy.

* * * * *